US010988759B2

(12) United States Patent
Baker et al.

(10) Patent No.: US 10,988,759 B2
(45) Date of Patent: *Apr. 27, 2021

(54) HIGH THROUGHPUT PROTEIN-PROTEIN INTERACTION SCREENING IN YEAST LIQUID CULTURE

(71) Applicant: University of Washington, Seattle, WA (US)

(72) Inventors: David Baker, Seattle, WA (US); David Younger, Seattle, WA (US); Eric Klavins, Seattle, WA (US)

(73) Assignee: UNIVERSITY OF WASHINGTON, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/856,506

(22) Filed: Apr. 23, 2020

(65) Prior Publication Data

US 2021/0002629 A1 Jan. 7, 2021

Related U.S. Application Data

(63) Continuation-in-part of application No. 15/407,215, filed on Jan. 16, 2017, now abandoned.

(60) Provisional application No. 62/279,227, filed on Jan. 15, 2016.

(51) Int. Cl.
*C12N 15/10* (2006.01)

(52) U.S. Cl.
CPC ................................ *C12N 15/1055* (2013.01)

(58) Field of Classification Search
CPC .................................................. C12N 15/1055
See application file for complete search history.

(56) References Cited

U.S. PATENT DOCUMENTS

| 6,423,538 | B1 | 7/2002 | Wittrup et al. |
| 6,841,352 | B2 * | 1/2005 | Ostanin .............. C12N 15/1055 435/4 |
| 9,005,927 | B2 | 4/2015 | Hufton et al. |
| 9,139,637 | B2 | 9/2015 | Wittrup et al. |
| 10,017,758 | B1 | 7/2018 | Peikon et al. |
| 2008/0176756 | A1 | 7/2008 | Siegel et al. |
| 2010/0075326 | A1 * | 3/2010 | Jin .......................... C12Q 1/025 435/6.11 |
| 2013/0085072 | A1 | 4/2013 | Bradbury et al. |

FOREIGN PATENT DOCUMENTS

| CA | 2666336 | 1/2014 |
| WO | 2002/086120 A1 | 3/2002 |
| WO | 2007/145661 A2 | 12/2007 |
| WO | 2011/092233 A1 | 8/2011 |

OTHER PUBLICATIONS

Hastie et al., Yeast two-hybrid interaction partner screening through in vivo Cre-mediated Binary Interaction Tag generation, Nov. 2007, Nucleic Acids Research, vol. 35, pp. 1-8 (Year: 2007).*

Suzuki et al. Roles of sexual cell agglutination in yeast mass mating, 2003, Genes Genet. Syst., vol. 78, pp. 211-219 (Year: 2003).*

Put, et al., "The heat resistance of ascospores of four *Saccharomyces* spp. isolated from spoiled heat-processed soft drinks and fruit products," Journal of Applied Bacteriology, vol. 52, No. 2, pp. 235-243, 1982.

Richman, et al., "Biosensor detection systems: engineering stable, high-affinity bioreceptors by yeast surface display," Methods in Molecular Biology, vol. 504, pp. 323-350, 2009.

Rodriguez, et al., "Diversification under sexual selection: the relative roles of mate preference strength and the degree of divergence in mate preferences," Ecology letters, vol. 16, No. 8, pp. 964-974, 2013.

Safran, et al., "Contributions of natural and sexual selection to the evolution of premating reproductive isolation: a research agenda," Trends in ecology & evolution, vol. 28, No. 11, pp. 643-650, 2013.

Sauer, "Functional expression of the cre-lox site-specific recombination system in the yeast *Saccharomyces cerevisiae*," Molecular and cellular biology, vol. 7, No. 6, pp. 2087-2096, 1987.

Segall, "Polarization of yeast cells in spatial gradients of alpha mating factor," Proceedings of the National Academy of Sciences, vol. 90, No. 18, pp. 8332-8336, 1993.

Shou, et al., "Synthetic cooperation in engineered yeast populations," Proceedings of the National Academy of Sciences, vol. 104, No. 6, pp. 1877-1882, 2007.

Sreekrishna, et al., "Construction of strains of *Saccharomyces cerevisiae* that grow on lactose," Proceedings of the National Academy of Sciences, vol. 82, No. 23, pp. 7909-7913, 1985.

Sundstrom, "Adhesins in Candida albicans," Current opinion in microbiology, vol. 2, No. 4, pp. 353-357, 1999.

Tanaka, et al., "Recent developments in yeast cell surface display toward extended applications in biotechnology," Applied Microbiology & Biotechnology, vol. 95, No. 3, pp. 577-591, 2012.

Terrance, et al., "Sexual agglutination in *Saccharomyces cerevisiae*," Journal of bacteriology, vol. 148, No. 3, pp. 889-896, 1981.

Thompson, et al., "SYNZIP protein interaction toolbox: in vitro and in vivo specifications of heterospecific coiled-coil interaction domains," ACS synthetic biology, vol. 1, No. 4, pp. 118-129, 2012.

Vidal, "Interactome modeling," FEBS letters, vol. 579, No. 8, pp. 1834-1838, 2005.

Wahlbom, et al., "Molecular analysis of a *Saccharomyces cerevisiae* mutant with improved ability to utilize xylose shows enhanced expression of proteins involved in transport, initial xylose metabolism, and the pentose phosphate pathway," Applied and environmental microbiology, vol. 69, No. 2, pp. 740-746, 2003.

(Continued)

*Primary Examiner* — Nancy J Leith
(74) *Attorney, Agent, or Firm* — McDonnell Boehnen Hulbert & Berghoff LLP

(57) ABSTRACT

The present invention relates to methods and compositions for the high throughput screening of protein-protein interactions in yeast liquid culture. Protein fusions non-native to yeast may be expressed to replace endogenous sexual agglutination proteins and mediate library-by-library interrogation of protein interactions. The methods and compositions of the invention can be utilized for the characterization of protein interaction networks in high throughput for both binding affinity and specificity, which is crucial for understanding cellular functions, screening therapeutic candidates, and evaluating engineered protein networks.

28 Claims, 37 Drawing Sheets

Specification includes a Sequence Listing.

(56) References Cited

OTHER PUBLICATIONS

Wang, et al., "A modular cell-based biosensor using engineered genetic logic circuits to detect and integrate multiple environmental signals," Biosensors and Bioelectronics, vol. 40, No. 1, pp. 368-376, 2013.
Wang, et al., "Three-dimensional reconstruction of protein networks provides insight into human genetic disease," Nature biotechnology, vol. 30, No. 2, pp. 159-164, 2012.
Weaver-Feldhaus, et al., "Yeast mating for combinatorial Fab library generation and surface display" FEBS Letters, vol. 564, No. 1-2, pp. 24-34, 2004.
Weber, et al., "Emerging biomedical applications of synthetic biology," Nature Reviews Genetics, vol. 13, No. 1, pp. 21-35, 2012.
Wen, et al., "Yeast surface display of trifunctional minicellulosomes for simultaneous saccharification and fermentation of cellulose to ethanol," Applied and environmental microbiology, vol. 76, No. 4, pp. 1251-1260, 2010.
Wilson, et al., "The LoxP/CRE system and genome modification," Gene Knockout Protocols. Humana Press, pp. 83-94, 2001.
Xie, et al., "Accelerated and adaptive evolution of yeast sexual adhesins." Molecular biology and evolution, msr145, 2011.
Yu, et al., "High-quality binary protein interaction map of the yeast interactome network" Science, vol. 322, No. 5898, pp. 104-110, 2008.
Zhao, et al., "Interaction of α-agglutinin and a-agglutinin, *Saccharomyces cerevisiae* sexual cell adhesion molecules," Journal of Bacteriology, vol. 183.9, pp. 2874-2880, 2001.
Haber, J.E., Bisexual Mating Behavior in a Diploid of *Saccharomyces cerevisiae*: Evidence for Genetically Controlled Non-Random Chromosome Loss During Vegetative Growth; Genetics, vol. 78, pp. 843-858, 1974 (Year 1974).
Goossens et al., Molecular Mechanism of Flocculation Self-Recognition in Yeast and Its Role in Mating and Survival; mBio vol. 6, No. 2, e00427-15, pp. 1-16, 2015 (Year: 2015).
Rothstein, R., Targeting, Disruption, Replacement and Allele Rescue: Integrative DNA Transformation in Yeast; Methods in Enzymology, vol. 194, pp. 281-301, 1991 (Year: 1991).
Balagaddé, et al. "A synthetic *Escherichia coli* predator-prey ecosystem," Molecular systems biology 4.1, vol. 187, 8 pages, 2008.
Banta, "Replacing Antibodies: Engineering New Binding Proteins" Annual Review of Biomedical Engineering, vol. 15, pp. 93-113, 2013.
Barton, et al., "Why sex and recombination?" Science, vol. 281, pp. 1986-1990, 1998.
Bender, et al., "Pheromones and pheromone receptors are the primary determinants of mating specificity in the yeast *Saccharomyces cerevisiae*," Genetics, vol. 121, pp. 463-76, 1989.
Boder, et al., "Yeast surface display of a noncovalent MHC class II heterodimer complexed with antigenic peptide," Biotechnology and Bioengineering, vol. 92, No. 4, pp. 485-491, 2005.
Boder, et al., "Yeast surface display for screening combinatorial polypeptide libraries," Nature biotechnology, vol. 15.6, pp 553-557, 1997.
Boder, et al., "Yeast surface display system for antibody engineering," Immunotechnology, vol. 2.4, p. 283, 1996.
Cappellaro, et al., "Mating type-specific cell-cell recognition of *Saccharomyces cerevisiae*: cell wall attachment and active sites of a- and alpha-agglutinin," EMBO Journal, vol. 13, No. 20, pp. 4737-4744, 1994.
Cardinale, et al., "Contextualizing context for synthetic biology—identifying causes of failure of synthetic biological systems," Biotechnology Journal, vol. 7, pp. 7, pp. 856-866, 2012.
Casini, et al., "R2oDNA designer: computational design of biologically neutral synthetic DNA Sequences." ACS Synthetic Biology, vol. 3, No. 8, pp. 525-528, 2014.
Chan, et al., "Isolation and genetic analysis of *Saccharomyces cerevisiae* mutants supersensitive to G1 arrest by a factor and alpha factor pheromones," Molecular and Cellular Biology, vol. 2, No. 1, pp. 11-20, 1982.
Chao, et al., "Fine epitope mapping of anti-epidermal growth factor receptor antibodies through random mutagenesis and yeast surface display," Journal of molecular biology, vol. 342, No. 2, pp. 539-550, 2004.
Chee, et al., "New and redesigned pRS plasmid shuttle vectors for genetic manipulation of *Saccharomyces cerevisiae*," G3: Genes| Genomes| Genetics, vol. 2, No. 5, pp. 515-526, 2012.
Chen, et al., "Cell-cell fusion," FEBS letters, vol. 581, No. 11, pp. 2181-2193, 2007.
Chenevert, et al., "Identification of genes required for normal pheromone-induced cell polarization in *Saccharomyces cerevisiae*," Genetics, vol. 136, No. 4, pp. 1287-1296, 1994.
Cherf, et al., "Applications of yeast surface display for protein engineering", Methods in Molecular Biology, vol. 1319, pp. 155-175, 2015.
Colegrave, "Sex releases the speed limit on evolution," Nature, vol. 420, No. 6916, pp. 664-666, 2002.
Daar, et al., "Top ten biotechnologies for improving health in developing countries," Nature genetics, vol. 32, No. 2, pp. 229-232, 2002.
Daniel, et al., "Synthetic analog computation in living cells," Nature, vol. 497, pp. 619-623, 2013.
Daugherty, et al., "Antibody affinity maturation using bacterial surface display," Protein Engineering, vol. 11, No. 9, pp. 825-832, 1998.
Dranginis, et al., "A Biochemical Guide to Yeast Adhesins: Glycoproteins for Social and Antisocial Occasions," Microbiology and Molecular Biology Reviews, vol. 71, No. 2, pp. 282-294, 2007.
Dunham, "Synthetic ecology: a model system for cooperation," Proceedings of the National Academy of Sciences, vol. 104, No. 6, pp. 1741-1742, 2007.
Dunn, et al., "Natural and sexual selection act on different axes of variation in avian plumage color," Science Advances, vol. 1.2, e1400155, 7 pages, 2015.
Dura, et al., "Spatially and temporally controlled immune cell interactions using microscale tools," Current opinion in immunology, vol. 35, pp. 23-29, 2015.
Eby, et al., "Characterization, performance, and applications of a yeast surface display-based biocatalyst", RSC Advances, vol. 5, pp. 19166-19175, 2015.
Fletcher, et al., "A basis set of de novo coiled-coil peptide oligomers for rational protein design and synthetic biology," ACS synthetic biology, vol. 1, pp. 240-250, 2012.
Gai, et al., "Yeast surface display for protein engineering and characterization," Current opinion in structural biology, vol. pp. 467-473, 2007.
Gera, et al., "Protein selection using yeast surface display," Methods. vol. 60, No. 1, pp. 15-26, 2013.
Gibson, et al., "Enzymatic assembly of DNA molecules up to several hundred kilobases," Nature methods, vol. 6, No. 5, pp. 343-345, 2009.
Greig, et al., "Hybrid speciation in experimental populations of yeast." Science, vol. 298, pp. 1773-1775, 2002.
Gu, et al., "Multiplex single-molecule interaction profiling of DNA-barcoded proteins," Nature, vol. 515, 14 pages , 2014.
Guo, et al., "A *Saccharomyces* gene family involved in invasive growth, cell-cell adhesion, and mating," Proceedings of the National Academy of Sciences, vol. 97, No. 22, pp. 12158-12163, 2000.
Haber, "Mating-type genes and MAT switching in *Saccharomyces cerevisiae*," Genetics, vol. 191, pp. 33-64, 2012.
Head, et al., "Female mate preferences for male body size and shape promote sexual isolation in threespine sticklebacks," Ecology and evolution, vol. 3, pp. 2183-2196, 2013.
Howitt, et al., "Technologies for global health," The Lancet, vol. 380, pp. 507-535, 2012.
Huang, et al., "Conserved WCPL and CX4C domains mediate several mating adhesin interactions in *Saccharomyces cerevisiae*," Genetics, vol. 182, pp. 173-189, 2009.
Ito, et al., "Transformation of intact yeast cells treated with alkali cations," Journal of bacteriology, vol. 153, No. 1, pp. 163-168, 1983.
Jackson, et al., "Courtship in *Saccharomyces cerevisiae*: an early cell-cell interaction during mating," Molecular and Cellular Biology, vol. 10, No. 5, pp. 2202-2213, 1990.

(56) References Cited

OTHER PUBLICATIONS

James, et al., "Biophysical mechanism of T-cell receptor triggering in a reconstituted system," Nature, vol. 487, pp. 64-69, 2012.
Kaster, et al., "Hygromycin B resistance as dominant selectable marker in yeast," Current genetics, vol. 8, pp. 1984, pp. 353-358, 1984.
Keddar, et al., "Color ornaments and territory position in king penguins." Behavioural processes, vol. 119, pp. 32-37, 2015.
Khakhar, et al., "Cell—Cell Communication in Yeast Using Auxin Biosynthesis and Auxin Responsive CRISPR Transcription Factors," ACS synthetic biology, vol. 2016.
Lipke, et al., "Sexual agglutination in budding yeasts: structure, function, and regulation of adhesion glycoproteins." Microbiological reviews, vol. 56, No. 1, pp. 180-194, 1992.
Malleshaiah, et al., "The scaffold protein Ste5 directly controls a switch-like mating decision in yeast," Nature, vol. 465, pp. 101-105, 2010.
Martins, et al., "Evolution and stability of ring species," Proceedings of the National Academy of Sciences, vol. 110, No. 13, pp. 5080-5084, 2013.
McIsaac, et al., "Synthetic gene expression perturbation systems with rapid, tunable, single-gene specificity in yeast," Nucleic acids research, vol. 41, No. 4, 10 pages, 2013.
Miura et al., "Enzyme evolution by yeast cell surface engineering", Methods in Molecular Biology, vol. 1319, pp. 217-232, 2015.
Nasmyth, "Molecular genetics of yeast mating type," Annual review of genetics, vol. 16, pp. 439-500, 1982.
Parrish, et al., "Yeast two-hybrid contributions to interactome mapping," Current opinion in biotechnology, vol. 17, pp. 387-393, 2006.
Procko, et al., "A computationally designed inhibitor of an Epstein-Barr viral Bcl-2 protein induces apoptosis in infected cells," Cell, vol. 157, pp. 1644-1656, 2014.

\* cited by examiner

FIG. 2C
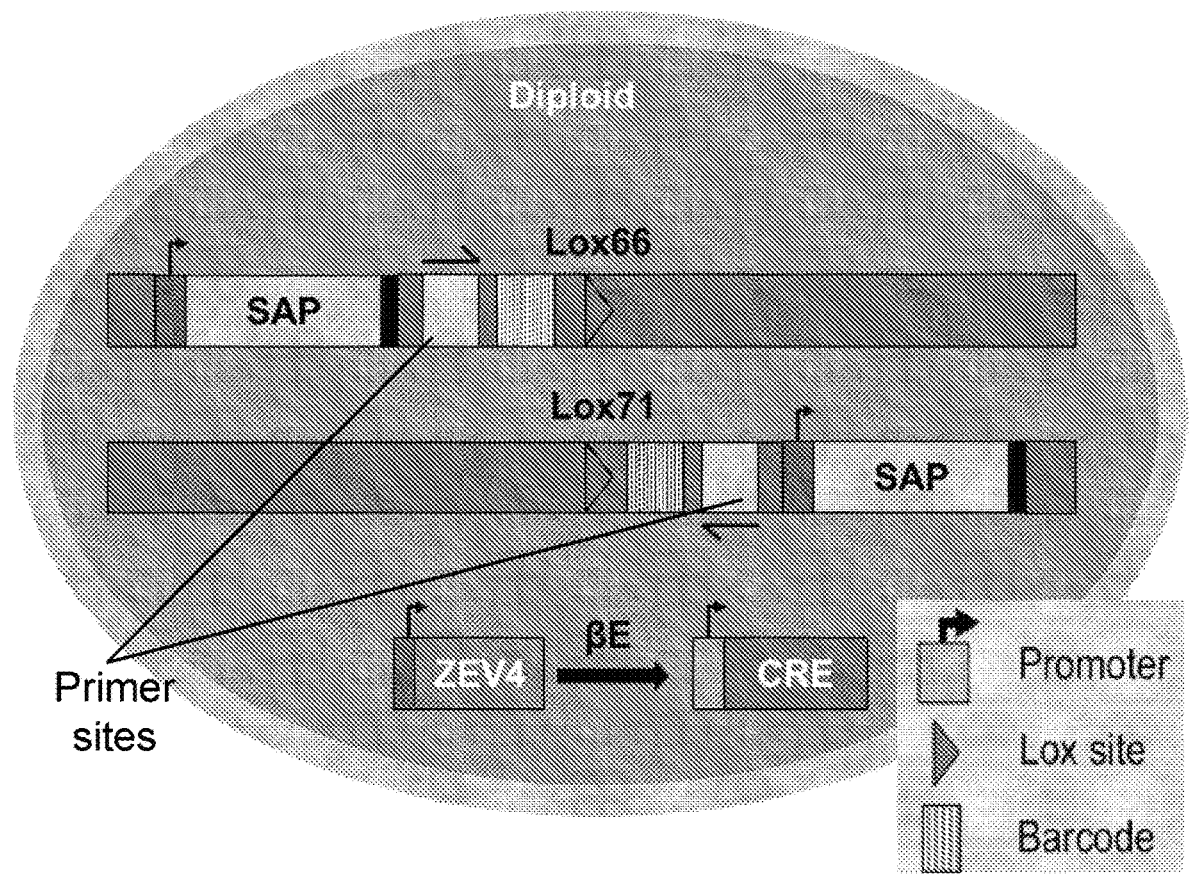
Following CRE translocation constructs are at same genomic target locus
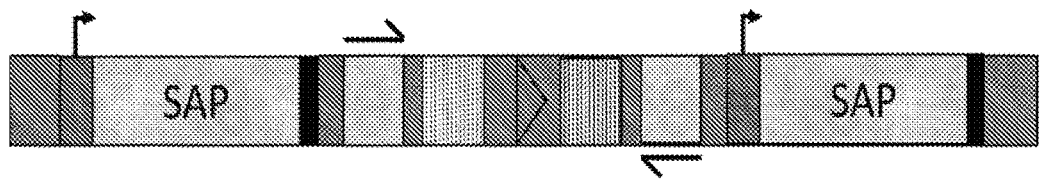
Amplify target DNA using primers to unique primer sites
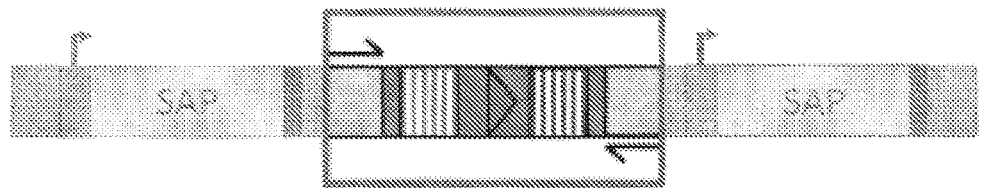

57.1%
±0.2%

0.3%
±0.5%

30.2%
±1.1%

0.1%
±0.1%

Percent diploid

FIG.11

Mating likelihood matrix
$$L = \begin{pmatrix} L_{a1/\alpha1} & L_{a2/\alpha1} & \cdots \\ L_{a1/\alpha2} & L_{a2/\alpha2} & \cdots \\ \vdots & \vdots & \end{pmatrix}$$

Haploid population percent vector
$$P_t = \begin{pmatrix} P_{a1} \\ P_{a2} \\ \vdots \\ P_{\alpha1} \\ P_{\alpha2} \\ \vdots \end{pmatrix}$$

Mating simulation matrix
$$S_t = \begin{pmatrix} (L_{a1/\alpha1})(P_{a1})(P_{\alpha1}) & (L_{a2/\alpha1})(P_{a2})(P_{\alpha1}) & \cdots \\ (L_{a1/\alpha2})(P_{a1})(P_{\alpha2}) & (L_{a2/\alpha2})(P_{a2})(P_{\alpha2}) & \cdots \\ \vdots & \vdots & \end{pmatrix}$$

Updated haploid population percent vector
$$P_{t+1} = \begin{pmatrix} \Sigma(S_{t,i=1})/\Sigma(S_t) \\ \Sigma(S_{t,i=2})/\Sigma(S_t) \\ \vdots \\ \Sigma(S_{t,j=1})/\Sigma(S_t) \\ \Sigma(S_{t,j=2})/\Sigma(S_t) \\ \vdots \end{pmatrix}$$

FIG.21
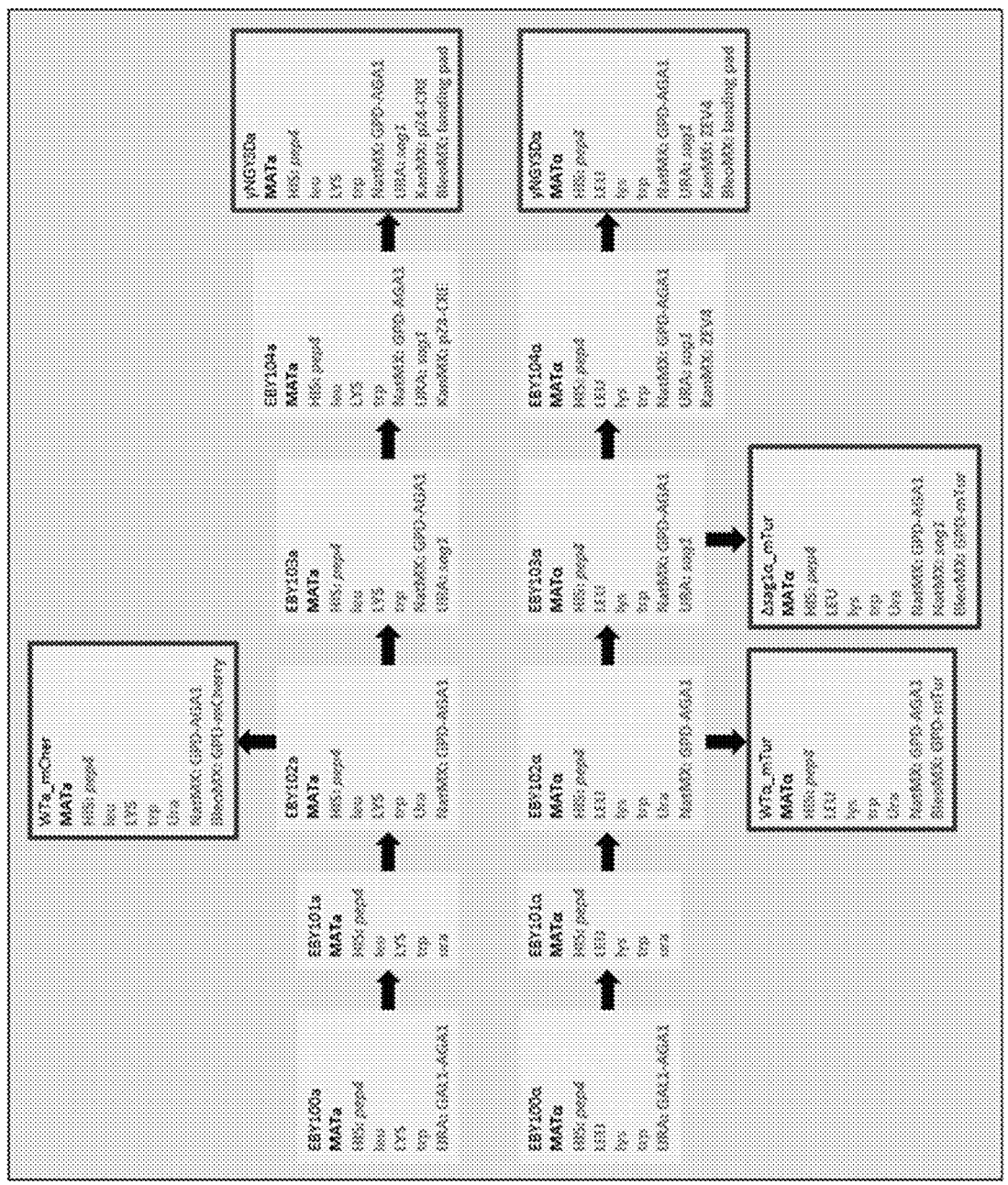
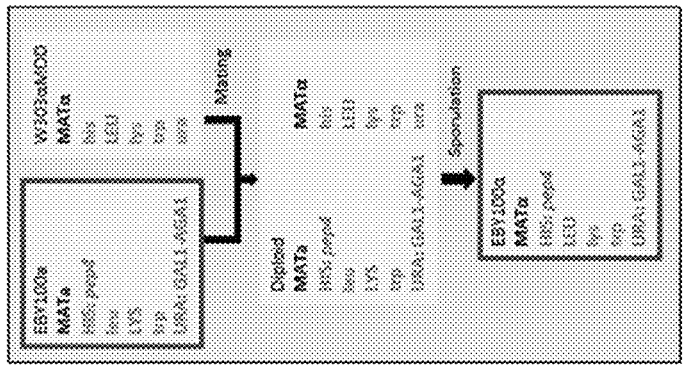

FIG. 22

Pairwise Mating Efficiency: (% diploid) MEAN

| | B+ | | B- | | | X- | | | | | | | | | |
|---|---|---|---|---|---|---|---|---|---|---|---|---|---|---|---|
| | F21 | F30D | CDP01 | B40A | 2+ | 4LVT | CDP07 | MINDI | Bim | Noxa | Puma | Bad | Bik | Hrk | Bmf |
| Bfl1 | 12.2 | 13.1 | 0.2 | 1.7 | 0.6 | 0.2 | 0.3 | 0.4 | 22.4 | 51.6 | 23.6 | 0.2 | 10.8 | 3.6 | 5.6 |
| BclB | 0.4 | 0.4 | 10.3 | 5.5 | 6.4 | 0.3 | 5.1 | 1.2 | | | | | | | |
| Bcl2 | 3.5 | 3.5 | 0.2 | 10.6 | 0.6 | 35.4 | 12.1 | 0.3 | 24.9 | 0.2 | 30.6 | 5.5 | 24.6 | 5.5 | 19.0 |
| BclXL | 2.9 | 2.2 | 0.2 | 7.9 | 0.6 | 0.7 | 8.8 | 0.2 | 19.1 | 0.2 | 19.6 | 8.7 | 5.8 | 10.9 | 9.9 |
| BclW | 0.4 | 0.3 | 0.2 | 0.6 | 0.3 | 0.6 | 7.8 | 0.2 | 12.4 | 0.3 | 8.3 | 0.7 | 5.7 | 0.5 | 3.1 |
| Mcl1 | 0.4 | 0.4 | 0.2 | 1.2 | 0.3 | 0.3 | 1.0 | 4.6 | 3.7 | 0.8 | 3.6 | 0.5 | 1.2 | 0.4 | 0.6 |

Standard Deviation

| | B+ | | B- | | | X- | | | | | | | | | |
|---|---|---|---|---|---|---|---|---|---|---|---|---|---|---|---|
| | F21 | F30D | CDP01 | B40A | 2+ | 4LVT | CDP07 | MINDI | Bim | Noxa | Puma | Bad | Bik | Hrk | Bmf |
| Bfl1 | 2.01 | 0.65 | 0.07 | 0.45 | 0.08 | 0.03 | 0.13 | 0.04 | 2.85 | 7.90 | 1.42 | 0.14 | 0.80 | 1.17 | 2.04 |
| BclB | 0.24 | 0.04 | 2.30 | 0.92 | 2.31 | 0.18 | 2.68 | 0.17 | | | | | | | |
| Bcl2 | 0.40 | 1.07 | 0.08 | 1.85 | 0.21 | 2.60 | 3.31 | 0.09 | 8.76 | 0.03 | 3.47 | 1.40 | 10.89 | 1.06 | 4.29 |
| BclXL | 0.62 | 0.04 | 0.10 | 0.52 | 0.16 | 0.45 | 2.55 | 0.07 | 8.00 | 0.07 | 5.00 | 0.20 | 1.53 | 0.97 | 2.27 |
| BclW | 0.15 | 0.06 | 0.08 | 0.36 | 0.12 | 0.25 | 0.82 | 0.05 | 2.00 | 0.05 | 1.60 | 0.24 | 1.42 | 0.10 | 0.96 |
| Mcl1 | 0.08 | 0.24 | 0.06 | 0.31 | 0.11 | 0.08 | 0.38 | 1.52 | 0.77 | 0.04 | 0.44 | 0.09 | 0.53 | 0.20 | 0.15 |

FIG.23

| Batched Mating Percent: MEAN | | | | | | |
|---|---|---|---|---|---|---|
| | Bfl1 | BclB | Bcl2 | BclXL | BclW | Mcl1 |
| F21 | 7.37 | 0.44 | 1.12 | 1.81 | 0.35 | 0.05 |
| F30D | 4.28 | 0.31 | 0.86 | 1.01 | 0.32 | 0.05 |
| B+ | 0.16 | 5.91 | 0.46 | 0.12 | 0.25 | 0.03 |
| B-CDP01 | 0.81 | 1.88 | 2.36 | 2.38 | 0.37 | 0.28 |
| B40A | 0.28 | 2.76 | 0.31 | 0.44 | 0.23 | 0.02 |
| 2+ | 0.52 | 0.45 | 27.48 | 0.63 | 0.34 | 0.06 |
| 4LVT | 0.29 | 0.30 | 15.78 | 0.32 | 0.49 | 0.04 |
| X-CDP07 | 0.29 | 0.94 | 3.76 | 7.07 | 2.70 | 0.16 |
| MINDI | 0.08 | 0.25 | 0.15 | 0.05 | 0.20 | 0.63 |
| Standard Deviation | | | | | | |
| | Bfl1 | BclB | Bcl2 | BclXL | BclW | Mcl1 |
| F21 | 2.05 | 0.32 | 0.15 | 0.84 | 0.36 | 0.04 |
| F30D | 1.08 | 0.22 | 0.08 | 0.50 | 0.36 | 0.04 |
| B+ | 0.05 | 2.29 | 0.00 | 0.02 | 0.27 | 0.03 |
| B-CDP01 | 0.38 | 1.10 | 0.64 | 1.14 | 0.12 | 0.03 |
| B40A | 0.12 | 2.39 | 0.07 | 0.36 | 0.17 | 0.00 |
| 2+ | 0.15 | 0.10 | 3.73 | 0.14 | 0.12 | 0.04 |
| 4LVT | 0.05 | 0.01 | 1.15 | 0.06 | 0.04 | 0.03 |
| X-CDP07 | 0.04 | 0.35 | 0.01 | 1.10 | 0.15 | 0.04 |
| MINDI | 0.05 | 0.08 | 0.14 | 0.02 | 0.25 | 0.28 |

FIG.24

| Batched mating percent (+BAD) | | | | | | |
|---|---|---|---|---|---|---|
| | Bfl1 | BclB | Bcl2 | BclXL | BclW | Mcl1 |
| F21 | 18.01 | 0.84 | 0.07 | 0.01 | 0.26 | 0.25 |
| F30D | 10.58 | 0.48 | 0.04 | 0.04 | 0.13 | 0.08 |
| B+ | 0.69 | 21.45 | 0.10 | 0.01 | 0.22 | 0.16 |
| B-CDP01 | 3.24 | 7.49 | 0.12 | 0.02 | 0.33 | 2.13 |
| B40A | 1.29 | 13.75 | 0.03 | 0.05 | 0.19 | 0.13 |
| 2+ | 0.13 | 0.04 | 0.55 | 0.04 | 0.32 | 0.02 |
| 4LVT | 0.11 | 0.05 | 0.20 | 0.01 | 0.63 | 0.02 |
| X-CDP07 | 0.35 | 4.02 | 0.05 | 0.06 | 5.44 | 1.09 |
| MINDI | 0.22 | 0.76 | 0.03 | 0.00 | 0.09 | 3.58 |

HIGH THROUGHPUT PROTEIN-PROTEIN INTERACTION SCREENING IN YEAST LIQUID CULTURE

CROSS REFERENCE

This application is a continuation-in-part of U.S. application Ser. No. 15/407,215 filed Jan. 16, 2017 which claims the benefit and priority of U.S. provisional patent application, Ser. No. 62/279,227, filed Jan. 15, 2016, the disclosures of which are incorporated by reference herein in their entireties.

STATEMENT REGARDING FEDERALLY SPONSORED RESEARCH

This invention was made with U.S. government support under the National Science Foundation award numbers 1317653 and DGE1256082. The U.S. Government has certain rights in the invention.

SEQUENCE LISTING

The sequence listing submitted herewith, entitled "16-1722-US-CIP Sequence-Listing ST25 txt" created on Apri. 21, 2020, and 3kb in size, is incorporated by reference in its entirety.

BACKGROUND

The mating of Saccharomyces cerevisiae is a biological phenomenon that can be utilized for many engineering applications including screening protein-protein interactions, screening drug candidates for on and off target effects, and detecting extracellular targets, and modeling reproductive ecology. Yeast mating in a turbulent liquid culture is dependent on an initial binding step, called sexual agglutination. The cell membranes of a single MATa haploid cell and a single MATalpha (MATα) haploid cell must be in direct and sustained contact in order for membrane fusion to begin, an early and critical step in the mating process. This disclosure demonstrates that there is a positive correlation between the binding strength of two cells and their mating efficiency in liquid culture. By knocking out the native mechanism for sexual agglutination and expressing arbitrary binding proteins on the surface of MATa and MATalpha haploid cells, it is possible to couple mating efficiency to the interaction strength of a particular pair of proteins. This disclosure demonstrates a yeast mating system that can be applied to at least four contexts: screening protein-protein interaction networks, screening drug candidates for their effect on both on- and off-target protein interactions, detecting extracellular targets for which no native S. cerevisiae receptor exists, and re-engineering yeast agglutination in order to answer biological questions about yeast speciation and ecological dynamics.

Wild-type S. cerevisiae cells are able to mate in both solid and liquid culture environments. On solid culture, cells of opposite mating types that are in very close proximity shmoo towards one another until they make direct contact. This "shmooing" behavior is initiated by a cell's detection of mating factor produced by a cell of the opposite mating type. Since no shear forces are present on the surface of solid media, it is unnecessary for the cells to bind strongly to one another in order to mate in this environment. In a turbulent liquid culture, however, a strong interaction between cells is essential for maintaining sustained contact. In response to the detection of factor from a cell of the opposite mating type, a haploid cell begins to express mating type specific sexual agglutinin proteins. Prior to induction, both the a- and α-agglutinins are present at $0$-$10^4$ molecules per cell. In the presence of the appropriate mating factor, the expression of the sexual agglutinins on the yeasts' surface increases to $10^4$-$10^5$ molecules per cell, which allows for the interaction of many pairs of agglutinins between two haploid cells. These proteins are responsible for the strong binding between haploid cells that leads to mating (see FIG. 1). The primary agglutination interaction is between the MATa sexual agglutinin subunit, Aga2, and the MATalpha sexual agglutinin, Sag 1. Aga1 and Sag 1 form glycosylphosphatidylinositol (GPI) anchors with the yeast cell wall and extend glycosylated stalks outside of the cell wall. Aga2 is secreted by MATa cells and forms a disulfide bond with Aga1 (see FIG. 1). At 20° C., the $K_D$ of the interaction between these two proteins is between 2 and 5 nM and multiple interactions can occur between a pair of cells. It is this strong binding interaction and high avidity that maintains cell-cell adhesion between cells of opposite mating types in a liquid culture even when strong shear forces from mixing are exerted.

It appears that the role of the sexual agglutinin proteins is limited to inducing agglutination and that they serve no other function in yeast mating. Furthermore, the coevolution of the MATa and MATalpha sexual agglutinin proteins may have been a contributing factor in the speciation of yeast. If the only role of the sexual agglutinin proteins was cell-cell adhesion, then other pairs of binding proteins, either naturally derived or engineered, that exhibit similar interaction strengths should be able to substitute for the function of the naturally occurring sexual agglutinin proteins (see FIG. 1). These synthetic agglutinin proteins (SAP) can be expressed on the surface of haploid yeast cells with yeast surface display. This approach can involve the constitutive expression or overexpression of Aga1 and an arbitrary binding protein fused to Aga2. As in wild-type S. cerevisiae, Aga1 forms a GPI anchor with the cell wall. The Aga2 fusion protein is secreted and forms a disulfide bond with Aga1, leaving the arbitrary binding protein exposed on the surface of the cell. This technique has been used to display properly folded proteins including single chain antibodies, enzymes, growth factors, and cell-surface receptors.

Synthetic agglutination with surface displayed binding proteins may be able to substitute for the function of wild-type sexual agglutinin proteins and could be used for a variety of engineering applications, such as a valuable platform for screening and evolving protein-protein interactions in a high-throughput manner. Since the interaction occurs outside of the cell, membrane soluble or insoluble compounds can be added to the media exogenously to screen potential therapeutic molecules for their on-and off-target disruption of protein interactions. Similarly, indirect protein-protein interactions that require the presence of a small molecule, a third protein, or a larger protein complex can be designed (see FIG. 1). In this system, mating efficiency would be low when the target is absent and high when the target is present. Therefore, it would be possible to use this tool to construct an arbitrary cellular sensor for any target for which two strong binders can be designed. Additionally, replacing the sexual agglutinin proteins with orthogonal binding pairs could result in an engineerable pre-zygotic barrier to mating, which could serve as a valuable platform for studying genetic isolation, speciation, and intraspecies ecosystem dynamics.

If binding strength could be coupled to mating efficiency, either through a direct protein-protein interaction or through a substrate-mediated interaction, various biological tools can be used to determine the mating efficiency or to generate some other response. For example, such a yeast mating platform can be used to answer: the relative bind interactions between each pair of synthetic agglutination proteins (i.e, binders and targets) in a given a library of binders, $[X_1, X_2, \ldots X_2, \ldots X_n]$ and a library of targets $[Y_1, Y_2, \ldots Y_n]$; if a target is present in sample (for example, if binder $X_1$ and $X_2$ interact only in the presence of target Y, is target Y present in an unknown culture); is the rate of divergent evolution affected by pre-zygotic barrier strength?

Existing approaches for experimentally screening computationally designed PPIs fail to meet the needs of many modern protein engineering challenges. For example, despite their scientific and medical relevance, no methods exist for the high throughput screening of protein interaction network design, two-sided design, or non-membrane permeable ligand mediated interaction design. Surface display techniques, such as yeast surface display, are commonly used for screening a one-sided design library but can only characterize binding against a limited number of targets per assay due to the small number of spectrally resolvable fluorescent markers. Intracellular binding assays, such as yeast two-hybrid, cannot be used to characterize dynamic interactions with non-membrane permeable or toxic ligands and suffer from the influence of host cell conditions. Recently, cell-free approaches for protein network characterization have demonstrated increased throughput by replacing fluorescent markers with DNA barcodes, but these approaches lose the advantages of genetic encoding such as rapid library construction and ease of iteration. The lack of an appropriate high throughput screening platform has caused an experimental bottleneck in which protein engineers are unable to test many potentially functional designs due to time and resource constraints.

Described herein are compositions and methods that can be used, for example, in characterizing protein-protein interaction networks, screening drug candidates for protein-protein interaction disruption, detecting extracellular targets, or understanding mating dependent biological processes such as speciation and ecosystem dynamics. Such applications utilize the same overall architecture, where native budding yeast (e.g., *S. cerevisiae*) sexual agglutinin proteins are replaced with proteins expressed with yeast surface display.

SUMMARY OF THE INVENTION

The inventors have surprisingly discovered that yeast sexual agglutination, which is a natural protein-protein interaction, can be re-engineered, so that mating in liquid culture can in certain embodiments be used to provide a high throughput screening platform for protein-protein interactions by reprogramming yeast sexual agglutination to link protein interaction strength with mating efficiency. The methods and compositions of the invention can in certain embodiments be utilized for the characterization of protein interaction networks in high-throughput for both binding affinity and specificity, which is crucial for understanding cellular functions, screening therapeutic candidates, and evaluating engineered protein networks provide.

In a first aspect, the invention provides an assay for identifying protein-protein interactions comprising:
(A) culturing a mixture of a first recombinant yeast strain integrated with a first nucleic acid construct and a second recombinant yeast strain integrated with a second nucleic acid construct for a time and under conditions resulting in:
  (1) expression in the first recombinant yeast strain of one or more first synthetic adhesion proteins (SAPs) bound to a first cell wall glycosylphosphatidylinositol (GPI) anchored protein on the surface of the first recombinant yeast strain;
  (2) expression in the second recombinant yeast strain of one or more second synthetic adhesion proteins bound to a second cell wall GPI anchored protein on the surface of the second recombinant yeast strain;
  (3) formation of protein-protein interactions between the one or more first SAPs bound to the first cell wall GPI anchored protein and the one or more second SAPs bound to the second cell wall GPI anchored protein, such that mating can occur between the first recombinant yeast strain and the second recombinant yeast strain wherein:
    (a) one or both of the first recombinant yeast strain and the second recombinant yeast strain comprises an exogenous recombinase;
    (b) one or both of the first recombinant yeast strain and the second recombinant yeast strain does not express at least one native sexual agglutination protein;
    (c) the first nucleic acid construct comprises:
      (i) a homology arm at the 5' end of the nucleic acid construct,
      (ii) a first expression cassette comprising a gene coding for the first SAP,
      (iii) a second expression cassette comprising a first marker,
      (iv) a unique primer binding site,
      (v) a unique nucleic acid barcode,
      (vi) a recombination site, and
      (vii) a homology arm at the 3' end of the nucleic acid construct; and
    (d) the second nucleic acid construct comprises:
      (i) a homology arm at the 5' end of the nucleic acid construct,
      (ii) a first expression cassette comprising a gene coding for the second SAP,
      (iii) a second expression cassette comprising a first marker,
      (iv) a unique primer binding site,
      (v) a unique nucleic acid barcode,
      (vi) a recombination site, and
      (vii) a homology arm at the 3' end of the nucleic acid construct; and
(B) determining the percentage of diploid yeast cells from the mixture wherein diploid cells indicate a protein-protein interaction between the first SAP and the second SAP.

In some embodiments of the assay, the first and second recombinant yeast strains are budding yeast selected from *Pichia pastoris* and *Saccharomyces cerevisiae*. In another embodiment, the first recombinant yeast strain is a MATa yeast strain and the second recombinant yeast strain is a MATalpha yeast strain. In yet another embodiment, the first recombinant yeast strain comprises a selection marker, and the second recombinant yeast strain comprises a selection marker; wherein the selection marker of the first recombinant yeast strain is different than the selection marker of the second recombinant yeast strain. In some embodiments, the selection marker is an auxotrophic marker. In certain embodiments, the one or both of the first recombinant yeast strain and the second recombinant yeast strain expresses the cell wall GPI anchored protein Aga1. In another embodiment, one or both of the first recombinant yeast strain and the second recombinant yeast strain does not express the native sexual agglutination protein Sag 1.

In certain embodiments of the assay, the first SAP is fused to the sexual agglutination protein Aga2, and the second SAP is fused to the sexual agglutination protein Aga2; wherein the culturing time and conditions allow binding of Aga2 to Aga1. In an embodiment, the binding of Aga2 to Aga1 is by at least one disulfide bond. In some embodiments, both the first recombinant yeast strain and the second recombinant yeast strain comprise a selection marker. In yet another embodiment, the first nucleic construct and the second nucleic acid construct both comprise a third expression cassette comprising a second marker, wherein the second marker is a fluorescent marker. In some embodiments, the fluorescent marker of the first nucleic acid construct is different than the fluorescent marker of the second nucleic acid construct.

In an embodiment of the assay, the gene coding for the first SAP is assayed for binding to the gene coding for the second SAP, wherein determining the percentage of diploid yeast cells from the mixture wherein diploid cells indicates a protein-protein interaction between the first SAP and the second SAP and wherein the percentage of diploid cells is determined using flow cytometry.

In another embodiment of the assay, the gene coding for the first SAP is assayed for binding to a library of genes coding for the second SAP; wherein the protein-protein interaction is determined by:
 (a) isolating genomic DNA from the mixture of yeast strains;
 (b) amplifying a target DNA sequence using primers specific for the unique primer bind sites in the first and second nucleic acid constructs to generate the target DNA sequence;
 (c) sequencing the target DNA sequence to determine the protein-protein interaction.

In yet another embodiment of the assay, a library of genes coding for the first SAP is assayed for binding to a library of genes coding for the second SAP, wherein the protein-protein interaction is determined by:
 (a) isolating genomic DNA from the mixture of yeast strains;
 (b) amplifying a target DNA sequence using primers specific for the unique primer bind sites in the first and second nucleic acid constructs to generate the target DNA sequence;
 (c) sequencing the target DNA sequence to determine the protein-protein interaction.

In certain embodiments, nucleic acid plasmids carrying the SAPs of the invention can be transformed into the yeast strains. In such an embodiment, the nucleic acid plasmids can be for example, 2 micron or centromeric plasmids, that are not integrated into the genome.

In a second aspect, the invention provides a kit comprising:
 (a) a first recombinant yeast strain and a second recombinant yeast strain, wherein one or both of the first recombinant yeast strain and the second recombinant yeast strain comprises an exogenous recombinase, and one or both of the first recombinant yeast strain and the second recombinant yeast strain does not express at least one native sexual agglutination protein;
 (b) a first nucleic acid construct comprising:
 a homology arm at the 5' end of the nucleic acid construct,
 (ii) a first expression cassette comprising a gene coding for the first SAP,
 (iii) a second expression cassette comprising a first marker,
 (iv) a unique primer binding site,
 (v) a unique nucleic acid barcode,
 (vi) a recombination site, and
 (vii) a homology arm at the 3' end of the nucleic acid construct; and
 (c) a second nucleic acid construct comprising:
 (i) a homology arm at the 5' end of the nucleic acid construct,
 (ii) a first expression cassette comprising a gene coding for the second SAP,
 (iii) a second expression cassette comprising a first marker,
 (iv) a unique primer binding site,
 (v) a unique nucleic acid barcode,
 (vi) a recombination site, and
 (vii) a homology arm at the 3' end of the nucleic acid construct.

In a third aspect, the invention provides a composition selected from the group consisting of:
 (a) a first recombinant yeast strain and a second recombinant yeast strain, wherein one or both of the first recombinant yeast strain and the second recombinant yeast strain comprises an exogenous recombinase, and one or both of the first recombinant yeast strain and the second recombinant yeast strain does not express at least one native sexual agglutination protein;
 (b) a first nucleic acid construct comprising:
 (i) a homology arm at the 5' end of the nucleic acid construct,
 (ii) a first expression cassette comprising a gene coding for the first SAP,
 (iii) a second expression cassette comprising a first marker,
 (iv) a unique primer binding site,
 (v) a unique nucleic acid barcode,
 (vi) a recombination site, and
 (vii) a homology arm at the 3' end of the nucleic acid construct; and
 (c) a second nucleic acid construct comprising;
 (i) a homology arm at the 5' end of the nucleic acid construct,
 (ii) a first expression cassette comprising a gene coding for the second SAP,
 (iii) a second expression cassette comprising a first marker,
 (iv) a unique primer binding site,
 (v) a unique nucleic acid barcode,
 (vi) a recombination site, and
 (vii) a homology arm at the 3' end of the nucleic acid construct.

In certain embodiments of the composition, the first recombinant yeast strain comprises an exogenous recombinase regulated by an inducible promoter, the second recombinant yeast strain comprises an exogenous recombinase regulated by an inducible promoter or both the first recombinant yeast strain and the second recombinant yeast strain comprises an exogenous recombinase regulated by an inducible promoter.

In another embodiment of the composition, the first nucleic acid construct comprises a third expression cassette comprising a second marker and the second nucleic acid construct comprises a third expression cassette comprising a second marker.

In yet another embodiment of the composition, wherein the first nucleic acid construct is part of a first vector comprising a high copy origin of replication and a resistance gene, and the second nucleic acid construct is part of a recombinant vector comprising a high copy origin of replication and a resistance gene.

In a fourth aspect, the invention provides a method for detecting a protein-protein interaction between cell surface proteins, the method comprising:

(a) providing a first plurality of haploid yeast cells of a first mating type, the first plurality of cells comprising a library of first gene expression cassettes, wherein each gene expression cassette in the library comprises:
  a first selectable marker, a first unique oligonucleotide molecular barcode sequence operatively linked to a first recombination site, and a sequence encoding a unique cell surface protein, such that each unique molecular barcode is associated with a unique cell surface protein;

(b) providing a second plurality of haploid yeast cells of a second mating type, the second plurality of cells comprising a library of second gene expression cassettes, wherein each gene expression cassette in the library comprises:
  a second selectable marker, a second unique oligonucleotide molecular barcode sequence operatively linked to a second recombination site, and a sequence encoding a unique cell surface protein, such that each unique molecular barcode is associated with a unique cell surface protein,
  wherein the unique cell surface proteins of the library of first gene expression cassettes and the unique cell surface proteins of the library of second gene expression cassettes comprise potential binding pairs;

(c) contacting the first plurality of haploid yeast cells with the second plurality of haploid yeast cells under yeast cell conditions that promote contact between the first plurality of haploid yeast cells and the second plurality of haploid yeast cells when a specific binding interaction between a cell surface protein of the library of first gene expression cassettes and a cell surface protein of the library of gene expression cassettes occurs, wherein the specific binding interaction promotes mating of the first and second plurality of haploid yeast cells to produce diploid yeast cells;

(d) recombining within the diploid cells portions of the gene expression cassettes to generate a recombined molecular barcode sequence comprising at least a portion of the unique barcode associated with one of the unique cell surface proteins of the library of first gene expression cassettes and a portion of the unique molecular barcode associated with one of the unique cell surface proteins of the library of second gene expression cassettes; and (e) sequencing at least a portion of the recombined molecular barcode sequence from the diploid cells to identify a surface protein from the library of first gene expression cassettes and a cell surface protein from the library of second gene expression cassettes that interact, thus detecting a protein-protein interaction between the cell surface proteins.

In some embodiments of the method, the library of first gene expression cassettes is carried by a library of first plasmids, the library of second gene expression cassettes is carried by a library of second plasmids, and the yeast cell conditions that promote contact between the first plurality of haploid yeast cells and the second plurality of haploid yeast cells are dilute yeast cell conditions. In another embodiment, at least one of the selectable markers is used to select for diploid cells that contain at least one each of the first and second plasmids after contacting the first plurality of haploid yeast cells with the second plurality of haploid yeast cells. In yet another embodiment, the recombined molecular barcode sequence from two or more diploid cells are sequenced to detect two or more different cell surface protein-protein interactions. In some embodiments, the specific binding interaction between the first plurality of haploid yeast cells and the second plurality of haploid yeast cells occurs in a dilute mixture that has a spectral absorbance of less than 2.0 O.D. 600 nm. In another embodiment, the binding affinity between the first cell surface protein and the second cell surface protein is greater than the mating type binding affinity between a yeast cell from the first mating type and a yeast cell from the second mating type. In yet another embodiment, the binding affinity is at least two-fold, five-fold or ten-fold greater than the mating type affinity.

In some embodiments of the method, the first selectable marker and the second selectable marker are the same. In another embodiment, the first selectable marker and the second selectable marker are different. In another embodiment, the recombination is site-specific recombination, or further, CRE-lox recombination. In yet another embodiment, the first and the second unique oligonucleotide molecular barcode sequence is between 5 and 50 nucleotides in length.

In some embodiments of the method, the plasmids recombine with the genome of the haploid yeast cell or the diploid yeast cell. In another embodiment, the cell surface protein is a transmembrane protein, integral membrane protein, peripheral membrane protein, is encoded by a mammalian gene, or is encoded by a human gene. In yet another embodiment, mating of the haploid yeast cells is detected by a marker that becomes active only in the diploid cells. In some embodiments, the diploid cells are detected after recombination between the plasmids.

In certain embodiments of the method, the diploid cells are detected by the presence of two distinct selectable markers. In another embodiment, sequencing comprises amplification of the recombined molecular barcode sequence. In yet another embodiment, sequencing comprises amplification of at least a portion of the sequence that encodes the cell surface protein in a first plasmid or at least a portion of the sequence that encodes the cell surface protein in a second plasmid. In an embodiment, the cell surface protein is a protein not normally associated with the cell membrane or expressed on the cell surface. In yet another embodiment, the cell surface protein is a hybrid protein comprising at least a portion of a native, soluble protein fused to at least a portion of a native cell surface protein, wherein the at least a portion of the native, soluble protein is expressed on the outer surface of the haploid yeast cell. In another embodiment, a linker connects the at least a portion of the native, soluble protein to the at least a portion of the native cell surface protein.

In an embodiment of the method, the gene expression cassettes are integrated into the genome of the haploid yeast cell or the diploid yeast cell. In another embodiment, the gene expression cassettes are carried by a 2 micron plasmid and are not integrated into the genome of the haploid yeast cell or the diploid yeast cell. In yet another embodiment, the gene expression cassettes are carried by a centromeric plasmid and are not integrated into the genome of the haploid yeast cell or the diploid yeast cell.

The present disclosure provides the following non-limiting numbered embodiments:

Embodiment 1: An assay for identifying protein-protein interactions comprising:
(A) culturing a mixture of a first recombinant yeast strain integrated with a first nucleic acid construct and a second recombinant yeast strain integrated with a second nucleic acid construct for a time and under conditions resulting in:
  (1) expression in the first recombinant yeast strain of one or more first synthetic adhesion proteins (SAPs) bound to a first cell wall glycosylphosphatidylinositol (GPI) anchored protein on the surface of the first recombinant yeast strain;
  (2) expression in the second recombinant yeast strain of one or more second synthetic adhesion proteins bound to a second cell wall GPI anchored protein on the surface of the second recombinant yeast strain;
  (3) formation of protein-protein interactions between the one or more first SAPs bound to the first cell wall GPI anchored protein and the one or more second SAPs bound to the second cell wall GPI anchored protein, such that mating can occur between the first recombinant yeast strain and the second recombinant yeast strain wherein:
    (a) one or both of the first recombinant yeast strain and the second recombinant yeast strain comprises an exogenous recombinase;
    (b) one or both of the first recombinant yeast strain and the second recombinant yeast strain does not express at least one native sexual agglutination protein;
    (c) the first nucleic acid construct comprises:
      (i) a homology arm at the 5' end of the nucleic acid construct,
      (ii) a first expression cassette comprising a gene coding for the first SAP,
      (iii) a second expression cassette comprising a first marker,
      (iv) a unique primer binding site,
      (v) a unique nucleic acid barcode,
      (vi) a recombination site, and
      (vii) a homology arm at the 3' end of the nucleic acid construct; and
    (d) the second nucleic acid construct comprises:
      (i) a homology arm at the 5' end of the nucleic acid construct,
      (ii) a first expression cassette comprising a gene coding for the second SAP,
      (iii) a second expression cassette comprising a first marker,
      (iv) a unique primer binding site,
      (v) a unique nucleic acid barcode,
      (vi) a recombination site, and
      (vii) a homology arm at the 3' end of the nucleic acid construct; and
(B) determining the percentage of diploid yeast cells from the mixture wherein diploid cells indicate a protein-protein interaction between the first SAP and the second SAP.

Embodiment 2: The assay of embodiment 1, wherein the first and second recombinant yeast strains are budding yeast.

Embodiment 3: The assay of embodiment 2, wherein the budding yeast is *Pichia pastoris* or *Saccharomyces cerevisiae*.

Embodiment 4: The assay of embodiment 1, wherein the first recombinant yeast strain is a MATa yeast strain and the second recombinant yeast strain is a MATalpha yeast strain.

Embodiment 4a: The assay of embodiment 1, wherein the first recombinant yeast strain is a MATalpha yeast strain and the second recombinant yeast strain is a MATa yeast strain.

Embodiment 5: The assay of embodiment 1, wherein the first recombinant yeast strain comprises a selection marker, and the second recombinant yeast strain comprises a selection marker; wherein the selection marker of the first recombinant yeast strain is different than the selection marker of the second recombinant yeast strain.

Embodiment 5a: The assay of embodiment 5, wherein the selection marker is an auxotrophic marker or an antibacterial marker.

Embodiment 6: The assay of embodiment 1, wherein one or both of the first recombinant yeast strain and the second recombinant yeast strain expresses the cell wall GPI anchored protein Aga1.

Embodiment 7: The assay of embodiment 1, wherein one or both of the first recombinant yeast strain and the second recombinant yeast strain does not express the native sexual agglutination protein Sag 1.

Embodiment 8: The assay of embodiment 1, wherein the first SAP is fused to Aga2, and the second SAP is fused to Aga2; wherein the culturing time and conditions allow binding of Aga2 to Aga1.

Embodiment 9: The assay of embodiment 1, wherein both the first recombinant yeast strain and the second recombinant yeast strain comprise a selection marker.

Embodiment 10: The assay of embodiment 9, wherein the selection marker is an auxotrophic marker or an antibiotic marker.

Embodiment 11: The assay of embodiment 10, wherein the selection marker is an auxotrophic marker.

Embodiment 12: The assay of embodiment 11, wherein the auxotrophic marker is ADE1, ADE2, CAN1, HIS3, LEU2, LYS2, TRP1, TRPS, URA3 or URA4.

Embodiment 13: The assay of embodiment 10, wherein the selection marker is an antibiotic resistance marker.

Embodiment 14: The assay of embodiment 13, wherein the antibiotic resistance marker provides resistance to geneticin, nourseothricin, bleomycin, hygromycin, phleomycin, zeocin or canavanine.

Embodiment 15: The assay of embodiment 1, wherein the first nucleic construct comprises a third expression cassette comprising a second marker.

Embodiment 16: The assay of embodiment 15, wherein the second marker is a fluorescent marker.

Embodiment 17: The assay of embodiment 1, wherein the second nucleic acid construct comprises a third expression cassette comprising a second marker.

Embodiment 18: The assay of embodiment 17, wherein the second marker is a fluorescent marker.

Embodiment 19: The assay of embodiment 18, wherein the fluorescent marker of the first nucleic acid construct is different than the fluorescent marker of the second nucleic acid construct.

Embodiment 20: The assay of embodiment 1, wherein the percentage of diploid cells is determined using flow cytometry.

Embodiment 21: The assay of embodiment 1, wherein the first SAP is assayed for binding to a library of genes coding for the second SAP, wherein the protein-protein interaction is determined by:
  (a) isolating genomic DNA from the mixture of yeast strains;

(b) amplifying a target DNA sequence using primers specific for the unique primer bind sites in the first and second nucleic acid constructs to generate the target DNA sequence;

(c) sequencing the target DNA sequence to determine the protein-protein interaction.

Embodiment 22: The assay of embodiment 1, wherein the first SAP is encoded by a library of genes and the first SAP is assayed for binding to a library of genes coding for the second SAP, wherein the protein-protein interaction is determined by:

(a) isolating genomic DNA from the mixture of yeast strains;

(b) amplifying a target DNA sequence using primers specific for the unique primer bind sites in the first and second nucleic acid constructs to generate the target DNA sequence;

(c) sequencing the target DNA sequence to determine the protein-protein interaction.

Embodiment 23: The assay of embodiment 22, wherein the assay further comprises culturing the mixture of the first recombinant yeast strain and the second recombinant yeast strain in the presence of a modulator of protein-protein interactions.

Embodiment 24: The assay of embodiment 23, wherein the modulator of protein-protein interactions is a small molecule, a polypeptide, a nucleic acid, or an environmental factor.

Embodiment 25: A kit comprising:

(a) a first recombinant yeast strain and a second recombinant yeast strain, wherein one or both of the first recombinant yeast strain and the second recombinant yeast strain comprises an exogenous recombinase, and one or both of the first recombinant yeast strain and the second recombinant yeast strain does not express at least one native sexual agglutination protein;

(b) a first nucleic acid construct comprising:
(i) a homology arm at the 5' end of the nucleic acid construct,
(ii) a first expression cassette comprising a gene coding for the first SAP,
(iii) a second expression cassette comprising a first marker,
(iv) a unique primer binding site,
(v) a unique nucleic acid barcode,
(vi) a recombination site, and
(vii) a homology arm at the 3' end of the nucleic acid construct; and (c) a second nucleic acid construct comprising:
(i) a homology arm at the 5' end of the nucleic acid construct,
(ii) a first expression cassette comprising a gene coding for the second SAP,
(iii) a second expression cassette comprising a first marker,
(iv) a unique primer binding site,
(v) a unique nucleic acid barcode,
(vi) a recombination site, and
(vii) a homology arm at the 3' end of the nucleic acid construct.

Embodiment 26: The kit of embodiment 25, wherein the first and second recombinant yeast strains are budding yeast.

Embodiment 27: The kit of embodiment 26, wherein the budding yeast is Pichia pastoris or Saccharomyces cerevisiae.

Embodiment 28: The kit of embodiment 25, wherein the first recombinant yeast strain is a MATa yeast strain and the second recombinant yeast strain is a MATalpha yeast strain.

Embodiment 29: The kit of embodiment 25, wherein the first recombinant yeast strain comprises a selection marker and the second recombinant yeast strain comprises a selection marker; wherein the selection marker of the first recombinant yeast strain is different than the selection marker of the second recombinant yeast strain.

Embodiment 29a: The kit of embodiment 29, wherein the selection marker is an auxotrophic marker or an antibiotic marker.

Embodiment 30: The kit of embodiment 25, wherein one or both of the first recombinant yeast strain and the second recombinant yeast strain expresses the cell wall GPI anchored protein Aga1.

Embodiment 31: The kit of embodiment 25, wherein the second recombinant yeast strain does not express the native sexual agglutination protein Sag1.

Embodiment 32: The kit of embodiment 25, wherein the first SAP is fused to Aga2, and the second SAP is fused to Aga2; wherein Aga2 and Aga1 form a disulfide bond.

Embodiment 33: The kit of embodiment 25, wherein both the first recombinant yeast strain and the second recombinant yeast strain comprise a selection marker.

Embodiment 34: The kit of embodiment 33, wherein the selection marker is an auxotrophic marker or an antibiotic marker.

Embodiment 35: The kit of embodiment 34, wherein the selection marker is an auxotrophic marker.

Embodiment 36: The kit of embodiment 35, wherein the auxotrophic marker is ADE1, ADE2, CAN1, HIS3, LEU2, LYS2, TRP1, TRPS, URA3 or URA4.

Embodiment 37: The kit of embodiment 34, wherein the selection marker is an antibiotic resistance marker.

Embodiment 38: The kit of embodiment 37, wherein the antibiotic resistance marker provides resistance to geneticin, nourseothricin, bleomycin, hygromycin, phleomycin, zeocin or canavanine.

Embodiment 39: The kit of embodiment 25, wherein the first nucleic construct comprises a third expression cassette comprising a second marker.

Embodiment 40: The kit of embodiment 39, wherein the second marker is a fluorescent marker.

Embodiment 41: The kit of embodiment 25, wherein the second nucleic acid construct comprises a third expression cassette comprising a second marker.

Embodiment 42: The kit of embodiment 41, wherein the second marker is a fluorescent marker.

Embodiment 43: The kit of embodiment 42, wherein the fluorescent marker of the first nucleic acid construct is different than the fluorescent marker of the second nucleic acid construct.

Embodiment 44: The kit of embodiment 25, wherein the kit comprises instructions to carry out insertion of the synthetic adhesion proteins into the first expression cassette of both the first and second nucleic acid constructs.

Embodiment 45: The kit of embodiment 25, wherein the kit comprises instructions to carry out a screen of a library of synthetic adhesion proteins in order to determine binding between two or more of the synthetic adhesion proteins in the library.

Embodiment 46: The kit of embodiment 25, wherein the first and second nucleic acid constructs are each part of separate vectors.

Embodiment 47: A recombinant MATa yeast strain that overexpresses Aga1.

Embodiment 47a: The recombinant MATa yeast strain of embodiment 47, wherein the recombinant MATa yeast strain does not express at least one native sexual agglutination protein.

Embodiment 48: The recombinant MATa yeast strain of embodiment 47, wherein the recombinant MATa yeast strain does not express the native sexual agglutination protein Aga2.

Embodiment 49: The recombinant MATa yeast strain of embodiment 47, wherein the recombinant MATa yeast strain constitutively overexpresses Aga1 or inducibly overexpresses Aga1.

Embodiment 50: The recombinant MATa yeast strain of embodiment 49, wherein the recombinant MATa yeast strain constitutively overexpresses Aga1 and the constitutive overexpression of Aga1 is regulated by a constitutively active promoter.

Embodiment 51: The recombinant MATa yeast strain of embodiment 50, wherein the constitutively active promoter is ADH1 promoter, ADH2 promoter, ADH3 promoter, ADH4 promoter, ADH5 promoter, GAPDH1 promoter, GAPDH2 promoter, TEF1 promoter, TEF2 promoter, YEF3 promoter, CAM1 promoter, TEF4 promoter, EFB1 promoter, LEU promoter, PHO3 promoter, PHO5 promoter, PyK promoter, HIS4 promoter, CUP1 promoter, or ACO1.

Embodiment 52: The recombinant MATa yeast strain of embodiment 49, whe4rein the recombinant MATa yeast strain inducibly overexpresses Aga1 and the inducible overexpression of Aga1 is regulated by an inducible promoter.

Embodiment 53: The recombinant MATa yeast strain of embodiment 52, wherein the inducible promoter is GAL1 promoter, GAL2 promoter, GAL3 promoter, GAL4 promoter, GAL80 promoter, AOX promoter, FDH promoter PGK promoter or FLD1 promoter.

Embodiment 54: The recombinant MATa yeast strain of embodiment 47, wherein the recombinant MATa yeast strain is a budding yeast.

Embodiment 55: The recombinant MATa yeast strain of embodiment 54, wherein the budding yeast is *Pichia pastoris* or *Saccharomyces cerevisiae*.

Embodiment 56: The recombinant MATa yeast strain of embodiment 47, wherein the recombinant MATa yeast strain comprises an exogenous recombinase.

Embodiment 57: The recombinant MATa yeast strain of embodiment 56, wherein the recombinant MATa yeast strain inducibly express the exogenous recombinase.

Embodiment 58: The recombinant MATa yeast strain of embodiment 57, wherein the inducible expression of the exogenous recombinase is regulated by a transcription factor, and wherein the transcription factor is constitutively expressed in the MATalpha yeast strain and requires an additional molecule to activate expression from the inducible promoter.

Embodiment 59: The recombinant MATa yeast strain of embodiment 56, wherein the recombinase is CRE recombinase.

Embodiment 60: The recombinant MATa yeast strain of embodiment 47, wherein the recombinant MATa yeast strain comprises at least one selection marker.

Embodiment 61: The recombinant MATa yeast strain of embodiment 60, wherein the selection marker is an auxotrophic marker or an antibiotic marker.

Embodiment 62: The recombinant MATa yeast strain of embodiment 61, wherein the selection marker is an auxotrophic marker.

Embodiment 63: The recombinant MATa yeast strain of embodiment 62, wherein the auxotrophic marker is ADE1, ADE2, CAN1, HIS3, LEU2, LYS2, TRP1, TRP5, URA3 or URA4.

Embodiment 64: The recombinant MATa yeast strain of embodiment 61, wherein the selection marker is an antibiotic resistance marker.

Embodiment 65: The recombinant MATa yeast strain of embodiment 64, wherein the antibiotic resistance marker provides resistance to geneticin, nourseothricin, bleomycin, hygromycin, phleomycin, zeocin or canavanine.

Embodiment 66: The recombinant MATa yeast strain of embodiment 61, wherein the selection marker of the recombinant MATa yeast strain is different than the selection marker of the recombinant MATalpha yeast strain.

Embodiment 67: The recombinant MATa yeast strain of embodiment 47, wherein endogenous Aga1 is replaced with exogenous Aga1 regulated by a constitutively active promoter or an inducible promoter.

Embodiment 68: A recombinant MATalpha yeast strain that overexpresses Aga1 and does not express the native sexual agglutination protein Sag1.

Embodiment 69: The recombinant MATalpha yeast strain of embodiment 68, wherein the recombinant MATalpha yeast strain constitutively overexpresses Aga1 or inducibly overexpresses Aga1.

Embodiment 70: The recombinant MATalpha yeast strain of embodiment 69, wherein the recombinant MATalpha yeast strain constitutively overexpresses Aga1 and the constitutive overexpression of Aga1 is regulated by a constitutively active promoter.

Embodiment 71: The recombinant MATalpha yeast strain of embodiment 70, wherein the constitutively active promoter is ADH1 promoter, ADH2 promoter, ADH3 promoter, ADH4 promoter, ADH5 promoter, GAPDH1 promoter, GAPDH2 promoter, TEF1 promoter, TEF2 promoter, YEF3 promoter, CAM1 promoter, TEF4 promoter, EFB1 promoter, LEU promoter, PHO3 promoter, PHO5 promoter, PyK promoter, HIS4 promoter, CUP1 promoter, or ACO1.

Embodiment 72: The recombinant MATalpha yeast strain of embodiment 68, wherein the recombinant MATalpha yeast strain inducibly overexpresses Aga1 and the inducible overexpression of Aga1 is regulated by an inducible promoter.

Embodiment 73: The recombinant MATalpha yeast strain of embodiment 72, wherein the inducible promoter is GAL1 promoter, GAL2 promoter, GAL3 promoter, GAL4 promoter, GAL80 promoter, AOX promoter, FDH promoter PGK promoter or FLD1 promoter.

Embodiment 74: The recombinant MATalpha yeast strain of embodiment 68, wherein the recombinant MATalpha yeast strain is a budding yeast.

Embodiment 75: The recombinant MATalpha yeast strain of embodiment 74, wherein the budding yeast is *Pichia pastoris* or *Saccharomyces cerevisiae*.

Embodiment 76: The recombinant MATalpha yeast strain of embodiment 68, wherein the recombinant MATalpha yeast strain comprises an exogenous recombinase.

Embodiment 77: The recombinant MATalpha yeast strain of embodiment 76, wherein the recombinant MATalpha yeast strain inducibly express the exogenous recombinase.

Embodiment 78: The recombinant MATalpha yeast strain of embodiment 77, wherein the inducible expression of the exogenous recombinase is regulated by a transcription factor, and wherein the transcription factor is constitutively expressed in the MATa yeast strain and requires an additional molecule to activate expression from the inducible promoter.

Embodiment 79: The recombinant MATalpha yeast strain of embodiment 76, wherein the recombinase is CRE recombinase.

Embodiment 80: The recombinant MATalpha yeast strain of embodiment 68, wherein the recombinant MATalpha yeast strain comprises at least one selection marker.

Embodiment 81: The recombinant MATalpha yeast strain of embodiment 80, wherein the selection marker is an auxotrophic marker or an antibiotic marker.

Embodiment 82: The recombinant MATalpha yeast strain of embodiment 81, wherein the selection marker is an auxotrophic marker.

Embodiment 83: The recombinant MATalpha yeast strain of embodiment 82, wherein the auxotrophic marker is ADE1, ADE2, CAN1, HIS3, LEU2, LYS2, TRP1, TRPS, URA3 or URA4.

Embodiment 84: The recombinant MATalpha yeast strain of embodiment 81, wherein the selection marker is an antibiotic resistance marker.

Embodiment 85: The recombinant MATalpha yeast strain of embodiment 84, wherein the antibiotic resistance marker provides resistance to geneticin, nourseothricin, bleomycin, hygromycin, phleomycin, zeocin or canavanine.

Embodiment 86: The recombinant MATalpha yeast strain of embodiment 85, wherein the selection marker of the recombinant MATalpha yeast strain is different than the selection marker of the recombinant MATa yeast strain.

Embodiment 87: The recombinant MATalpha yeast strain of embodiment 68, wherein endogenous Aga1 is replaced with exogenous Aga1 regulated by a constitutively active promoter or an inducible promoter.

Embodiment 88: A first nucleic acid construct comprising:
(i) a homology arm at the 5' end of the nucleic acid construct,
(ii) a first expression cassette comprising a gene coding for the a SAP,
(iii) a second expression cassette comprising a first marker,
(iv) a unique primer binding site,
(v) a unique nucleic acid barcode,
(vi) a recombination site, and
(vii) a homology arm at the 3' end of the nucleic acid construct.

Embodiment 89: The first nucleic acid construct of embodiment 88, wherein the first marker is an auxotrophic marker or an antibiotic marker.

Embodiment 90: The first nucleic acid construct of embodiment 88, wherein the first nucleic yeast cassette comprises a third expression cassette comprising a second marker.

Embodiment 91: The first nucleic acid construct of embodiment 90, wherein the second marker is a fluorescent marker.

Embodiment 92: The first nucleic acid construct of embodiment 88, wherein the first nucleic acid construct is integrated into the genome of a recombinant MATa yeast strain.

Embodiment 93: The first nucleic acid construct of embodiment 88, wherein the 5' and 3' homology arms of the nucleic acid construct facilitate homologous pairing between the nucleic acid construct and a genomic target region resulting in the nucleic acid construct being introduced into the genomic target region.

Embodiment 94: The first nucleic acid construct of embodiment 88, wherein the first SAP binds to a cell wall GPI anchored protein.

Embodiment 94a: The first nucleic acid construct of embodiment 94, where the SAP is fused to a protein that binds to a cell wall GPI anchored protein.

Embodiment 95: The first nucleic acid construct of embodiment 88, wherein the unique barcode is specific to the synthetic adhesion protein of the expression cassette.

Embodiment 96: The first nucleic acid construct of embodiment 88, wherein the recombination site is a lox site.

Embodiment 97: The first nucleic acid construct of embodiment 96, wherein the lox site is loxP, lox66, lox71, lox511, lox5171, lox2272, M2, M3, M7, or M11.

Embodiment 98: A vector comprising the first nucleic acid construct of embodiment 88, wherein the vector comprises a high copy origin of replication and a resistance gene.

Embodiment 99: A second nucleic acid construct comprising;
a homology arm at the 5' end of the nucleic acid construct,
(ii) a first expression cassette comprising a gene coding for a second SAP,
(iii) a second expression cassette comprising a first marker,
(iv) a unique primer binding site,
(v) a unique nucleic acid barcode,
(vi) a recombination site, and
(vii) a homology arm at the 3' end of the nucleic acid construct.

Embodiment 100: The second nucleic acid construct of embodiment 99, wherein the first marker is an auxotrophic marker or an antibiotic marker.

Embodiment 101: The second nucleic acid construct of embodiment 99, wherein the second nucleic construct comprises a third expression cassette comprising a second marker.

Embodiment 102: The second nucleic acid construct of embodiment 101, wherein the second marker is a fluorescent marker.

Embodiment 103: The second nucleic acid construct of embodiment 99, wherein the second nucleic acid construct is integrated into the genome of a recombinant yeast strain.

Embodiment 104: The second nucleic acid construct of embodiment 99, wherein the 5' and 3' homology arms of the nucleic acid construct facilitate homologous pairing between the nucleic acid construct and a genomic target region resulting in the nucleic acid construct being introduced into the genomic target region.

Embodiment 105: The second nucleic acid construct of embodiment 99, wherein the second SAP binds to a cell wall GPI anchored protein.

Embodiment 105a: The first nucleic acid construct of embodiment 105, where the SAP is fused to a protein that binds to a cell wall GPI anchored protein.

Embodiment 106: The second nucleic acid construct of embodiment 99, wherein the unique barcode is specific to the synthetic adhesion protein of the first expression cassette.

Embodiment 107: The second nucleic acid construct of embodiment 99, wherein the recombination site is a lox site.

Embodiment 108: The second nucleic acid construct of embodiment 107, wherein the lox site is loxP, lox66, lox71, lox511, lox5171, lox2272, M2, M3, M7, or M11.

Embodiment 109: The second nucleic acid construct of embodiment 100, wherein the first marker of the first nucleic acid construct is an auxotrophic marker and is different than first marker of the second nucleic acid construct that is an auxotrophic marker.

Embodiment 110: The second nucleic acid construct of embodiment 102, wherein the fluorescent marker of the first nucleic acid construct is different than the fluorescent marker of the second nucleic acid construct.

Embodiment 111: The second nucleic acid construct of embodiment 99, wherein the genomic target of the first nucleic acid construct and the second nucleic acid construct is on the same chromosomal locus.

Embodiment 112: The second nucleic acid construct of embodiment 99, wherein the unique primer binding site of the first nucleic acid construct and the unique primer binding site of the second nucleic acid construct are integrated into the same chromosomal locus and after mating and chromosomal translocation the primer binding sites can be used to amplify a target nucleotide sequence comprising both the unique barcode of the first nucleic acid construct and the unique barcode of the second nucleic acid construct.

Embodiment 113: The second nucleic acid construct of embodiment 99, wherein the unique barcode of the first nucleic acid construct and the unique barcode of the second nucleic acid construct are integrated into the same chromosomal locus and after mating and chromosomal translocation are within about 5,000, 4,000, 3,000, 2,000, 1,000, 900, 800, 700, 600, 500, 400, 300, 200 or 100 base pairs.

Embodiment 114: A vector comprising the second nucleic acid construct of embodiment 99, wherein the vector comprises a high copy origin of replication and a resistance gene.

These and other features and advantages of the present disclosure will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE DRAWINGS

The disclosed exemplary aspects have other advantages and features which will be more readily apparent from the detailed description, the appended claims, and the accompanying figures. A brief description of the drawings is below.

FIG. 2C shows a schematic of the CRE recombinase translocation scheme for high throughput analysis for interactions between synthetic adhesion proteins from a library to library screen. When CRE recombinase expression is induced in diploids with βE, a chromosomal translocation at lox sites consolidates both SAP-Aga2 expression cassettes onto the same chromosome. A single fragment containing both barcodes is then amplified by PCR with primers annealing to primer bind sites from each of the first and second nucleic acid constructs and sequenced (for example, using a paired end analysis of next generation sequencing) to identify the interacting SAP pair.

FIG. 3A shows a recombinant MATa display yeast strain (left) constitutively expressing mCherry and a recombinant MATalpha display yeast strain (right) constitutively expressing mTurquoise mixed in liquid culture. The efficiency of diploid formation is dependent on the cells' capacity for agglutination. FIG. 3B shows wild type S. cerevisiae expressing the native sexual agglutinins have an observed mating efficiency of greater than 50%. FIG. 3C show that when the MATalpha sexual agglutinin, Sag 1, is knocked out, the mating efficiency falls nearly to zero. FIG. 3D shows that the expression of complementary SAPs recovers mating efficiency. Here a mating between Bcl2 and Bim.BH3 expressing cells is used as an example of a complementary pair. FIG. 3E shows that non-complementary pairs do not recover mating. Here, a mating between Bcl2 and BINDI-B+ expressing cells is used as an example of a non-complementary pair. FIG. 3F shows that following the co-culture of a display pair, cytometry is performed to identify the diploid population percent. Here, the log of mCherry fluorescence is on the x-axis and the log of mTurquoise expression is on the y-axis. The diploid population expresses both fluorescent reporters FIG. 3G and FIG. 3H show that mating efficiency is also dependent on the surface expression strength of each SAP. All SAP constructs contain a myc tag, which can be labeled with FITC conjugated anti-myc antibody. Fluorescent intensity of FITC can then be measured with flow cytometry and provides a relative measure of how much SAP is being displayed on the surface of each cell. Here, cytometry results for a strain that is not properly surface displaying (FIG. 3G) and a strain that is displaying correctly (FIG. 3H) are shown.

FIG. 11 shows an example of a computational model constructed to predict potential dynamic behaviors of the *S. cerevisiae* reproductive ecology model FIG. 12A shows the population dynamics from each mating likelihood matrix were plotted for a total of 500 generations, or 500 rounds of mating and sporulation. Each line represents the total population percent of a distinct isogenic haploid strain. FIG. 12B shows that most simulations result in a single pair of haploid strains taking over the population within 500 generations. FIG. 12C shows some simulations show a greater ecological instability and possibly oscillatory behaviors, with dramatic changes in population percent even after 500 generations.

FIG. 14A shows that MATa and MATalpha haploid strains constitutively express mCherry and mTurquoise, respectively, along with synthetic agglutinin proteins on their surfaces. Following the mixing of a MATa and MATalpha pair, PPI dependent agglutination causes mating, leading to a mixed population of haploid and diploid cells. FIG. 14B shows a dual channel fluorescence cytometry assay differentiates between haploid and diploid populations and is used to calculate mating efficiency (wild-type mating is shown here). FIG. 14C shows that haploid cells expressing wild-type sexual agglutinin proteins mate with an efficiency of 57.1%. The knockout of SAG1 from MATalpha eliminates mating. Expression of a matching SAP pair with an affinity comparable to that of the wild-type interaction recovers mating efficiency (Bcl2/Bindi-2+ is shown here, $K_D$=0.84nM), while a mismatched pair does not (Bcl2/Bindi-B+ is shown here, $K_D$>25,000nM). FIG. 14D shows a strong monomial relationship exists between mating efficiency and affinity for PPIs with a $K_D$ between 100 μM and 100 pM.

FIG. 16A shows MATa and MATalpha SAP cassettes are flanked by a mating type specific primer binding site and lox recombination site and a SAP specific barcode. Following a batched mating, CRE recombinase expression is induced in diploid cells, causing a recombination that combines the MATa and MATalpha SAP cassettes and barcodes onto the same chromosome so that interacting SAP pairs can be counted with Next Gen sequencing. FIG. 16B shows that batched mating assay gives a strong monomial relationship between the batched mating percent and affinity for PPIs with a $K_D$ between 100 μM and 100 pM. FIG. 16C shows that all protein interactions between five Bcl2 family homologues and seven peptide binders were characterized in a one-pot mating assay. FIG. 16D shows an expansion of the interaction profile for the overall weakest interacting peptide, Bad. FIG. 16E shows a comparison of relative pairwise mating efficiencies with the batched mating approach gives 1:1 agreement.

FIG. 18A shows the batched mating environment can be manipulated with the addition of arbitrary molecules that disrupt particular interactions. FIG. 18B shows the addition of a competing peptide, Bad, to a mating between five Bcl2 homologues and a panel of de novo binders results in the isolated disruption of interactions involving Bcl2 and BclXL. FIG. 18C shows a visualization of the PPI network consisting of Bcl2 homologues and de novo binders in the absence and presence of 100nM Bad.

FIG. 20A shows pNGYSDa and FIG. 20B shows pNGYSDa are each constructed with a four fragment Gibson assembly. The fragments include a SAP with standard overhangs, a barcode containing fragment amplified with a degenerate primer, and two backbone fragments. Following transformation into E. coli, plasmid open reading frames and barcodes are sequenced. Verified plasmids are digested with PmeI and transformed into yNGYSDa or yNGYSDα. FIG. 20C shows for library integrations, yNGYSDa and yNGYSDα are first grown for 6 hours in GAL media to induce SceI expression causing DNA damage at the integration site. Cells are then transformed with four mating type dependent fragments, which assemble with homologous recombination and are selected with TRP.

FIG. 21 shows a yeast strain construction flowchart.
FIG. 22 shows binding results from a pairwise mating.
FIG. 23 shows binding results from a batched mating.
FIG. 24 shows binding results from a batched mating.

DETAILED DESCRIPTION OF THE INVENTION

Figure 1:
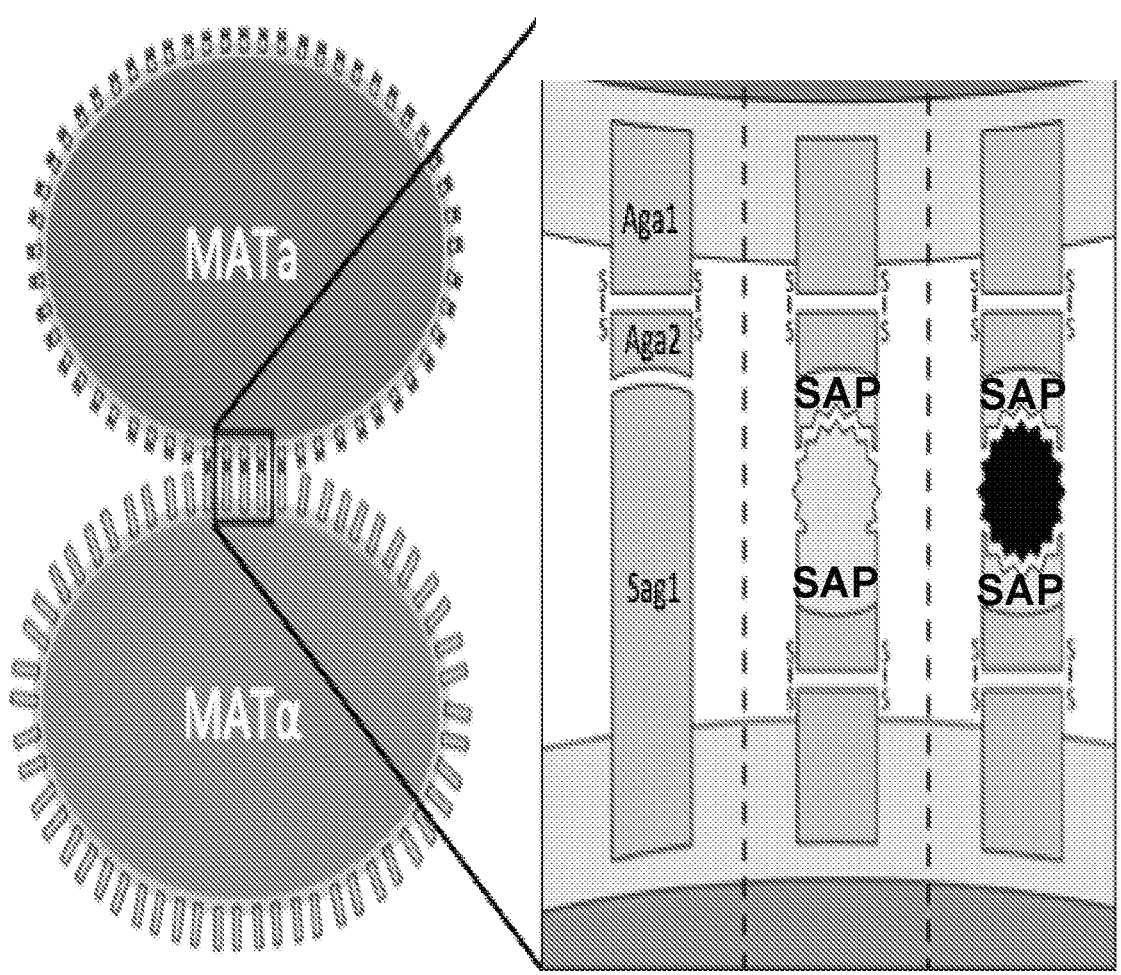
FIG. 1 shows a cartoon depiction of natural and synthetic sexual agglutination in S. cerevisiae. At the left, the MATa (top) and MATα (bottom) haploids are top and bottom, respectively. The cell wall of each haploid cell is shown in grey. In a turbulent liquid culture, MATa and MATα haploid cells stick to one another due to the binding of sexual agglutinin proteins, which allows them to mate. The native sexual agglutinin proteins consist of Aga1 and Aga2, expressed by MATa cells, and Sag1, expressed by MATα cells. Aga1 and Sag1 form GPI anchors with the cell wall and extend outside of the cell wall with glycosylated stalks (see left frame of inset). Aga2 is secreted by MATa cells and forms a disulfide bond with Aga1. The interaction between Aga2 and Sag 1 is essential for wild-type sexual agglutination. The native sexual agglutinin interaction can be replaced with an engineered one by expressing Aga1 in both mating types and fusing complementary binders to Aga2 (see middle frame of inset). Instead of direct agglutination, it may be possible to express binders for a multivalent target, such that agglutination and mating only occurs in the presence of the target (see right frame of inset).

All references cited are herein incorporated by reference in their entirety. Within this application, unless otherwise stated, the techniques utilized may be found in any of several well-known references such as: Molecular Cloning: A Laboratory Manual (Sambrook, et al., 1989, Cold Spring Harbor Laboratory Press), Gene Expression Technology (Methods in Enzymology, Vol. 185, edited by D. Goeddel, 1991. Academic Press, San Diego, Calif.), "Guide to Protein Purification" in Methods in Enzymology (M.P. Deutshcer, ed., (1990) Academic Press, Inc.); PCR Protocols: A Guide to Methods and Applications (Innis, et al. 1990. Academic Press, San Diego, Calif.), Culture of Animal Cells: A Manual of Basic Technique, 2nd Ed. (R.I. Freshney. 1987. Liss, Inc. New York, N.Y.), Gene Transfer and Expression Protocols, pp. 109-128, ed. E.J. Murray, The Humana Press Inc., Clifton, N.J.), and the Ambion 1998 Catalog (Ambion, Austin, Tex.).

Terms used in the claims and specification are defined as set forth below unless otherwise specified. In the case of direct conflict with a term used in a parent provisional patent application, the term used in the instant specification shall control.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

The following definitions and explanations are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition or a dictionary known to those of skill in the art, such as the Oxford Dictionary of Biochemistry and Molecular Biology (Ed. Anthony Smith, Oxford University Press, Oxford, 2004).

As used herein, the singular forms "a", "an" and "the" include plural referents unless the context clearly dictates otherwise. "And" as used herein is interchangeably used with "or" unless expressly stated otherwise.

The terms "nucleic acid," "polynucleotide" and "oligonucleotide" are used interchangeably and refer to deoxyribonucleotides or ribonucleotides or modified forms of either type of nucleotides, and polymers thereof in either single- or double-stranded form. The terms should be understood to include equivalents, analogs of either RNA or DNA made from nucleotide analogs and as applicable to the embodiment being described, single stranded or double stranded polynucleotides. In certain embodiments, an oligonucleotide may be chemically synthesized.

All embodiments disclosed herein can be used in combination unless the context clearly dictates otherwise.

In a first aspect, the invention provides an assay for identifying protein-protein interactions comprising:
(A) culturing a mixture of a first recombinant yeast strain integrated with a first nucleic acid construct and a second recombinant yeast strain integrated with a second nucleic acid construct for a time and under conditions resulting in:
  (1) expression in the first recombinant yeast strain of one or more first synthetic adhesion proteins (SAPs) bound to a first cell wall glycosylphosphatidylinositol (GPI) anchored protein on the surface of the first recombinant yeast strain;
  (2) expression in the second recombinant yeast strain of one or more second synthetic adhesion proteins bound to a second cell wall GPI anchored protein on the surface of the second recombinant yeast strain;
  (3) formation of protein-protein interactions between the one or more first SAPs bound to the first cell wall GPI anchored protein and the one or more second SAPs bound to the second cell wall GPI anchored protein, such that mating can occur between the first recombinant yeast strain and the second recombinant yeast strain wherein:
    (a) one or both of the first recombinant yeast strain and the second recombinant yeast strain comprises an exogenous recombinase;
    (b) one or both of the first recombinant yeast strain and the second recombinant yeast strain does not express at least one native sexual agglutination protein;
    (c) the first nucleic acid construct comprises:
      (i) a homology arm at the 5' end of the nucleic acid construct,
      (ii) a first expression cassette comprising a gene coding for the first SAP,
      (iii) a second expression cassette comprising a first marker,
      (iv) a unique primer binding site,
      (v) a unique nucleic acid barcode,
      (vi) a recombination site, and
      (vii) a homology arm at the 3' end of the nucleic acid construct; and
    (d) the second nucleic acid construct comprises:
      (i) a homology arm at the 5' end of the nucleic acid construct,
      (ii) a first expression cassette comprising a gene coding for the second SAP,
      (iii) a second expression cassette comprising a first marker,
      (iv) a unique primer binding site,
      (v) a unique nucleic acid barcode,
      (vi) a recombination site, and
      (vii) a homology arm at the 3' end of the nucleic acid construct; and
(B) determining the percentage of diploid yeast cells from the mixture wherein diploid cells indicate a protein-protein interaction between the first SAP and the second SAP.

In certain embodiments, the first and second recombinant yeast strains are budding yeast. In some embodiments, the budding yeast can be, but is not limited to, *Pichia pastoris* or *Saccharomyces cerevisiae*. In other embodiments, any yeast that rely an initial binding step, called sexual agglutination, when mating in a turbulent liquid culture could be used in the assay. In certain embodiments, the yeast used in the assay is *Saccharomyces cerevisiae* and the first recombinant yeast strain is a MATa yeast strain, and the second recombinant yeast strain is a MATalpha yeast strain. In other embodiments, the yeast used in the assay is *Saccharomyces cerevisiae* and the first recombinant yeast strain is a MATalpha yeast strain, and the second recombinant yeast strain is a MATa yeast strain.

In certain embodiments, the pair of yeast strains is configured so that between the pair of yeast strains at least one strain comprises an exogenous recombinase and at least one strain does not express at least one native sexual agglutination protein. Native sexual agglutination and mating can be disrupted by having at least one yeast strain in a pair of yeast strains that does not express at least one sexual agglutination protein. In an embodiment, one or both of the first recombinant yeast strain and the second recombinant yeast strain comprises an exogenous recombinase. In another embodiment, one or both of the first recombinant yeast strain and the second recombinant yeast strain does not express at least one native sexual agglutination protein. In an embodiment, the first recombinant yeast strain comprises both an exogenous recombinase and does not express at least one native sexual agglutination protein while the second yeast strain does not have an exogenous recombinase and can express native sexual agglutination proteins. In another embodiment, the second recombinant yeast strain comprises both an exogenous recombinase and does not express at least one native sexual agglutination protein while the first recombinant yeast strain is does not comprise an exogenous recombinase. In certain embodiments, one or both of the yeast strains comprises an exogenous recombinase. In some embodiments, one or both of the yeast strains comprises an exogenous recombinase and one or both of the yeast strains does not express at least one native sexual agglutination protein. In certain embodiments, the exogenous recombinase is expressed only in diploid cells following mating.

In some embodiments, the first recombinant yeast strain and the second recombinant yeast strain comprise a selection marker. Expression of a selection marker in a yeast strain permits selection of cells containing the selection marker gene from cells that do not contain the selection marker gene. In certain embodiments, the selection marker of the first recombinant yeast strain and is different from the selection marker of the second recombinant yeast strain. In an embodiment, the selection marker is an auxotrophic marker or an antibiotic marker. In another embodiment, the selection marker is an auxotrophic marker. For example, the auxotrophic marker can be, but is not limited to, ADE1, ADE2, CAN1, HIS3, LEU2, LYS2, TRP1, TRPS, URA3 or URA4. In yet another embodiment, the selection marker is an antibiotic resistance marker. For example, the antibiotic resistance marker provides resistance to geneticin, nourseothricin, bleomycin, hygromycin, phleomycin, zeocin, canavanine, kanamycin, spectinomycin, streptomycin, ampicillin, carbenicillin, bleomycin, erythromycin, polymyxin, tetracycline, gentamycin or chloramphenicol.

As used herein, term "nucleic acid construct" refers to a contiguous polynucleotide or DNA molecule capable of being integrated into a yeast strain. In certain embodiments the nucleic acid construct comprises: (a) a homology arm at the 5' end of the nucleic acid construct, (b) a first expression cassette comprising a gene coding for a synthetic adhesion protein (SAP) that binds to a cell wall glycosylphosphatidylinositol (GPI) anchored protein, (c) a second expression cassette comprising a first marker, (d) a unique primer binding site, (e) a unique nucleic acid barcode, (f) a recombination site, and (g) a homology arm at the 3' end of the nucleic acid construct. In certain embodiments, components (a) through (g) of the nucleic acid construct are arranged in a 5'to 3' direction on the nucleic acid construct; wherein component (a) is 5' to component (b) and component (b) is 5' to component (c) and component (c) is 5' to component (d) and component (d) is 5' to component (e) and component (e) is 5' to component (f) and component (f) is 5' to component (g) and component (g) is at the 3' end of the nucleic acid construct to be integrated at a genomic target site. For example, in certain embodiments, the homology arm at the 5' end of the nucleic acid construct is 5' first expression cassette and the first expression cassette is 5' to the second expression cassette and the second expression cassette is 5' to the unique primer binding site and the unique primer binding site is 5' to the unique nucleic acid barcode and the unique nucleic acid barcode is 5' to the recombination site and the recombination site is 5' to the homology arm at the 3' end of the nucleic acid construct and the homology arm at the 3' end of the nucleic acid construct is at the 3' end of the nucleic acid construct to be integrated at a genomic target site.

The homology arm at the 5' end of the nucleic acid construct and the homology arm at the 3' end of the nucleic acid construct refer to regions of DNA that facilitate homologous pairing between the nucleic acid construct and a genomic target region resulting in the integration of the nucleic acid construct into the genomic target region. Homologous pairing refers to the pairing that can occur between two nucleic acid sequences or subsequences that are complementary, or substantially complementary, to each other. In certain embodiments, the nucleic acid construct can be integrated into the genomic target region through homologous pairing (i.e., homologous recombination) facilitated by the 5' and 3' homology arms. The term "genomic target region" or "genomic target locus" as used herein refers to a region of a cellular genome at which insertion of the nucleic acid construct is desired. In certain embodiments, the genomic target locus for the first nucleic acid cassette is the same genomic target locus for the second nucleic acid cassette. In an embodiment, the target genomic locus of the yeast strains is modified in order to improve the efficiency of integration of the nucleic acid construct at the locus. For example, cleavable target sites can be included at the intended site of integration and then expression of an exonuclease can be induced during the preparation of yeast competent cells (cells prepared to be transformed with DNA) that damages (i.e., nicks) the DNA at the target site and improves the efficiency of integration at that locus. In another embodiment, the nucleic acid constructs are integrated in opposite directions in their respective yeast strains. Integration in opposite orientations makes chromosomal translocation to combine barcodes from both the first expression cassettes comprising the SAP following mating possible (see FIG. 2A-C). In some embodiments, the genomic target locus is on chromosome III of S. cerevisiae.

In certain embodiments, nucleic acid plasmids carrying the SAPs of the invention can be transformed into the yeast strains. In such an embodiment, the nucleic acid plasmids can be for example, 2 micron or centromeric plasmids, which are not integrated into the genome.

As used herein, the term "expression cassette" refers to a DNA sequence comprising a promoter, an open reading frame, and a terminator. In certain embodiments, the nucleic acid construct comprises one or more expression cassettes. For example, the nucleic acid construct can comprise one, two, three or more expression cassettes. In certain embodiments, the nucleic acid construct comprises a first expression cassette comprising a gene coding for a first synthetic adhesion protein (SAP) bound to a first cell wall glycosylphosphatidylinositol (GPI) anchored protein, and a second expression cassette comprising a first marker. In some embodiments, the SAP of the first expression cassette of the first nucleic acid construct is fused to the sexual agglutination protein Aga2, and the SAP of the first expression cassette of the second nucleic acid construct is fused to the sexual agglutination protein Aga2. In some embodiments, the first marker of the first nucleic acid construct and the second nucleic acid construct is a selection marker. Expression of a selection marker in a yeast strain permits selection of cells containing the selection marker gene from cells that do not contain the selection marker gene. In some embodiments the selection marker can be an auxotrophic marker or an antibiotic marker.

In other embodiments, the nucleic acid construct comprises a third expression cassette, wherein the third expression cassette expresses a second marker. In some embodiments, the second marker of the nucleic acid construct is a fluorescent marker. Examples of fluorescent markers include, but are not limited to, GFP, EBFP, Azurite, T-Sapphire, Cerulean, mCFP, mTurquoise, ECFP, CyPet, mKeima-Red, TagCFP, AmCyan, mTFP, Midoriishi Cyan, Emerald, Azami Green, ZsGreen, TagYFP, EYFP, Topaz, Venus, mCitrine, YPet, ZsYellow, Kusabira Orange, mOrange, Allophycocyanin (APC), mKO, TurboRFP, tdTomato, TagRFP, DsRed, mStrawberry, TurboFP, AsRed, mRFP1, J-Red, R-phycoerythrin (RPE), mCherry, HcRed, Katusha, mKate, mPlum, and mRaspberry.

In certain embodiments, the fluorescent marker of the first nucleic acid construct is different than the fluorescent marker of the second nucleic acid construct. As used herein "promoter" means a nucleotide sequence typically located upstream from the 5' end of a gene or coding sequence for a protein that controls the transcription of RNA from DNA, in part, by interacting with various regulatory factors that control transcription. In an embodiment, the promoter may be derived from the same species of yeast strain as the yeast strain expressing the gene of interest from the expression cassette (i.e, SAP or marker). In another embodiment, the promoter may be derived from a different yeast species than the yeast strain expressing the gene of interest. In another embodiment, a promoter may include a TATA box sequence that acts as a recognition site to direct initiation of transcription, including, but not limited to one or more transcriptional enhancer elements. An "enhancer element" as used herein is a regulatory element that can stimulate promoter activity.

As described herein, a promoter can be a "constitutive promoter". A "constitutive promoter" means a promoter that regulates expression of a gene of interest. A constitutive promoter is typically active in all circumstances in the yeast strain, and use of a constitutive promoter results in a high level of expression or greater than native level of a target gene expression. A constitutive promoter can have some inducible activity, but the maximal activity obtained with the promoter is not inducible. In certain embodiments, examples of constitutive promoters can include, but are not limited to the ADH1 promoter, ADH2 promoter, ADH3 promoter, ADH4 promoter, ADH5 promoter, GAPDH1 promoter, GAPDH2 promoter, TEF1 promoter, TEF2 promoter, YEF3 promoter, CAM1 promoter, TEF4 promoter, EFB1 promoter, LEU promoter, PHO3 promoter, PHO5 promoter, PyK promoter, HIS4 promoter, CUP1 promoter, or ACO1 promoter.

As described herein, a promoter can be an "inducible promoter". An "inducible promoter" means a promoter that activates expression of a gene of interest in the yeast strain only in response to specific stimuli. Some inducible promoters can respond to and are induced by environmental stimuli such as water or salt stress, anaerobiosis, temperature, illumination or wounding. For example the heat shock promoters can be regulated by temperature shifts. Other inducible promoters can respond to and are induced by chemical compounds that either turn off or turn on gene transcription. Typically the chemicals influencing promoter activity should not be naturally present in the organism where expression of the transgene is sought; should not be toxic; should affect only the expression of the gene of interest; should be easy to apply or remove; and should induce a clearly detectable expression pattern of either high or very low gene expression. For example, inducible promoters can be regulated by alcohol, antibiotics, steroids or metals. In certain embodiments, examples of inducible promoters can include, but are not limited to GAL1 promoter, GAL2 promoter, GAL3 promoter, GAL4 promoter, GAL80 promoter, AOX promoter, FDH promoter PGK promoter or FLD1 promoter. Additional examples of inducible promoters can include promoters that contain zinc finger binding sites and require the expression of a zinc finger transcription factor (for example, the promoter pZ4 and the transcription factor ZEV4, which is activated with beta-estradiol).

In certain embodiments, the nucleic acid constructs comprise a recombination site. The recombination site allows certain site specific recombination events once the nucleic acid construct has been integrated into the target region and mating has occurred. More specifically, the recombination sites are located close to the barcoded SAP expression cassettes and are constructed so that recombination results in a chromosomal translocation that places the two barcodes from each of the first and second nucleic acid constructs that were previously integrated on the same chromosomes of the respective first and second yeast strains onto the same chromosome of the diploid yeast cell. In an embodiment, the recombination sites of the first and second nucleic acid constructs are designed so that recombination does not destroy the chromosomes or result in killing the cells. The site specific recombination events at the recombination sites are controlled by a site specific recombinase, which can catalyze the site specific recombination event between two DNA recombination sites. In certain embodiments, one or both of the yeast strains comprises an exogenous recombinase. The recombinase is expressed only in diploid cells following mating. For example, the second recombinant yeast strain can express a transcription factor and the first recombinant yeast strain comprises the exogenous recombinase or the first recombinant yeast strain can express a transcription factor and the second recombinant yeast strain comprises the exogenous recombinase. It is also possible to have both strains comprise the exogenous recombinase and the transcription factor. In some embodiments, just one of the strains comprises an inducible promoter controlling expression of the exogenous recombinase. In order to express the recombinase only in the mated diploid cells, an inducible transcription factor, (for example, Zev4), is controllably induced (i.e., Zev4 is activated with beta-estradiol which permits entry of Zev4 into the nucleus where it then activates the promoter pZ4), and activates transcription from its promoter which is placed upstream of the recombinase. Thus, adding an inducer (i.e., beta-estradiol) to the mated cells activates expression of the exogenous recombinase and causes a chromosomal translocation in diploids that pairs two barcodes together.

In certain embodiments, the nucleic acid constructs each comprise a unique primer binding site. The unique primer binding sites are designed to allow amplification with that set of primers that will only amplify a target nucleic acid fragment containing 2 unique barcodes from correctly recombined diploid cells. The target nucleic acid fragment pool is then sequenced, for example, using next generation sequencing. As used herein, a primer or primer pair refers to an oligonucleotide pair (i.e, a forward and reverse primer), either natural or synthetic that is capable, upon forming a duplex with a polynucleotide template, of acting as a point of initiation of nucleic acid synthesis and being extended from its 3' end along the template so that a target nucleic acid fragment is formed. In yet another embodiment, the unique primer binding site of the first nucleic acid construct and the unique primer binding site of the second nucleic acid construct are integrated into the same chromosome and after mating and chromosomal translocation the primer binding sites can be used to amplify a target nucleotide sequence comprising both the unique barcode of the first nucleic acid construct and the unique barcode of the second nucleic acid construct. In an embodiment, the unique barcode of the first nucleic acid construct and the unique barcode of the second nucleic acid construct are integrated into the same chromosomal locus and after mating and chromosomal translocation are within about 5,000, 4,000, 3,000, 2,000, 1,000, 900, 800, 700, 600, 500, 400, 300, 200 or 100 base pairs. In some embodiments, using next generation sequencing, a paired end read is used to read the barcodes at either end of a target nucleic acid fragment.

In certain embodiments, the nucleic acid constructs each comprise a unique nucleic acid barcode. Each barcode is specific to a certain synthetic adhesion protein. In some embodiments, the barcodes are not specifically chosen. Instead, they are added with degenerate primers that contain a region with random base pairs (for example in a library to library screen of synthetic adhesion proteins). In another embodiment, the nucleic acid constructs are integrated in opposite directions in their respective yeast strains so that the barcodes are in close proximity to each other following mating and recombination. Integration in opposite directions means that in one strain the barcode is 5' of the recombination site and in the other strain the barcode is 3' of the recombination site. Then, when recombination occurs, a chromosomal translocation results in both of the barcodes on the same chromosome of the diploid cell (for example see FIG. 2B and FIG 2.C).

As used here, the term "cell wall glycosylphosphatidylinositols (GPI) anchored protein" refers to a protein that is attached to a GPI complex via an amide linkage to the protein's C-terminal carboxyl group. GPI's can be a glycolipid that can be attached to the C-terminus of a protein during post-translational modification. GPI-linked proteins contain a signal sequence, thus directing them to the endoplasmic reticulum. The protein is co-translationally inserted in the endoplasmic reticulum membrane and is attached to the ER membrane by its hydrophobic C terminus; the majority of the protein extends into the ER lumen. The hydrophobic C-terminal sequence is then cleaved off and replaced by the GPI-anchor. As the protein processes through the secretory pathway, it is transferred via vesicles to the Golgi apparatus and finally to the plasma membrane where it remains attached to a leaflet of the cell membrane. In an embodiment, the SAP is bound to the cell wall GPI anchored protein. For example the SAP can be bound to the cell wall GPI anchored protein by forming a disulfide bond with the cell wall GPI anchored protein or the SAP can be fused to a protein that forms a disulfide bond with the cell wall GPI anchored protein. In such an embodiment, the SAPs can be fused to a protein that is secreted and forms a disulfide bond with a cell wall GPI-anchored protein. An example of a protein that is secreted and forms a disulfide bond with a cell wall GPI-anchored protein can include, but is not limited to, the sexual agglutination protein Aga2. An example of a cell wall GPI anchored protein can include, but is not limited to, the sexual agglutination protein Aga1. In some embodiments, the synthetic adhesion proteins are fused in frame with a cell wall GPI anchored protein and the SAPs are expressed and transported to exterior of the cell wall of the yeast strains anchored to the cell wall by the cell wall GPI anchored protein. In an embodiment, the synthetic adhesion proteins are fused in-frame with the cell wall GPI anchored protein. In another embodiment, the synthetic adhesion proteins are fused in frame with the cell wall anchored protein and there is a peptide linker between the synthetic adhesion protein and the cell wall GPI anchored protein. Peptide linker typically comprise between approximately 5 and 20 amino acids (for example, GGGS or 3xGGGS). The present disclosure is not limited to the use of a peptide linker, and any suitable linker may be utilized. In other embodiments, the SAP and the cell wall GPI anchored proteins are fused without a linker. For example, in yet another embodiment, the SAP is bound to the cell wall GPI anchored protein by forming a disulfide bond with the cell wall GPI anchored protein or the SAP is fused to a protein that forms a disulfide bond with the cell wall GPI anchored protein. In such an embodiment, the SAPs can be fused to a protein, with or without the use of a peptide linker that is secreted and forms a disulfide bond with a cell wall GPI-anchored protein. An example of a protein that is secreted and forms a disulfide bond with a cell wall GPI-anchored protein can include, but is not limited to, the sexual agglutination protein Aga2. An example of a cell wall GPI anchored protein can include, but is not limited to, the sexual agglutination protein Aga1.

As used herein, "sexual agglutination proteins" refer to proteins of the budding yeasts and are cell adhesion proteins that promote aggregation of yeast cells during mating. In each yeast species, complementary sexual agglutination proteins are expressed by cells of opposite mating type that interact to mediate aggregation. In certain embodiments, the native sexual agglutination proteins are knocked out and mating is restored by the exogenous surface expression of proteins capable of forming protein-protein interactions sufficient for mating (e.g., a pair of synthetic adhesion proteins). For example, in Saccharomyces cerevisiae, the primary agglutination interaction is between the MATa sexual agglutinin subunit Aga2 and the MATalpha sexual agglutinin Sag 1. Aga1 from the MATa mating type and Sag1 from the MATalpha mating type form glycosylphosphatidylinositol (GPI) anchors with the yeast cell wall and extend glycosylated stalks outside of the cell wall. Aga2 is secreted by MATa cells and forms a disulfide bond with Aga1 (see FIG. 1). In certain embodiments, the first recombinant yeast strain expresses Aga1. In other embodiments, the second recombinant yeast strain expresses Aga1. In yet another embodiment, both the first yeast strain and the second yeast strain express Aga1. In some embodiments, Aga1 is overexpressed in the yeast strain, and can be constitutively overexpressed or inducibly overexpressed. In certain embodiments, endogenous Aga1 is controllably expressed by knocking out the native Aga1 promoter and replacing it with a constitutive or inducible promoter. In other embodiments, native Aga1 is knocked out and Aga1 overexpression is by an exogenous Aga1 regulated by a constitutive or inducible promoter. In certain embodiments, the yeast strains do not express the native sexual agglutination protein Aga2 or Aga2 is knocked out. In an embodiment, the second recombinant yeast strain does not express the native sexual agglutination protein Sag1 or Sag1 is knocked out.

As used herein, "protein-protein interaction" or "PPI" refers to physical contacts of high specificity established between two or more proteins as a result of biochemical events driven by electrostatic forces including the hydrophobic effect. Many are physical contacts with molecular associations between chains that occur in a cell or in a living organism in a specific biomolecular context. In some embodiments, the protein-protein interactions are strong enough to replace the function of the native sexual agglutination proteins. For example, it can be possible to couple mating efficiency to the interaction strength of a particular protein-protein interaction. In certain embodiments, the assay can characterize or determine protein-protein interactions between synthetic adhesion proteins (SAPs).

As used herein, a "synthetic adhesion protein" can refer to any protein or polypeptide to be assayed for binding to or interacting with any other any protein or polypeptide. The proteins can be heterologous or exogenously expressed. Synthetic adhesion proteins are referred to as such because they are not typically associated with the adhesion required for agglutination as natively performed by the sexual agglutination proteins. In certain embodiments, the synthetic adhesion proteins have sufficiently strong interactions as to allow agglutination in yeast where the native sexual agglutination proteins are not natively expressed. In some embodiments, the SAPs of the first and second expression cassettes of the first and second nucleic acid constructs, respectively, bind to a cell wall GPI anchored protein. In some embodiments, the SAPs can be fused to a cell wall GPI anchored protein or fused to a protein that forms a disulfide bond with a cell wall GPI anchored protein. In some embodiments, the SAP of the first expression cassette of the first nucleic acid construct is fused to the sexual agglutination protein Aga2, and the SAP of the first expression cassette of the second nucleic acid construct is fused to the sexual agglutination protein Aga2.

In certain embodiments of the assay, a gene coding for a SAP fused to the cell wall GPI anchored protein or a protein that forms a disulfide bond with a cell wall GPI anchored protein of the first expression cassette of the first nucleic acid construct integrated into the first recombinant yeast strain is assayed for binding to a gene coding for a SAP fused to the cell wall GPI anchored protein or a protein that forms a disulfide bond with a cell wall GPI anchored protein of the first expression cassette of the second nucleic acid construct into the second recombinant yeast strain; and wherein the protein-protein interaction is determined by measuring for diploid yeast cells from the mixture. In some embodiments, the markers of the nucleic acid constructs can be used to determine the different cell populations (for example by using flow cytometry).

In another embodiment of the assay, a gene coding for a SAP fused to the cell wall GPI anchored protein or a protein that forms a disulfide bond with a cell wall GPI anchored protein of the first expression cassette of the first nucleic acid construct integrated into the first recombinant yeast strain is assayed for binding to a library of genes coding for a library of different SAPs fused to the cell wall GPI anchored protein or a protein that forms a disulfide bond with a cell wall GPI anchored protein of the first expression cassette of the second nucleic acid construct integrated into a population of second recombinant yeast strains, and wherein the protein-protein interaction is determined by: (a) isolating genomic DNA from the mixture of yeast strains, (b) amplifying a target DNA sequence using primers specific to the unique primer regions of the first and second nucleic acid constructs; and (c) sequencing the target DNA sequence to determine the protein-protein interaction. In such an embodiment, a batched mating is performed testing the binding of one synthetic adhesion protein expressed in one yeast strain (i.e., MATa) to many synthetic adhesion proteins expressed in a second yeast strain (i.e., MATalpha). Following mating, the diploid cells are selected from the culture mixture and a colony PCR is run. The PCR products are purified and next generation sequence can be used to analyze the relative barcode frequencies.

In yet another embodiment of the assay, a library of genes coding for the SAP fused to the cell wall GPI anchored protein or a protein that forms a disulfide bond with a cell wall GPI anchored protein of the first expression cassette of the first nucleic acid construct integrated into a population of the first recombinant yeast strains is assayed for binding to a library of genes coding for the SAP fused to the cell wall GPI anchored protein or a protein that forms a disulfide bond with a cell wall GPI anchored protein of the first expression cassette of the second nucleic acid construct integrated into a population of second recombinant yeast strains, and wherein the protein-protein interaction is determined by isolating genomic DNA from the mixture of yeast strains and sequencing the genomic DNA acid using primers specific for the unique primer binding sites to sequence the genomic DNA and determine the protein-protein interaction. In such an embodiment, a batched mating is performed testing the binding of a library of synthetic adhesion protein expressed in the first recombinant yeast strain (e.g.., MATa) to a library of synthetic adhesion proteins expressed in the second recombinant yeast strain (e.g., MATalpha). Following mating, the diploid cells are selected from the culture mixture and expression of the recombinase is induced so that recombination occurs. After recombination, the unique primers for each of the first and second nucleic acid constructs are at the same genomic target locus in the diploid cells and a colony PCR is run using primers specific to the unique primers. The PCR products are then purified and a paired-end next generation sequencing can be used to analyze the relative barcode frequencies.

In certain embodiments, the assay further comprises culturing the mixture of the first recombinant yeast strain and the second recombinant yeast strain in the presence of a potential modulator of protein-protein interactions. In an embodiment, the modulator of protein-protein interactions is a small molecule, a polypeptide, a nucleic acid, or an environmental factor. Since the protein-protein interaction occurs outside of the cell, membrane soluble or insoluble compounds can be added to the media exogenously to screen potential therapeutic molecules for their on- and off-target disruption of protein interactions. This modulator could result in the disruption of PPIs by competitive binding and would therefore cause a decrease in mating for those particular PPIs that bound to the modulator in a competitive fashion. The modulator could also enhance a PPI, for example by satisfying hydrophobic residues in a small pocket in the interface, which would result in increased mating efficiency for those particular PPIs that bound to the modulator. In some embodiments of the assay, it could be possible to identify interactions that are strengthened, unaffected, or weakened by the addition of an arbitrary modulator.

In a second aspect, the invention provides a kit comprising:

(a) a first recombinant yeast strain and a second recombinant yeast strain, wherein one or both of the first recombinant yeast strain and the second recombinant yeast strain comprises an exogenous recombinase, and one or both of the first recombinant yeast strain and the second recombinant yeast strain does not express at least one native sexual agglutination protein;

(b) a first nucleic acid construct comprising:
(i) a homology arm at the 5' end of the nucleic acid construct,
(ii) a first expression cassette comprising a gene coding for the first SAP,
(iii) a second expression cassette comprising a first marker,
(iv) a unique primer binding site,
(v) a unique nucleic acid barcode,
(vi) a recombination site, and
(vii) a homology arm at the 3' end of the nucleic acid construct; and (c) a second nucleic acid construct comprising:
(i) a homology arm at the 5' end of the nucleic acid construct,
(ii) a first expression cassette comprising a gene coding for the second SAP,
(iii) a second expression cassette comprising a first marker,
(iv) a unique primer binding site,
(v) a unique nucleic acid barcode,
(vi) a recombination site, and
(vii) a homology arm at the 3' end of the nucleic acid construct.

In certain embodiments, the first and second recombinant yeast strains are budding yeast selected from *Pichia pastoris* or *Saccharomyces cerevisiae*. In an embodiment, the first recombinant yeast strain is a MATa yeast strain and the second recombinant yeast strain is a MATalpha yeast strain. In an embodiment, the first recombinant yeast strain comprises a selection marker and the second recombinant yeast strain comprises a selection marker; wherein the selection marker of the first recombinant yeast strain is different than the selection marker of the second recombinant yeast strain. In some embodiments, the first recombinant yeast strain comprises an auxotrophic marker and the second recombinant yeast strain comprises an auxotrophic marker; wherein the auxotrophic marker of the first recombinant yeast strain is different than the auxotrophic marker of the second recombinant yeast strain. In another embodiment, the first recombinant yeast strain expresses Aga1 and the second recombinant yeast strain expresses Aga1. In yet another embodiment, the second recombinant yeast strain does not express the native sexual agglutination protein Sag 1. In certain embodiments of the kit, the SAP of the first expression cassette of the first nucleic acid construct is fused to the sexual agglutination protein Aga2, and the SAP of the first expression cassette of the second nucleic acid construct is fused to the sexual agglutination protein Aga2. In other embodiments, both the first recombinant yeast strain and the second recombinant yeast strain comprise a selection marker, wherein the selection marker can be an auxotrophic marker or an antibiotic marker. In certain embodiments, the first nucleic construct comprises a third expression cassette comprising a second marker, wherein the second marker is a fluorescent marker. In other embodiments, the second nucleic acid construct comprises a third expression cassette comprising a second marker, wherein the second marker is a fluorescent marker. In an embodiment, the fluorescent marker of the first nucleic acid construct is different than the fluorescent marker of the second nucleic acid construct.

In certain embodiments, the kit comprises instructions to carry out insertion of the synthetic adhesion proteins into the first expression cassettes of the first and second nucleic acid constructs. In another embodiment, the kit comprises instructions to carry out a screen of a library of synthetic adhesion proteins in order to determine binding (i.e., a protein-protein interaction) between two or more of the synthetic adhesion proteins in the library.

In some embodiments, the nucleic acid constructs are each part of separate vectors. In an aspect, the disclosure provides a first recombinant yeast strain and a second recombinant yeast strain, wherein one or both of the first recombinant yeast strain and the second recombinant yeast strain comprises an exogenous recombinase, and one or both of the first recombinant yeast strain and the second recombinant yeast strain does not express at least one native sexual agglutination protein. In certain embodiments, the first recombinant yeast strain is a MATa yeast strain that overexpresses Aga1 and does not express at least one native sexual agglutination protein. In certain embodiments, the recombinant MATa yeast strain does not express the native sexual agglutination protein Aga2. In another embodiment, the recombinant MATa yeast strain constitutively overexpresses Aga1 or inducibly overexpresses Aga1. In some embodiments, the recombinant MATa yeast strain constitutively overexpresses Aga1 and the constitutive overexpression of Aga1 is regulated by a constitutively active promoter. Examples of constitutively active promoters include, but are not limited to, the ADH1 promoter, ADH2 promoter, ADH3 promoter, ADH4 promoter, ADH5 promoter, GAPDH1 promoter, GAPDH2 promoter, TEF1 promoter, TEF2 promoter, YEF3 promoter, CAM1 promoter, TEF4 promoter, EFB1 promoter, LEU promoter, PHO3 promoter, PHO5 promoter, PyK promoter, HIS4 promoter, CUP1 promoter, or AC01 promoter. In another embodiment, the recombinant MATa yeast strain inducibly overexpresses Aga1 and the inducible overexpression of Aga1 is regulated by an inducible promoter. Examples of inducible promoters include, but are not limited to, the GAL1 promoter, GAL2 promoter, GAL3 promoter, GAL4 promoter, GAL80 promoter, AOX promoter, FDH promoter PGK promoter or FLD1 promoter. In certain embodiments, endogenous Aga1 is replaced with exogenous Aga1 regulated by a constitutively active promoter or an inducible promoter.

In certain embodiments, wherein the recombinant first recombinant yeast strain is a budding yeast, selected from *Pichia pastoris* and *Saccharomyces cerevisiae*.

In other embodiments, the first recombinant yeast strain comprises an exogenous recombinase, wherein the first recombinant yeast strain inducibly expresses the exogenous recombinase. In an embodiment, the inducible expression of the exogenous recombinase is regulated by a transcription factor, and the transcription factor is constitutively expressed in the second yeast strain and requires an additional molecule to activate expression from the inducible promoter. A non-limiting example of a recombinase is CRE recombinase.

In an embodiment, the first recombinant yeast strain comprises at least one selection marker, wherein the selection marker can be an auxotrophic marker or an antibiotic marker. In some embodiments, the selection marker is an auxotrophic marker selected from ADE1, ADE2, CAN1, HIS3, LEU2, LYS2, TRP1, TRPS, URA3 or URA4. In another embodiment, the selection marker is an antibiotic resistance marker that provides resistance to kanamycin, spectinomycin, streptomycin, ampicillin, carbenicillin, bleomycin, erythromycin, polymyxin, tetracycline, gentamycin or chloramphenicol. In certain embodiments, the selection marker of the recombinant MATa yeast strain is different than the selection marker of the recombinant MATalpha yeast strain.

In another embodiment, the second recombinant yeast strain overexpresses Aga1 and does not express the native sexual agglutination protein Sag 1. In an embodiment, the second recombinant yeast strain constitutively overexpresses Aga1 or inducibly overexpresses Aga1. In another embodiment, wherein the second recombinant yeast strain constitutively overexpresses Aga1 and the constitutive overexpression of Aga1 is regulated by a constitutively active promoter. In an embodiment, the second recombinant yeast strain is a MATalpha strain. Examples of constitutively active promoters include, but are not limited to, the ADH1 promoter, ADH2 promoter, ADH3 promoter, ADH4 promoter, ADH5 promoter, GAPDH1 promoter, GAPDH2 promoter, TEF1 promoter, TEF2 promoter, YEF3 promoter, CAM1 promoter, TEF4 promoter, EFB1 promoter, LEU promoter, PHO3 promoter, PHO5 promoter, PyK promoter, HIS4 promoter, CUP1 promoter, or ACO1 promoter. In some embodiments, the recombinant MATalpha yeast strain inducibly overexpresses Aga1 and the inducible overexpression of Aga1 is regulated by an inducible promoter. Examples of inducible promoters include, but are not limited to, the GAL1 promoter, GAL2 promoter, GAL3 promoter, GAL4 promoter, GAL80 promoter, AOX promoter, FDH promoter PGK promoter or FLD1 promoter. In certain embodiments, endogenous Aga1 is replaced with exogenous Aga1 regulated by a constitutively active promoter or an inducible promoter.

In certain embodiments, the second recombinant yeast strain is a budding yeast selected from *Pichia pastoris* and *Saccharomyces cerevisiae*.

In other embodiments, the second recombinant yeast strain comprises an exogenous recombinase, wherein the second recombinant yeast strain inducibly express the exogenous recombinase. In an embodiment, the inducible expression of the exogenous recombinase is regulated by a transcription factor, and wherein the transcription factor is constitutively expressed in the first recombinant yeast strain and requires an additional molecule to activate expression from the inducible promoter. A non-limiting example of a recombinase is CRE recombinase.

In an embodiment, the second recombinant yeast strain comprises at least one selection marker, wherein the selection marker can be an auxotrophic marker or an antibiotic marker. In some embodiments, the selection marker is an auxotrophic marker selected from ADE1, ADE2, CAN1, HIS3, LEU2, LYS2, TRP1, TRPS, URA3 and URA4. In another embodiment, the selection marker is an antibiotic resistance marker that provides resistance to kanamycin, spectinomycin, streptomycin, ampicillin, carbenicillin, bleomycin, erythromycin, polymyxin, tetracycline, gentamycin or chloramphenicol. In certain embodiments, the selection marker of the second recombinant yeast strain is different than the selection marker of the first recombinant yeast strain.

In another aspect, the disclosure provides a first nucleic acid construct comprising:
  (i) a homology arm at the 5' end of the nucleic acid construct,
  (ii) a first expression cassette comprising a gene coding for a first SAP,
  (iii) a second expression cassette comprising a first marker,
  (iv) a unique primer binding site,
  (v) a unique nucleic acid barcode,
  (vi) a recombination site, and
  (vii) a homology arm at the 3' end of the nucleic acid construct.

In an embodiment of the first nucleic acid construct, the first marker is an auxotrophic marker or an antibiotic marker. In another embodiment the first nucleic construct comprises a third expression cassette comprising a second marker, wherein the second marker is a fluorescent marker.

In an embodiment, the first nucleic acid cassette is integrated into the genome of the recombinant first recombinant yeast strain. In certain embodiments, the 5' and 3' homology arms of the nucleic acid construct facilitate homologous pairing between the nucleic acid construct and a genomic target region resulting in the nucleic acid construct being introduced into the genomic target region (for example, chromosome III).

In certain embodiments, the unique barcode is specific to the synthetic adhesion protein of the expression cassette.

In some embodiments, the recombination site is a lox site. Examples of lox sites include, but are not limited to loxP, lox66, lox71, lox511, lox5171, lox2272, M2, M3, M7, and M11.

In certain embodiments, the disclosure provides for a vector comprising the first nucleic acid construct, wherein the vector comprises a high copy origin of replication and a resistance gene. In some embodiments, the vector comprises a bacterial high copy origin of replication.

In yet another aspect, the disclosure provides a second nucleic acid construct comprising;
  (i) a homology arm at the 5' end of the nucleic acid construct,
  (ii) a first expression cassette comprising a gene coding for a second SAP,
  (iii) a second expression cassette comprising a first marker,
  (iv) a unique primer binding site,
  (v) a unique nucleic acid barcode,
  (vi) a recombination site, and
  (vii) a homology arm at the 3' end of the nucleic acid construct.

In an embodiment of the second nucleic acid construct, the first marker is an auxotrophic marker or an antibiotic marker. In another embodiment of the second nucleic acid construct, the second nucleic acid construct comprises a third expression cassette comprising a second marker, wherein the second marker is a fluorescent marker.

In some embodiments, the second nucleic acid construct integrated into the genome of the recombinant second recombinant yeast strain. In other embodiments, the second nucleic acid construct is integrated into a MATalpha yeast strain. In certain embodiments, the 5' and 3' homology arms of the nucleic acid construct facilitate homologous pairing between the nucleic acid construct and a genomic target region resulting in the nucleic acid construct being introduced into the genomic target region (for example, chromosome III).

In certain embodiments, the unique barcode is specific to the synthetic adhesion protein of the expression cassette.

In some embodiments, the recombination site is a lox site. Examples of lox sites include, but are not limited to loxP, lox66, lox71, lox511, lox5171, lox2272, M2, M3, M7, and M11.

In certain embodiments, the disclosure provides for a vector comprising the second nucleic acid construct, wherein the vector comprises a high copy origin of replication and a resistance gene. In some embodiments, the vector comprises a bacterial high copy origin of replication.

In some embodiments, the first marker of both the first and second nucleic acid constructs is an auxotrophic marker; wherein the auxotrophic marker of the first nucleic acid construct is different than the auxotrophic marker of the second nucleic acid construct.

In another embodiment, the fluorescent marker of the first nucleic acid construct is different than the fluorescent marker of the second nucleic acid construct.

In certain embodiments, the genomic target of the first nucleic acid construct and the second nucleic acid construct is on the same chromosomal locus.

In yet another embodiment, the unique primer binding site of the first nucleic acid construct and the unique primer binding site of the second nucleic acid construct are integrated into the same chromosome and after mating and chromosomal translocation the primer binding sites can be used to amplify a target nucleotide sequence comprising both the unique barcode of the first nucleic acid construct and the unique barcode of the second nucleic acid construct. In an embodiment, the unique barcode of the first nucleic acid construct and the unique barcode of the second nucleic acid construct are integrated into the same chromosomal locus and after mating and chromosomal translocation are within about 5,000, 4,000, 3,000, 2,000, 1,000, 900, 800, 700, 600, 500, 400, 300, 200 or 100 base pairs.

One of skill in art would appreciate that the methods and compositions disclosed herein can be used, for example, in characterizing protein-protein interaction networks, screening drug candidates for protein-protein interaction disruption, detecting extracellular targets, or understanding mating dependent biological processes such as speciation and ecosystem dynamics, screening drug candidates for their specific disruption of protein-protein interactions, performing toxicology screens of drug candidates on libraries of protein interactions that are indicative of toxicity, and screening antibody libraries for specific binding to a particular protein.

Exemplary Aspects

Below are examples of specific aspects for carrying out the present invention. The examples are offered for illustrative purposes only, and are not intended to limit the scope of the present invention in any way. Efforts have been made to ensure accuracy with respect to numbers used (e.g., amounts, temperatures, and the like), but some experimental error and deviation should, of course, be allowed for.

Example 1. Yeast Surface Display for Library-on-Library Characterization of Protein Interactions Construction of a yeast-mating assay for screening and/or determining protein-protein interactions and protein interaction networks. A flow-cytometry assay can be used to differentiate between MATa, MATalpha, and diploid cells. The native yeast sexual agglutinins have been replaced with surface displayed binders (SAPs), and mating efficiency was measured using flow-cytometry. A diploid chromosomal translocation system was developed to combine the genes for both binders onto a single chromosome such that next generation sequencing can be used to evaluate the mating frequency of a particular pair of binders in a large library.

While there are numerous cell-based assays to analyze extracellular binding between a library of proteins and a single target, only cell-free approaches have been developed for characterizing whole protein interaction networks in a single assay. This has meant time consuming and costly library preparation steps involving the purification and labeling of each protein constituent in the network. This example demonstrates a pairwise yeast surface display (PYSD) assay for library-on-library characterization of protein interactions that combines yeast surface display and sexual agglutination to link protein binding to the mating of S. cerevisiae. In particular, this example demonstrates that sexual agglutination is highly engineerable by knocking out the native agglutination proteins and instead displaying complementary binding proteins (synthetic agglutination proteins, SAPs) on the surface of MATa and MATalpha yeast cells. This example shows that mating efficiency is highly dependent on the binding affinity and expression level of the surface expressed proteins. A chromosomal translocation scheme can allow protein-protein interaction networks to be analyzed with next generation sequencing and applied to the analysis of two engineered protein interaction networks.

The characterization of protein interaction networks for both binding affinity and specificity is crucial for understanding cellular functions, screening therapeutic candidates, and evaluating engineered protein networks. For example, protein "interactome" mapping has expanded the understanding of biological systems and disease states and can be used to evaluate therapeutic drug candidates for the proper mediation or disruption of specific protein interactions. Additionally, the construction of synthetic systems often requires highly specific and orthogonal protein interactions to properly control cellular behavior. Engineered protein binding domains that allow for the construction of arbitrary protein interaction networks require careful characterization in the context of a highly complex biological system.

Many approaches exist for the analysis of binding between a library of proteins and a single protein target. Yeast surface display (YSD) has been widely used, in part due to the ease of library construction. In order to analyze protein networks, however, it is necessary to screen for binding between all possible protein pairs. Since YSD measures binding with cell fluorescence following incubation with soluble fluorescently tagged target, this approach does not allow for screening against a library of target proteins. A recently developed approach uses DNA barcoded proteins for one-pot library-on-library characterization, but requires the purification of each constituent protein in the network, making the analysis of large networks enormously time consuming and expensive. This disclosure presents a novel method that combines the ease of YSD library generation with a high throughput assay capable of characterizing entire protein interaction networks in a single pot.

A pairwise yeast surface display (PYSD) platform is used for one-to-one, many-to-one, or many-to-many protein interaction characterization. For a one-to-one screen, two isogenic displayer strains, one MATa constitutively expressing a fluorescent marker (e.g., mCherry) and one MATalpha constitutively expressing a second fluorescent marker (e.g., mTurquoise), each express a synthetic adhesion protein (SAP) on their surface as a fusion to Aga2 (Aga2-myc). A mating assay is then used to determine the effect of displaying those particular SAPs on mating efficiency, which is reported as the percent of diploid cells after 17 hours. Haploids and diploids are distinguished based on their expression of mCherry and mTurquoise in a flow cytometry assay. The surface expression strength of each SAP is determined by incubating the mixed culture with FITC conjugated anti-myc antibody prior to flow cytometry.

For a many-to-one or many-to-many screen, one or both of the isogenic displayer strains are replaced with a display library, or a library of displayer cells each expressing a unique SAP. After a short mating period, cells are transferred to media lacking lysine and leucine, which is used to select for diploid cells only. For a many-to-many screen, β-Estradiol (βE) is also added to induce CRE recombinase expression in mated diploids. Recombinase expression results in translocation at lox66/lox71 sites, which flank the SAP integrations, resulting in the juxtaposition of the SAP genes onto one copy of chromosome III. Because of the biased nature of the lox66/71 recombinase site pair, the majority of the population now consists of translocated diploids. Following translocation, cell lysis no longer uncouples the SAP pair from a particular diploid cell. For both the many-to-one and many-to-many screens, a colony PCR of the diploid population is analyzed with next generation sequencing to determine the mating frequency of each SAP pair compared to all other possible SAP pairs included in the assay (see FIG. 2A and FIG. 2B).

Materials and Methods:

PLASMID CONSTRUCTION: The plasmids used in Example 1 are listed in Table 1. For each construct, backbone and insert fragments were amplified with PCR, gel extracted, and assembled into plasmids using a Gibson reaction. Standard linkers between all parts increased the efficiency and consistency of cloning (see Example 5). All backbones, consisting of a high copy origin of replication and ampicillin resistance, were flanked with PmeI restriction sites for easy linearization and integration into the yeast chromosome. All plasmids contain approximately 500 bases of chromosomal homology upstream and downstream of the target locus. Knockout (KO) plasmids contain upstream and downstream chromosomal homology, but no gene cassette. The sequence of each promoter, open reading frame, terminator, and chromosomal homology were verified with Sanger sequencing.

TABLE 1

Plasmids used in Example 1.

| Plasmid Name | Gene Cassette | Marker | Integration Locus |
|---|---|---|---|
| pPYSD1 | Ura3KO | [5-FOA] | AGA1 |
| pPYSD2 | pGPD-mCherry | BleoMX | LTR2 |
| pPYSD3 | pGPD-mTurquoise | BleoMX | LTR2 |
| pPYSD4 | Aga2KO | URA | AGA2 |
| pPYSD5 | Sag1KO | URA | SAG1 |
| pPYSD6 | pGPD-Aga1 | NatMX | HIS3 |
| pPYSD7 | pGAL1-HygMX/pACT1-Zev4 | KanMX | YCR043 |
| pPYSD8 | pZ4-CRE/pGPD-GAVN | KanMX | YCR043 |
| pPYSD9 | pGPD-Aga2_Bfl1/lox66/mCherry | Trp1 | ARS314 |
| pPYSD10 | pGPD-Aga2_BclB/lox66/mCherry | Trp1 | ARS314 |
| pPYSD11 | pGPD-Aga2_Bcl2/lox66/mCherry | Trp1 | ARS314 |
| pPYSD12 | pGPD-Aga2_BHRF1/lox66/mCherry | Trp1 | ARS314 |
| pPYSD13 | pGPD-Aga2_Bim-BH3/lox71/mTurquoise | Trp1 | ARS314 |
| pPYSD14 | pGPD-Aga2_BINDI-F21/lox71/mTurquoise | Trp1 | ARS314 |
| pPYSD15 | pGPD-Aga2_BINDI-B+/lox71/mTurquoise | Trp1 | ARS314 |
| pPYSD16 | pGPD-Aga2_BINDI-2+/lox71/mTurquoise | Trp1 | ARS314 |
| pPYSD17 | pGPD-Aga2_BINDI-N62S/lox71/mTurquoise | Trp1 | ARS314 |

YEAST STRAIN CONSTRUCTION AND GROWTH CONDITIONS: The *S. cerevisiae* strains used in Example 1 are listed in Table 2. EBY100a and W303αMOD were used as initial parent strains. EBY100α was generated through the mating of these two parent strains followed by sporulation and tetrad screening for the appropriate selectable markers. All other strains were constructed with chromosomal integrations by linearizing a given plasmid with a Pme 1 restriction digest and conducting a standard LiAc transformation procedure. Selection of transformants was accomplished using media deficient in a given auxotrophic marker or with media supplemented with a eukaryotic antibiotic. Diagnostic colony PCRs were conducted following each transformation to verify integration into the proper locus. All yeast assays use standard yeast culture media and growth at 30° C. All liquid culture growth is performed in 3 mL of YPD liquid media and shaking at 275 RPM.

TABLE 2

Yeast strains used in Example 1.

| Strain Name | Description | Parent | Transformant |
|---|---|---|---|
| EBY100a | Yeast surface display strain | | |
| W303αMOD | MATα for generation of EBY100α | | |
| EBY100α | MATα version of yeast surface display strain | Mating of EBY100a and W303αMOD | |
| EBY101a | URA knockout with 5-FOA selection | EBY100a | |
| EBY101α | URA knockout with 5-FOA selection | EBY100α | |
| EBY102a | Constitutive expression of Aga1 | EBY101a | pMOD_NatMX_HIS_pGPD-Aga1 |
| EBY102α | Constitutive expression of Aga1 | EBY101α | pMOD_NatMX_HIS_pGPD-Aga1 |
| WTa_mCher | MATa, Consttutive mCherry expression with WT SAG1 | EBY102a | pMOD_BleoMX_LTR2_pGPD-mChe |
| WTα_mTur | MATα, Consttutive mTurquoise expression with WT SAG1 | EBY102α | pMOD_BleoMX_LTR2_pGPD-mTur |
| EBY103a | MATa, Sag1 knockout | EBY102a | pYMOD_URA_KO_SAG1 |
| EBY103α | MATα, Sag1 knockout | EBY102a | pYMOD_URA_KO_SAG1 |
| Δsag1α_mTur | MATα, Consttutive mTurquoise expression with SAG1 KO | EBY103α | pMOD_BleoMX_LTR2_pGPD_mTur |
| EBY104a | MATa, CRE recombinase part A | EBY103a | pYMOD_KanMX_YCR043_pZ4-CRE |
| EBY104α | MATα, CRE recombinase part B | EBY103α | pYMOD_KanMX_YCR043_pACT1-ZEV4 |
| yNGYSDa | Final MATa parent strain, with Sce1 landing pad | EBY104a | pYMOD_BleoMX_ARS314_pGAL-Sce1 |
| yNGYSDα | Final MATα parent strain, with Sce1 landing pad | EBY104α | pYMOD_BleoMX_ARS314_pGAL-Sce1 |
| yNGYSDa_Bfl1 | MATa haploids used in pairwise and batched mating assays | yNGYSDa | pNGYSDa_Bfl1 |
| yNGYSDa_BclB | | yNGYSDa | pNGYSDa_BclB |
| yNGYSDa_Bcl2 | | yNGYSDa | pNGYSDa_Bcl2 |
| yNGYSDa_BclW | | yNGYSDa | pNGYSDa_BclW |
| yNGYSDa_BclXL | | yNGYSDa | pNGYSDa_BclXL |
| yNGYSDa_Mcl1[151-321] | | yNGYSDa | pNGYSDa_Mcl1[151-321] |
| yNGYSDα_Bim.BH3 | MATα haploids used in pairwise and batched mating assays | yNGYSDα | pNGYSDα_Bim.BH3 |
| yNGYSDα_Noxa.BH3 | | yNGYSDα | pNGYSDα_Noxa.BH3 |
| yNGYSDα_Puma.MH3 | | yNGYSDα | pNGYSDα_Puma.BH3 |
| yNGYSDα_Bad.BH3 | | yNGYSDα | pNGYSDα_Bad.BH3 |

TABLE 2-continued

Yeast strains used in Example 1.

| Strain Name | Description | Parent | Transformant |
| --- | --- | --- | --- |
| yNGYSDα_Bik.BH3 | | yNGYSDα | pNGYSDα_Bik.BH3 |
| yNGYSDα_Hrk.BH3 | | yNGYSDα | pNGYSDα_Hrk.BH3 |
| yNGYSDα_Bmf.BH3 | | yNGYSDα | pNGYSDα_Bmf.BH3 |
| yNGYSDα_FINDI-F21 | | yNGYSDα | pNGYSDα_FINDI-F21 |
| yNGYSDα_FINDI-F30D | | yNGYSDα | pNGYSDα_FINDI-F30D |
| yNGYSDα_BINDI-B+ | | yNGYSDα | pNGYSDα_BINDI-B+ |
| yNGYSDα_BINDI-BCDP01 | | yNGYSDα | pNGYSDα_BINDI-BCDP01 |
| yNGYSDα_BINDI-B40A | | yNGYSDα | pNGYSDα_BINDI-B40A |
| yNGYSDα_2INDI-2+ | | yNGYSDα | pNGYSDα_2INDI-2+ |
| yNGYSDα_2INDI-4LVT | | yNGYSDα | pNGYSDα_2INDI-4LVT |
| yNGYSDα_WINDI-aBclW | | yNGYSDα | pNGYSDα_WINDI-aBCLW |
| yNGYSDα_XINDI-XCDP07 | | yNGYSDα | pNGYSDα_XINDI-XCDP07 |
| yNGYSDα_MINDI | | yNGYSDα | pNGYSDα_MINDI |

MATING ASSAYS: To evaluate the mating efficiency between any two yeast strains in liquid culture, haploid strains were initially grown to saturation, or for approximately 18 hours, from an isogenic colony on a fresh YPD plate. Each haploid was then combined in a fresh 3 mL YPD liquid culture such that the MATa strain was at a density of 100 cells/μL and the MATa strain was at a density of 600 cells/μL. This difference in starting concentration was an adjustment for an observed uneven growth response to mating factor. The cells were also each grown separately in fresh YPD in order to individually assess their surface expression strength. Following 17 hours of growth, 2.5 μL of mating culture was added to 1 mL of molecular grade water and read on a flow cytometer. MATa, MATalpha, and diploid cells were distinguished based on fluorescent intensity of mCherry and mTurquoise. For the experiments described here, a Miltenyi MACSQUANT® VYB was used. The Y2 channel (561 nm excitation laser and 615 nm emission filter) was used to measure mCherry expression and the V1 channel (405 nm excitation laser and 450 nm emission filter) was used to measure mTurquoise expression. The diploid cell population as a percent of total cell population after 17 hours was used as a measure of mating efficiency. Surface expression strength was measured by incubating 10 4 of each individually grown cell strain for 15 minutes with FITC conjugated anti-myc antibody in PBSF following a wash in 1 mL of water. Cells were then washed again and resuspended in 1 mL of water. Flow cytometry was then performed. For the determination of surface expression strength, an ACCURI™ C6 cytometer was used. The FL1.A channel (488 nm excitation laser and 533 nm emission filter) was used to measure FITC binding to the cell. FLOWJO™ is used for all cytometry analysis.

For a one-to-many batched mating assay, a recombinant MATa yeast strain expressing a single SAP fused to Aga2 is combined in a fresh 3 mL YPD culture with multiple recombinant MATalpha yeast strains expressing distinct SAPs fused to Aga2. The MATa strain is added at a density of 100 cells/μL and the MATalpha strains are added in equal concentrations for a total density of 600 cells/μL. After 6 hours of growth, hygromycin is added at 100 ng/μL. 20 hours after the initial culture inoculation, 1 mL of cells are pelleted. 2 μL of cells are removed from the pellet, lysed with 0.2% SDS, spun down to remove all cellular debris, and diluted in water. The lysate is then used as a template for a PCR with standard primers containing overhangs for next generation sequencing and the PCR product, expected to be approximately 350 bases, is purified from a gel slice. Single-read next generation sequencing is then performed. The frequency that a particular barcode is observed relative to the total number of reads provides a relative measure for the number of matings that were caused by the SAP associated with that particular barcode.

For a many-to-many (also see Example 6) batched mating assay, multiple haploid yeast strains of each mating type are combined in a fresh 3 mL YPD culture. The recombinant MATa yeast strains are added in equal concentrations for a total density of 100 cells/μL and the recombinant MATalpha yeast strains are added in equal concentrations for a total density of 600 cells/μL. After 6 hours of growth, hygromycin is added at 100 ng/μL and β-estradiol (βE) is added at 200 ng/μL. 20 hours after the initial culture inoculation, 1 mL of cells are pelleted. 2 μL of cells are removed from the pellet, lysed with 0.2% SDS, spun down to remove all cellular debris, and diluted in water. The lysate is then used as a template for a PCR with standard primers containing overhangs for next generation sequencing and the PCR product, expected to be 650 bases, is purified from a gel slice. Paired-end next generation sequencing is then performed. The frequency that a particular pair of barcodes is observed relative to the total number of reads provides a relative measure for the number of matings that were caused by the SAP pair associated with those two particular barcodes.

Results

Figure 3A:
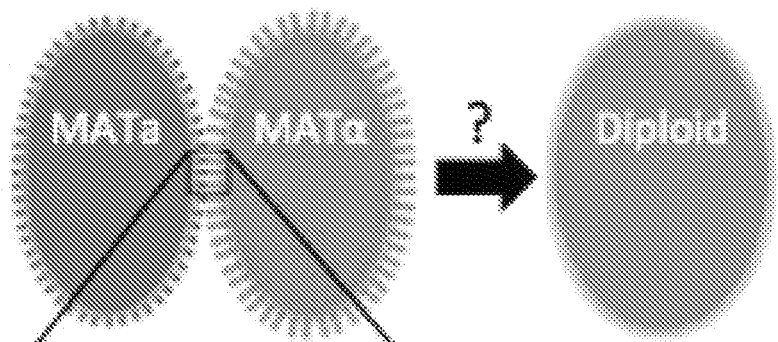
FIG. 3A-FIG. 3H show a general description of the recombinant yeast mating system in a turbulent liquid culture.
Figure 3B:
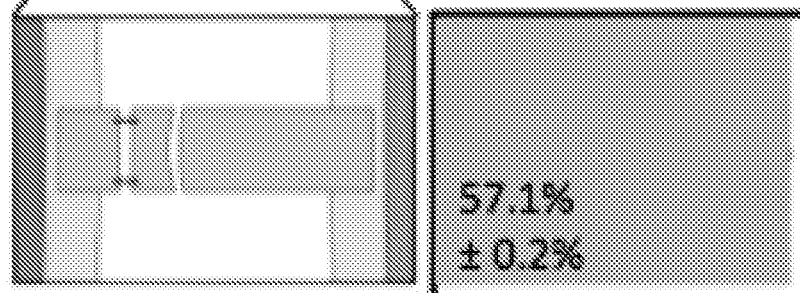
Figure 3C:
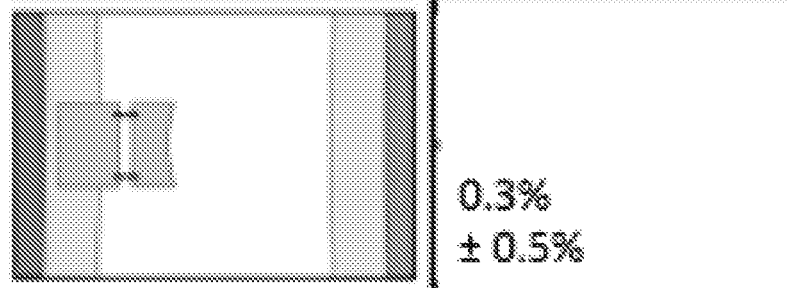
Figure 3D:
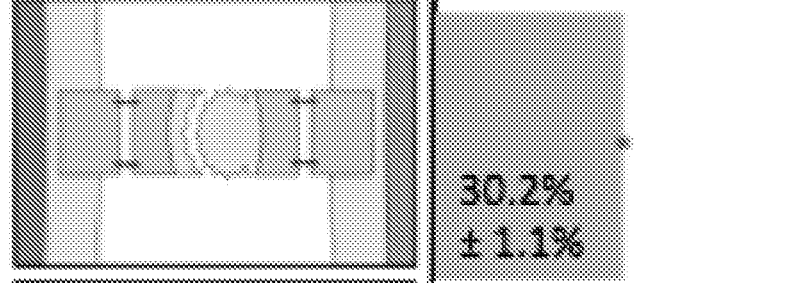
Figure 3E:
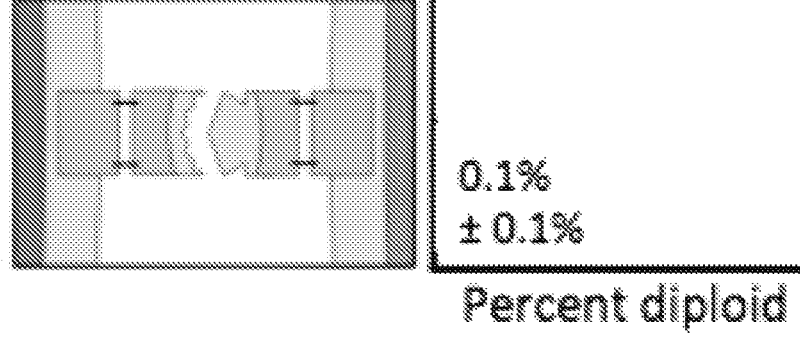
Figure 3F:
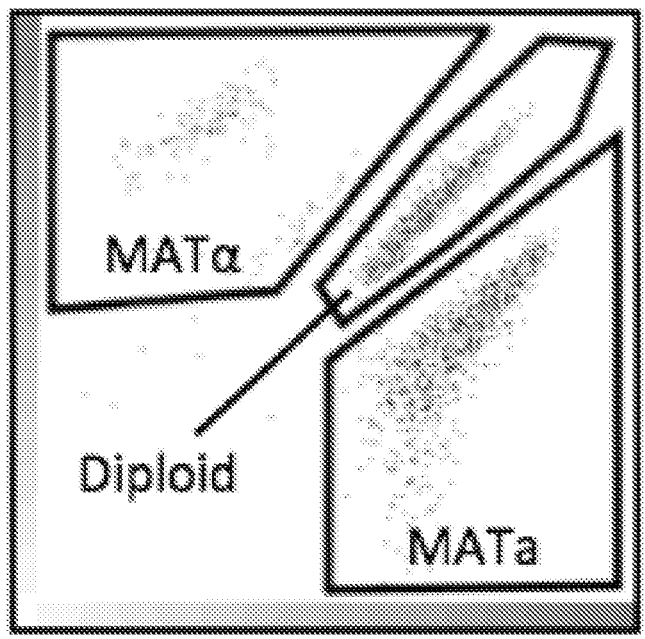
Figure 3G:
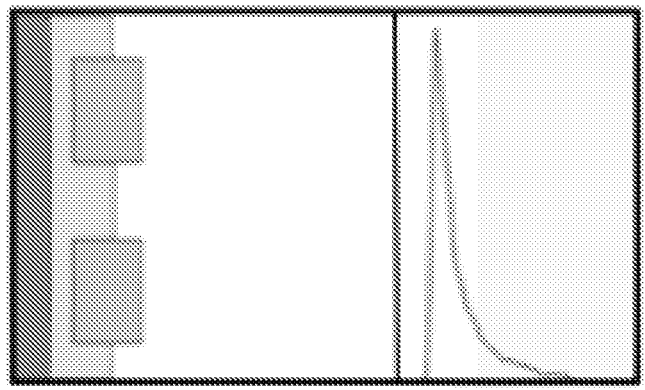
Figure 3H:
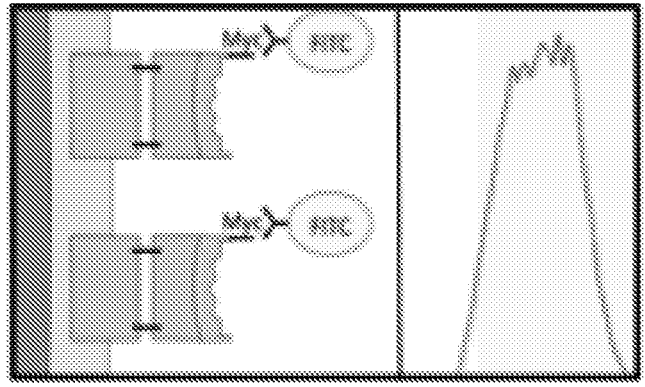

For S. cerevisiae haploid cells lacking an essential sexual agglutinin protein, binding is sufficient for the recovery of agglutination and mating in liquid culture. Sag1, the primary MATalpha sexual agglutinin protein, is essential for agglutination (FIG. 3B). When Sag1 is knocked out, MATalpha cells are unable to mate with wild-type MATa cells in a turbulent liquid culture (FIG. 3C). However, when complementary SAPs are expressed on a display pair, mating is recovered (FIG. 3D). Non-complementary SAPs are unable to recover mating (FIG. 3E).

Figure 4A:
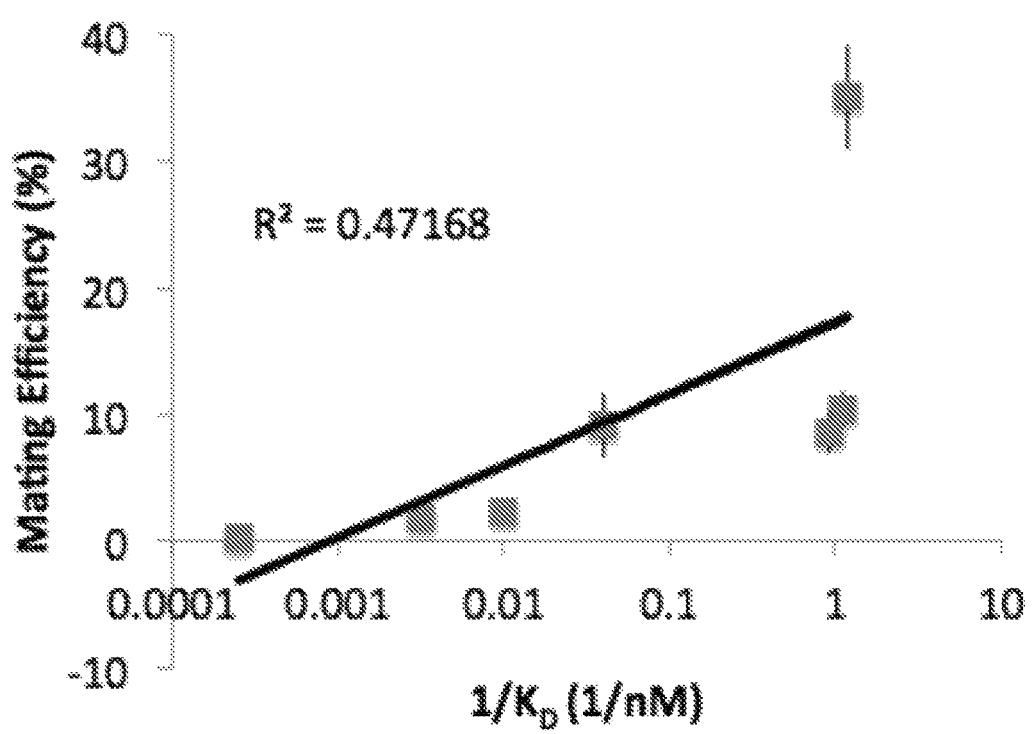
FIG. 4A shows a plot to determine the relationship between binding affinity, mating efficiency, and surface expression strength. Mating efficiency, in percent diploid formation, is plotted against the inverse of the dissociation constant, in nM. A logarithmic fit is shown.
Figure 4B:
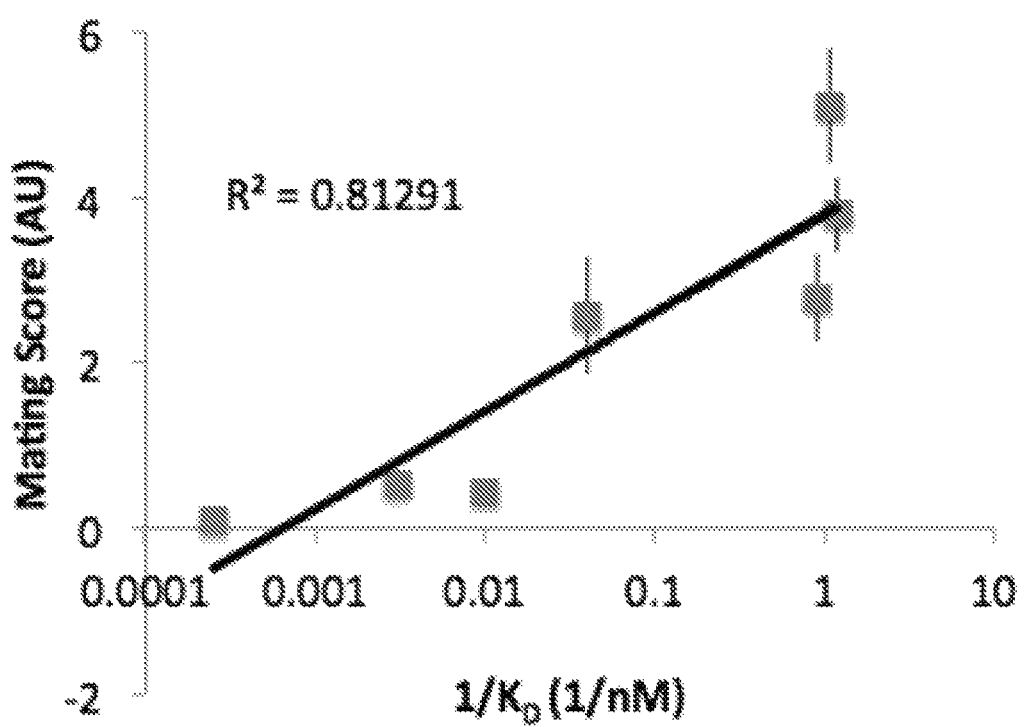
FIG. 4B shows a plot to determine the relationship between binding affinity, mating efficiency, and surface expression strength. Mating score is calculated by adjusting the observed mating efficiency for the surface expression strength, in arbitrary units, of both display strains in each pair. The result of this correction is an improved logarithmic fit.

The frequency of mating events between any two display cells is dependent on the binding affinity between their SAP pair and the surface expression strength of each SAP. The results demonstrate that binding affinity and observed mating efficiency are positively correlated (FIG. 4A). However, it is possible to improve the correlation by adjusting the mating efficiency for the expression level of each SAP (FIG. 4B).

Seven SAP pairs with known affinities were evaluated for mating efficiency (see Table 3). The mating efficiency for each pair was tested four times, and an average and standard deviation were calculated. The surface expression strength (SES) of each haploid display strain was also measured, as described in the materials and methods. A "mating score," which adjusts the mating efficiency for differences in surface expression strength, was calculated by dividing the mean mating efficiency by the product of the surface expression strengths of both haploid displayer strains.

TABLE 3

Results of SAP pairs with known affinities evaluated for mating efficiency.

| | F21 | F30D | B+ | B-CDP01 | B40A | 2+ | 4LVT | X-CDP07 | MINDI |
|---|---|---|---|---|---|---|---|---|---|
| AFFINITY (nM) | | | | | | | | | |
| Bfl1 | 1.00 | 1.14 | NA | 517.83 | 2379.33 | NA | NA | 7047.00 | 182444.33 |
| BclB | 31020.00 | 3829.67 | 24.67 | 8.33 | 76.86 | NA | 14730.00 | 106.83 | 21806.67 |
| Bcl2 | 320.97 | 100.21 | NA | 17.31 | 12460.00 | 0.84 | 8.93 | 3.81 | 15620.00 |
| BclXL | 891.33 | 537.27 | NA | 20.20 | 7777.00 | 3539.33 | 12120.00 | 0.59 | 342333.33 |
| BclW | 7402.00 | 3770.00 | NA | 2014.00 | 18963.33 | 1846.33 | 1668.67 | 14.89 | 224916.67 |
| Mcl1 | 1690.30 | 254.91 | NA | 0.46 | 3650.33 | NA | 38860.00 | 17.42 | 0.14 |
| AFFINITY (SD+) | | | | | | | | | |
| Bfl1 | 0.61 | 0.34 | NA | 28.85 | 853.78 | NA | NA | 564.30 | 289587.58 |
| BclB | 7900.93 | 1438.04 | 5.68 | 1.16 | 50.91 | NA | 3713.00 | 8.60 | 11570.10 |
| Bcl2 | 40.77 | 0.57 | NA | 3.46 | 385.88 | 0.56 | 1.32 | 1.03 | 2338.61 |
| BclXL | 216.45 | 20.96 | NA | 4.19 | 314.09 | 250.64 | 1278.01 | 0.07 | 11249.15 |
| BclW | 603.13 | 127.36 | NA | 504.92 | 2051.15 | 318.57 | 128.81 | 0.47 | 196399.98 |
| Mcl1 | 808.64 | 8.40 | NA | 0.09 | 122.07 | NA | 40474.79 | 1.29 | 0.06 |

Figure 2A:
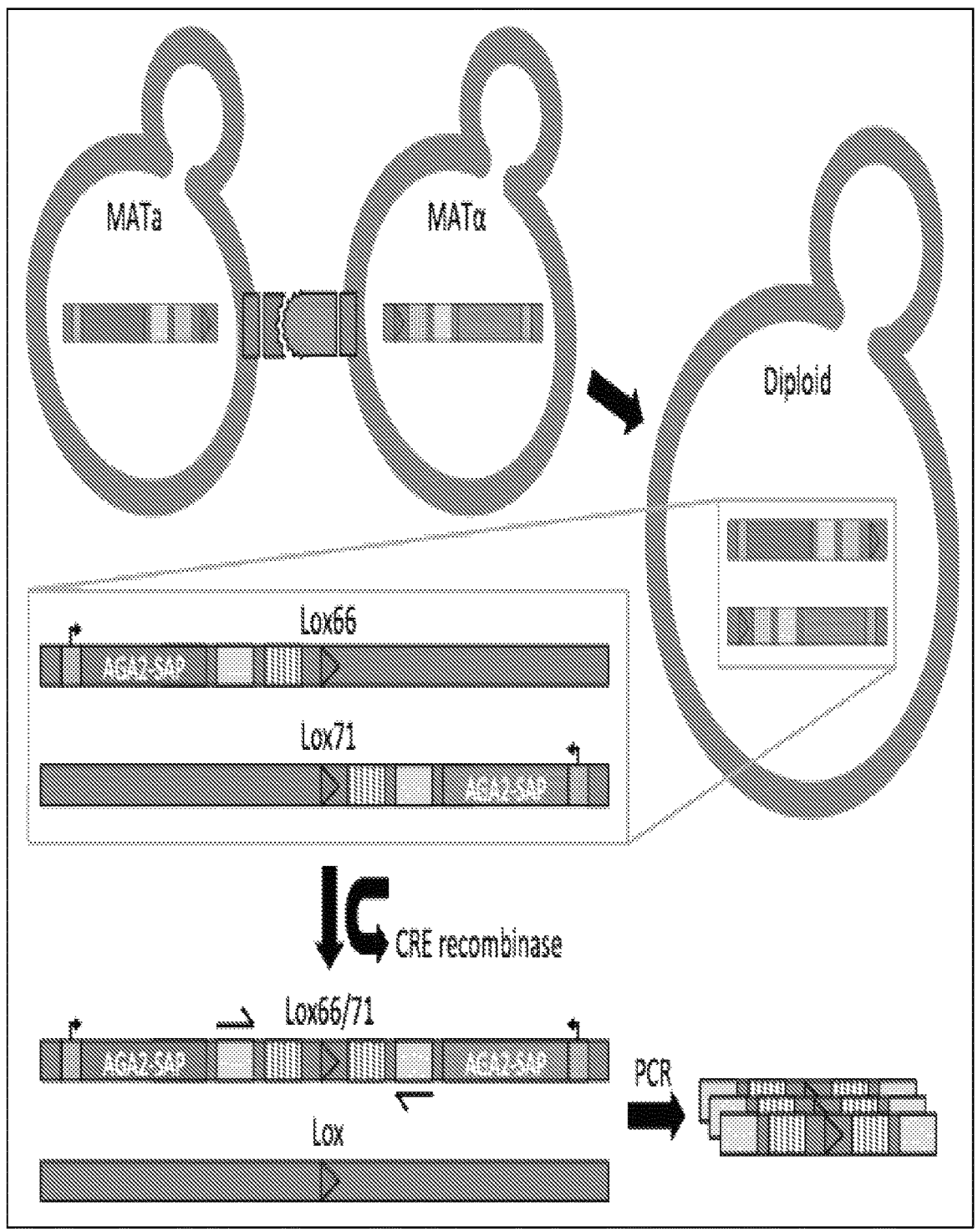
FIG. 2A shows a schematic of the CRE recombinase translocation scheme for high throughput analysis of display pair interactions. Here, a mating between a single recombinant MATa yeast strain and a single recombinant MATalpha yeast strain is shown. For a batched mating assay, however, a library of displayer cells of each mating type would be used (each comprising a library of SAPs fused to Aga2). Each MATa and MATalpha haploid cell contains a SAP fused to Aga2 integrated into a target chromosome (for example, chromosome III). Upon mating, both copies of the target chromosome are present in the same diploid cell. In addition to the SAP/Aga2 cassette, each copy of the target chromosome has a unique primer binding site, a unique barcode to the particular SAP, and a lox recombination site. Upon expression of CRE recombinase, a chromosomal translocation occurs at the lox sites, resulting in a juxtaposition of the primer binding sites and barcodes onto the same copy of the target chromosome. A colony PCR is then performed to amplify a region containing the barcodes from both SAPs. In a batched mating, the result is a pool of fragments, each containing the barcodes associated with two SAPs that were responsible for a mating event. Paired-end next generation sequencing is then used to match the barcodes and determine the relative frequencies of each interaction pair that caused a mating.
Figure 2B:
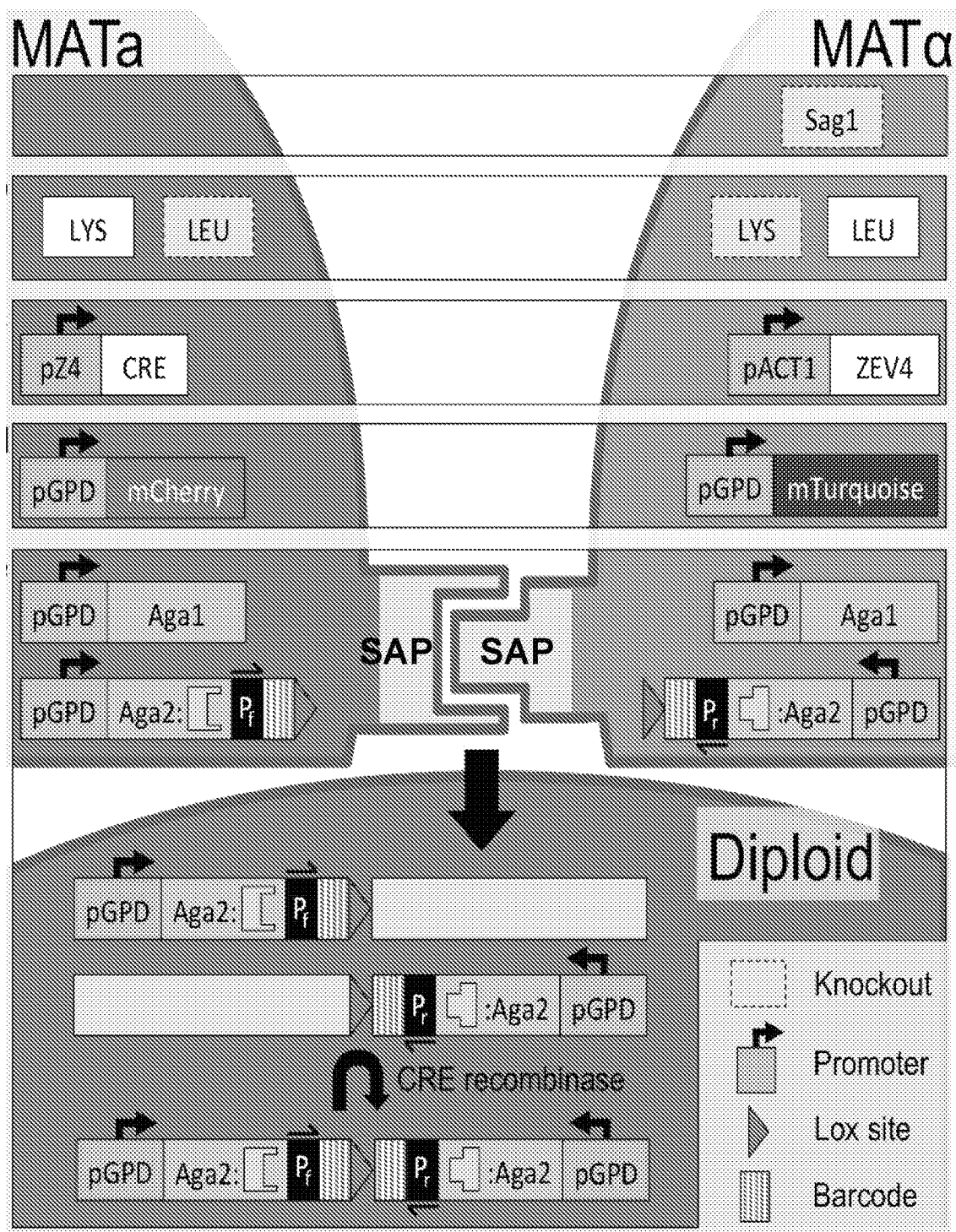
FIG. 2B shows another schematic of the CRE recombinase translocation scheme for high throughput analysis of display pair interactions. The α-agglutinin, Sag 1, is knocked out in MATα cells to eliminate native agglutination. MATa and MATalpha cells are able to synthesize lysine or leucine, respectively. Diploids can then be selected for in media lacking both amino acids. MATα cells express ZEV4, a βE inducible transcription factor that activates CRE recombinase expression in diploid cells. MATa and MATalpha cells express mCherry and mTurquoise, respectively, for identification of strain types with flow cytometry. MATa and MATalpha cells constitutively express Aga1 along with a barcoded SAP fused to Aga2. When CRE recombinase expression is induced in diploids with βE, a chromosomal translocation at lox sites consolidates both SAP-Aga2 fusion expression cassettes onto the same chromosome. A single fragment containing both barcodes is then amplified by PCR with primers annealing to $P_f$ and $P_r$ (primers specific to the primers from the first and second nucleic acid constructs integrated at the genomic target site) and sequenced to identify the interacting SAP pair.
Figure 5:
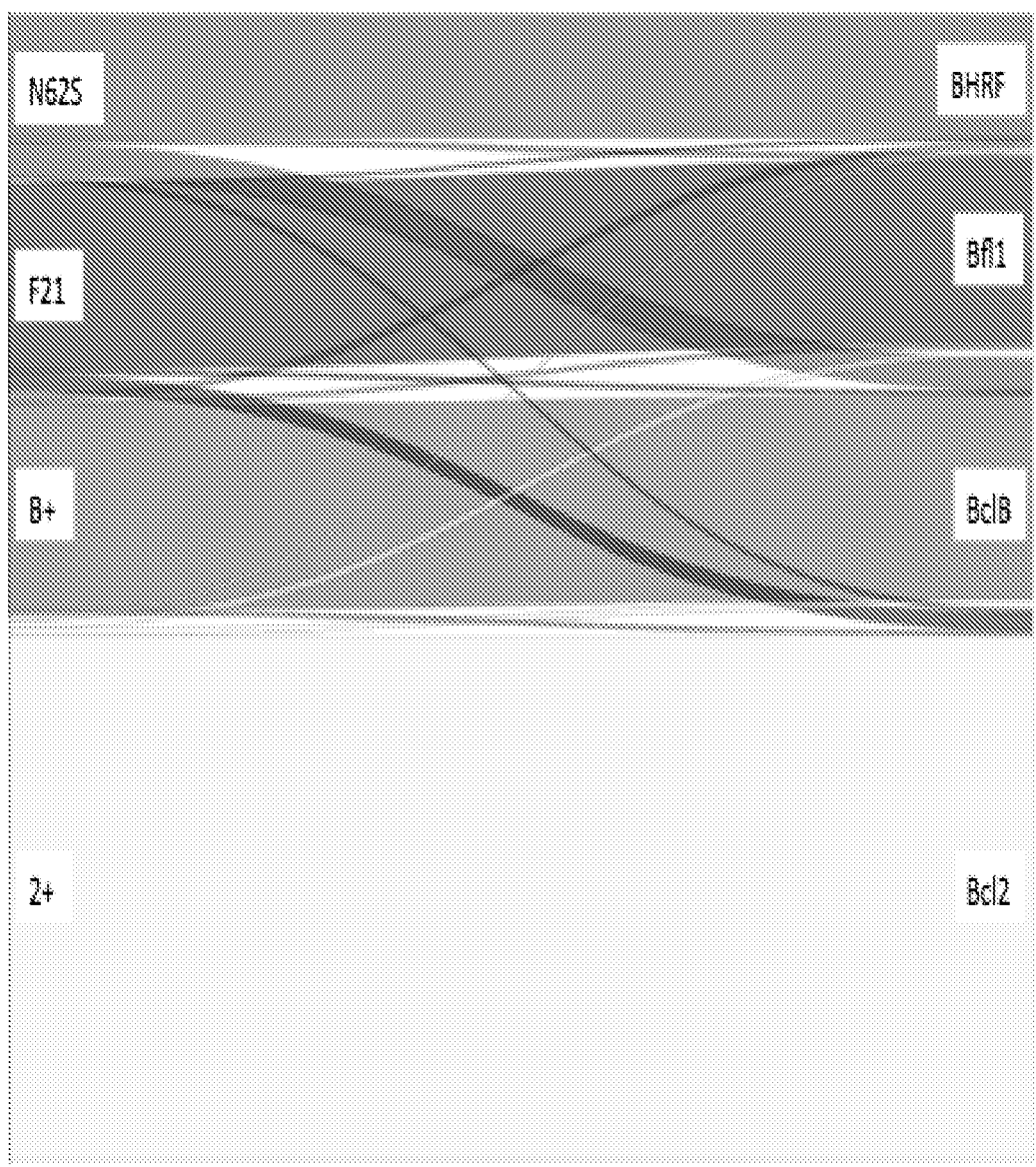
FIG. 5 shows a chord diagram showing the relative mating frequency between haploid cells expressing particular SAPs. The height of each chord indicates the relative number of diploids that are generated due to an interaction between the two connected proteins. This example diagram represents a mostly orthogonal protein topology in which each protein has a single primary binding partner.

From a batched mating, it is possible to determine the relative interaction strengths between many proteins in a single assay. By barcoding each SAP, a many-to-one screen can evaluate the relative mating frequencies between a particular SAP and a SAP library using single-read next generation sequencing. A CRE recombinase-based translocation scheme can be used to juxtapose the barcodes from each mating type onto the same chromosome (FIG. 2A). With the addition of this chromosomal translocation procedure, it is possible to evaluate relative mating frequencies between two SAP libraries using paired-end next generation sequencing. This approach allows for the analysis of arbitrary protein interaction topologies (see FIG. 5 for what exemplary results could look like).

Performing additional mating assays with more SAP pairs and using all measured affinities of the SAP pairs can provide the surface expression strength of each SAP and the mating efficiency. A statistical analysis can be performed to determine the relationship between binding affinity, surface expression strength of each SAP, and mating efficiency. The result could be used to determine a predictive relationship between these four variables so that measuring mating efficiency and surface expression strengths could be used to provide an estimation of binding affinity and to determine a threshold for a detectable recovery of mating efficiency.

This Example demonstrates a pairwise yeast surface display assay that allows for library-on-library characterization of protein interactions in a single assay. By replacing native S. cerevisiae sexual agglutinin proteins with synthetic adhesion proteins, it is possible to couple mating efficiency and protein binding strength. This approach can then be used to evaluate binding between two specific proteins or to determine the relative interactions strengths between a library of proteins.

Example 2. Detecting Extracellular Targets with an S. cerevisiae Mating Assay

Construction of a yeast-mating assay for the detection of extracellular substrates. A sterile haploid yeast display strain are constructed that can serve as a target. MATa and MATalpha strains can express binders complementary to the protein expressed by the sterile haploid strain. In the presence of the target, MATa and MATalpha cells are co-localized due to agglutination with the target. Flow cytometry can be used to evaluate mating efficiency in the presence and absence of target. Incremental steps are then taken to detect a more realistic pathogenic target, such as replacing the sterile haploid with an antigen-coated bead and then using progressively smaller beads. The system can be applied to the detection of clinically relevant targets such as pathogenic yeasts, bacteria, and viruses.

A generalizable cell-based platform for the extracellular detection of membrane-impermeable targets has remained an elusive goal for synthetic biologists. Most strategies for the development of cellular sensors involve two major challenges: extracellular signal initiation and signal transduction through the cell membrane. This example demonstrates a new approach called yeast surface detection (YS-detection) that links target binding directly to mating, eliminating the need for signal transduction through the membrane, in order to create a modular platform that can be used with any antigen binder. A YS-detection can be used to distinguish between the presence and absence of a wide range of extracellular targets. Specifically, engineered yeast strains can identify the presence of a mock pathogen, either an antigen-coated cell or bead, and that this response is highly specific to the particular target antigen. YS-detection can be multiplexed for the simultaneous detection of different mock pathogens in a single assay. The resulting platform is a modular cellular sensor chassis that can be used for the detection of a wide range of extracellular targets and provide a framework for the development of low cost cell-based diagnostic tools.

The development of faster, cheaper, simpler, and more accurate diagnostic devices has been a major focus of biomedical research, especially since a 2002 report found that the development of diagnostic platforms suitable for global health applications is one of the top ten most important needs for improving health in developing countries. Three main strategies are commonly considered for diagnostic platforms: imaging of samples with microscopy, nucleotide detection with PCR, and protein detection with antibody capture techniques. These strategies, however, require trained laboratory personnel, costly reagents, and the use of sophisticated equipment. Example 2 demonstrates a cell-based diagnostic approach that is automated, cheap, and equipment free.

The use of cells, and in particular S. cerevisiae, for a diagnostic platform has many distinct advantages over conventional approaches. Cells can be programmed such that entire process of signal detection, filtration, and amplification are done in a single tube without any requirements placed on the user. Looking at an example from nature, human immune cells are able to detect antigen presence within a complex environment and respond by inducing an immune response. Synthetic systems have been constructed that contain all necessary logic modules for signal detection, filtration, and output generation. The low cost and ease of growing S. cerevisiae means that cell-based diagnostics could be made available at a very low price and could be manufactured anywhere. Two other concerns for a global health diagnostic platform are shelf-life and stability in extreme temperatures. S. cerevisiae spores have been shown to maintain viability for years and withstand temperatures of up to 60° C. for over 20 minutes, which make them far hardier than the reagents required for most conventional diagnostic techniques.

Example 2 demonstrates a yeast surface detection (YS-detection) platform, in which pathogen presence is linked to the mating efficiency between two S. cerevisiae haploid strains. The system consists of a displayer strain pair, one MATa and one MATalpha, each expressing an identical synthetic adhesion protein (SAP) on its surface as a fusion to Aga2-myc. The displayer strains lack their native sexual agglutinin proteins, and are not able to undergo sexual agglutination when grown together. The result is a near zero mating efficiency in a turbulent liquid culture. The SAPs bind with high affinity and specificity to a particular antigen protein, such that presence of multivalent antigen induces agglutination and restores mating efficiency.

Figure 6:
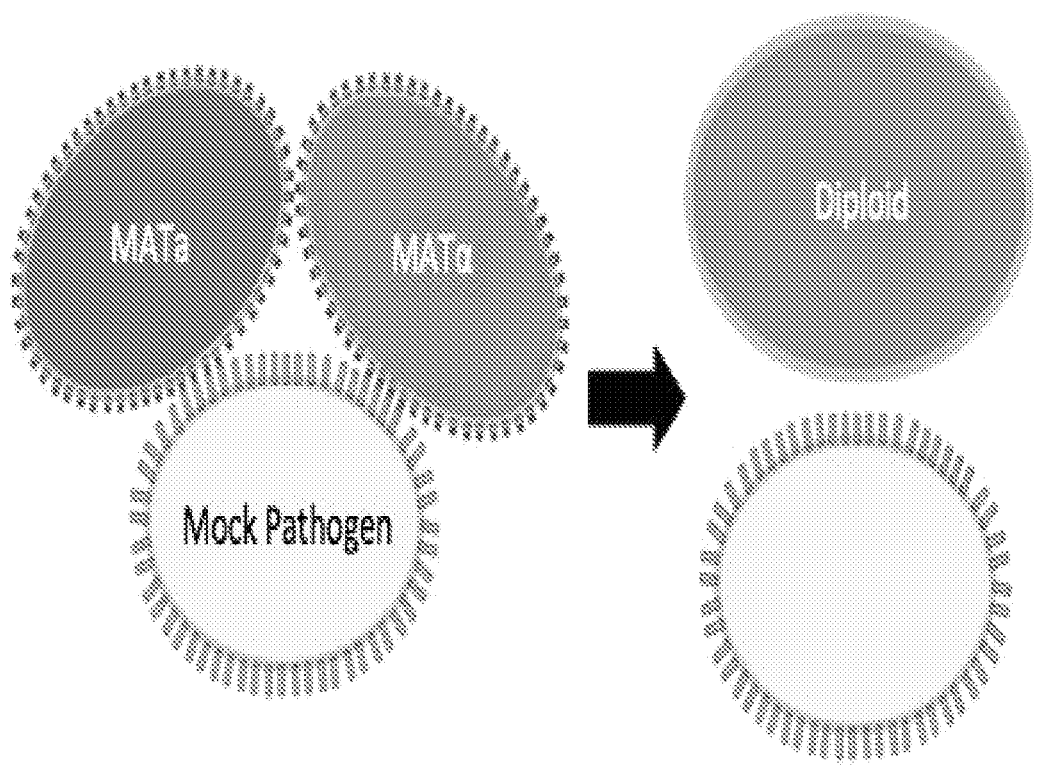
FIG. 6 shows a cartoon of the yeast surface detection method. A MATa display strain constitutively expressing mCherry and a MATalpha display strain constitutively expressing mTurquoise are mixed in liquid culture along with a mock pathogen yeast strain that is sterile due to the deletion of Ste5. The fluorescent markers make it possible to quantify mating efficiency using flow cytometry by identifying diploid cells that express both markers. While the MATa and MATalpha display strains do not directly bind to one another, agglutination is caused by both strains binding to the mock pathogen strain. Once the displayer strains are immobilized in close proximity to one another, mating is able to occur.

Testing of the system is conducted with a mock pathogen strain, or a sterile haploid yeast cell that is displaying antigen on its surface. Sterility is achieved by knocking out Ste5, a scaffold protein that is essential for the initiation of mating. Addition of mock pathogen expressing the complementary antigen to the displayer strain SAPs, or a complementary mock pathogen, can result in an increased mating efficiency (FIG. 6). Conversely, the addition of a non-complementary mock pathogen can have no effect on mating efficiency. The mock pathogen strains are replaced with antigen-coated beads, or mock pathogen beads, of various sizes and antigen densities to test the detection thresholds of the system. Multiplexing can be tested by combining multiple displayer strain pairs into a single pot and adding different combinations of the respective complementary mock pathogens or mock pathogen beads.

Materials and Methods

PLASMID CONSTRUCTION: The plasmids used in Example 2 are listed in Table 4. For each construct, backbone and insert fragments were amplified with PCR, gel extracted, and assembled into plasmids using a Gibson reaction. Standard linkers between all parts increased the efficiency and consistency of cloning (see Supplement 7.1). All backbones, consisting of a high copy origin of replication and ampicillin resistance, are flanked with Pme 1 restriction sites for easy linearization and integration into the yeast genome. All plasmids contain approximately 500 bases of chromosomal homology upstream and downstream of the target locus. Knockout (KO) plasmids contain upstream and downstream chromosomal homology, but no gene cassette. The promoter, open reading frame, terminator, and chromosomal homology of each plasmid were verified with Sanger sequencing.

TABLE 4

Plasmids used in Example 2.

| Plasmid Name | Gene Cassette | Marker | Integration Locus |
| --- | --- | --- | --- |
| pPYSD1 | Ura3KO | [5-FOA] | SAG1 |
| pPYSD2 | Ste5KO | URA | STE5 |
| pPYSD3 | pGPD-Aga2_Bim-BH3 | TRP1 | ARS314 |
| pPYSD4 | pGPD-Aga2_BINDI-B+ | TRP1 | ARS314 |
| pPYSD5 | pGPD-Aga2_BINDI-N62S | TRP1 | ARS314 |
| pPYSD6 | pGPD-Aga2_BINDI-2+ | TRP1 | ARS314 |
| pPYSD7 | pGPD-Aga2_BclB/mCherry | Trp1 | ARS314 |
| pPYSD8 | pGPD-Aga2_BHRF1/mCherry | Trp1 | ARS314 |
| pPYSD9 | pGPD-Aga2_Bcl2/mCherry | Trp1 | ARS314 |
| pPYSD10 | pGPD-Aga2_BclB/mTurquoise | Trp1 | ARS314 |
| pPYSD11 | pGPD-Aga2_BHRF1/mTurquoise | Trp1 | ARS314 |
| pPYSD12 | pGPD-Aga2_Bcl2/mTurquoise | Trp1 | ARS314 |

YEAST STRAIN CONSTRUCTION AND GROWTH CONDITIONS: The S. cerevisiae strains used in Example 2 are listed in Table 5. All strains were constructed with chromosomal integrations by linearizing a given plasmid with a Pme 1 restriction digest and conducting a standard LiAc transformation procedure. Selection of transformants was accomplished using media deficient in a given auxotrophic marker or with media supplemented with a eukaryotic antibiotic. Diagnostic colony PCRs were conducted following each transformation to verify integration into the proper locus. All yeast assays use standard yeast culture media and growth at 30° C. All liquid culture growth is performed in 3 mL of YPD liquid media and shaking at 275 RPM.

TABLE 5

Yeast strains used in Example 2.

| Strain Name | Genotype | Transformants |
| --- | --- | --- |
| EBY103α* | α GPD-AGA1::NatMX sag1::URA3 trp1 lys2 his3 pep4::HIS2 prb1Δ1.6R can1 GAL | |
| EBY103α-URA | α GPD-AGA1::NatMX sag1::ura3 trp1 lys2 his3 pep4::HIS2 prb1Δ1.6R can1 GAL | pPYSD1 |
| SterileYSD | α GPD-AGA1::NatMX sag1::URA3 trp1 lys2 his3 pep4::HIS2 prb 1Δ1.6R can1 GAL | pPYSD1, pPYSD2 |

TABLE 5-continued

Yeast strains used in Example 2.

| Strain Name | Genotype | Transformants |
|---|---|---|
| SterileYSD_Bim-BH3 | α GPD-AGA1::NatMX sag1::URA3 trp1 lys2 his3 pep4::HIS2 prb1Δ1.6R can1 GAL | pPYSD1, pPYSD2, pPYSD3 |
| SterileYSD_BINDI-B+ | α GPD-AGA1:NatMX sag1::URA3 trp1 lys2 his3 pep4::HIS2 prb 1Δ1.6R can1 GAL | pPYSD1, pPYSD2, pPYSD4 |
| SterileYSD_BINDI-N62S | α GPD-AGA1::NatMX sag1: :URA3 trp1 lys2 his3 pep4::HIS2 prb 1Δ1.6R can1 GAL | pPYSD1, pPYSD2, pPYSD5 |
| SterileYSD_BINDI-2+ | α GPD-AGA1::NatMX sag1::URA3 trp1 lys2 his3 pep4::HIS2 prb 1Δ1.6R can1 GAL | pPYSD1, pPYSD2, pPYSD6 |
| EBY104a* | a pGAL1-HygMX/Zev4::KanMX GPD-AGA1::NatMX aga2::URA3 trp1 leu2 his3 pep4::HIS2 prb 1Δ1.6R can1 GAL | |
| EBY104a_BclB_mCherry | a pGPD-AGA2_BclB_mCherry::TRP1 pGAL1-HygMX/Zev4::KanMX GPD-AGA1::NatMX aga2::URA3 trp1 leu2 his3 pep4::HIS2 prb 1Δ1.6R can1 GAL | pPYSD7 |
| EBY104a_BHRF1_mCherry | a pGPD-AGA2_BHRF1_mCherry::TRP1 pGAL1-HygMX/Zev4::KanMX GPD-AGA1::NatMX aga2::URA3 trp1_leu2 his3 pep4::HIS2 prb 1Δ1.6R can1 GAL | pPYSD8 |
| EBY104a_Bcl2_mCherry | a pGPD-AGA2_Bcl2_mCherry::TRP1 pGAL1-HygMX/Zev4::KanMX GPD-AGA1::NatMX aga2::URA3 trp1 leu2 his3 pep4::HIS2 prb 1Δ1.6R can1 GAL | pPYSD9 |
| EBY104α* | α pZ4-CRE/GAVN::KanMX GPD-AGA1::NatMX sag1::URA3 trp1 lys2 his3 pep4::HIS2 prb 1Δ1.6R can1 GAL | |
| EBY104α_BclB_mTurquoise | α pGPD-AGA2_BclB_mTurquoise::TRP1 pZ4-CRE/GAVN::KanMX GPD-AGA1::NatMX sag1::URA3 trp1 lys2 his3 pep4::HIS2 prb 1Δ1.6R can1 GAL | pPYSD10 |
| EBY104α_BHRF1_mTurquoise | α pGPD-AGA2_BHRF1_mTurquoise::TRP1 pZ4-CRE/GAVN::KanMX GPD-AGA1::NatMX sag1::URA3 trp1 lys2 his3 pep4::HIS2 prb 1Δ1.6R can1 GAL | pPYSD11 |
| EBY104α_Bcl2_mTurquoise | α pGPD-AGA2_Bcl2_mTurquoise::TRP1 pZ4-CRE/GAVN::KanMX GPD-AGA1::NatMX sag1::URA3 trp1 lys2 his3 pep4::HIS2 prb 1Δ1.6R can1 GAL | pPYSD12 |

MATING ASSAYS: To test for the detection of a mock pathogen, a display strain pair and one or more mock pathogen yeast strains are initially grown to saturation, or for approximately 18 hours, from isogenic colonies on a fresh YPD plate. The two displayer strains are then combined in a fresh YPD liquid culture such that the MATa strain is at a density of 100 cells/μL and the MATalpha strain is at a density of 600 cells/μL. This difference in starting concentration is an adjustment for the uneven growth response to mating factor. A mock pathogen strain expressing a protein complementary to that of the display pair SAP is also added to the culture at this time. The concentration at which the mock pathogen strain is added depends on the nature of the assay. Control matings are also performed that lack any mock pathogen and that contain mock pathogen expressing a non-complementary SAP. Following 17 hours of growth, 2.5 μL of mating culture is added to 1 mL of molecular grade water and read on a flow cytometer. MATa, MATalpha, and diploid cells are distinguished based on fluorescent intensity of mCherry and mTurquoise. For the experiments described here, a Miltenyi MACSQUANT® VYB was used. The Y2 channel (561 nm excitation laser and 615 nm emission filter) is used to measure mCherry expression and the V1 channel (405 nm excitation laser and 450 nm emission filter) is used to measure mTurquoise expression. The diploid cell population as a percent of total cell population after 17 hours is used as a measure of mating efficiency. For binary mating assays, hygromycin is added 5 hours after the initial mating inoculation and cultures are grown for a total of 48 hours. FLOWJO™ is used for all cytometry analysis.

Results

A sterile yeast surface display strain with a ste5 deletion was constructed. Ste5 is a scaffold protein that is essential for initiation of the mating pathway MAPK cascade. Although it contains the MATalpha gene, it has been shown that even when this strain expresses a SAP complementary to that of a MATa strain, its mating efficiency is zero. This sterile yeast strain will serve as the chassis for a mock pathogen.

Adding a selection for diploids early in the mating can generate a binary output, and likely can generate a binary output to mock pathogen presence. All MATa display strains contain a hygromycin resistance gene under a very weak promoter and all MATalpha display strains constitutively express a transcriptional activator specific to the weak promoter. Adding hygromycin 5 hours after the initial mating results in saturation for a display pair expressing complementary SAPs and no growth for a display pair expressing non-complementary SAPs.

Figure 7:
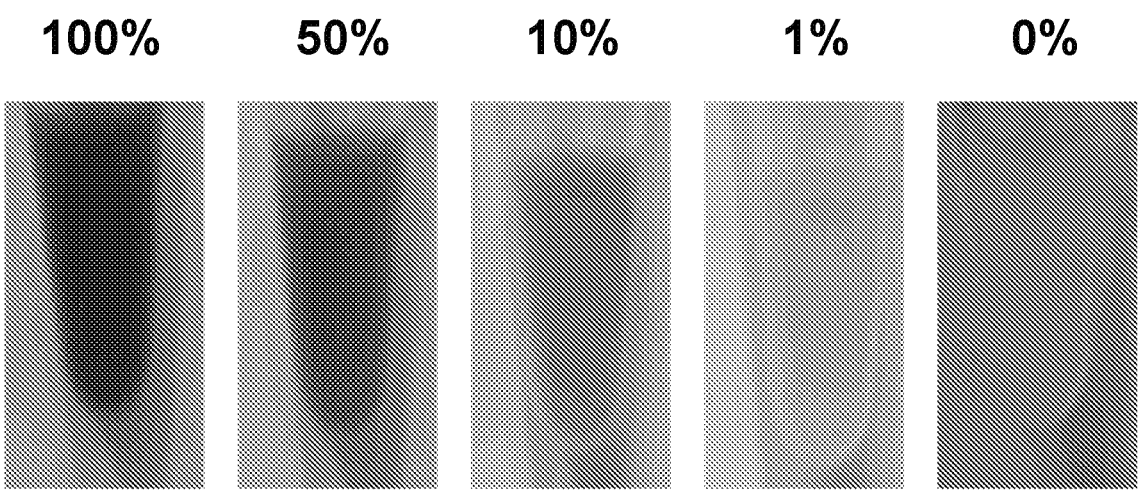
FIG. 7 shows the visual detection of β-galactosidase producing cells. A diploid *S. cerevisiae* strain was constructed that constitutively produces β-galactosidase. The images show the color change with different ratios of the β-galactosidase producing strain and a wild-type strain. A culture of the β-galactosidase producing strain and a wild-type strain were separately grown to saturation. For each screen, a total of 50 µL of saturated culture was removed washed, lysed and incubated with x-gal for 18 hours before imaging. Of the 50 µL, the percent of β-galactosidase producing strain is 100%, 50%, 10%, 1%,0%.

Once a pathogen is detected and mating occurs, a rapid visual response can be generated to inform the user of the test outcome. Many approaches have been considered and tested for the generation of a visual response, including direct production of various pigments and production of an enzyme that cleaves a substrate to produce a color change. Preliminary work has shown that β-galactosidase production leading to x-gal cleavage and a clear to blue color change can be detected even when β-galactosidase galactosidase producing cells are at 1% of saturation (FIG. 7).

Experiments are conducted to test if engineered yeast strains can identify the presence of mock pathogen cells. A sterile displayer strain is transformed with a SAP cassette. MATa and MATalpha displayer strains are constructed that both display a SAP complementary to that of the sterile displayer. These two strains are grown together along with different amounts of the sterile displayer strain. Negative controls containing the MATa and MATalpha displayer strains alone and grown with a non-complementary sterile strain are also included. Cytometry is performed to determine the mating efficiency for each condition. Mating may only occur when a sterile displayer strain expressing the complementary binder for the MATa and MATalpha displayer strains is added.

If it is found that the displayer cells can detect the presence of the appropriate mock pathogen, sterile displayer strains will be constructed that display two different SAPs. Here, MATa and MATalpha displayer strains are constructed that each display a SAP complementary to one of the SAPs expressed by the sterile displayer. A similar set of experiments is conducted in which mating is can occur only when a sterile displayer expressing the two complementary SAPs is added. For future diagnostic applications, this setup may allow for increased specificity for a pathogenic target by requiring two distinct binding domains.

Diagnostic sensitivity will also be assessed. The experiments described above include a mock antigen that is able to grow at the same rate as the displayer cells, which creates a simplified stoichiometry. However, this is unrealistic for a diagnostic application. In order to determine sensitivity, the sterile displayer strain must be prevented from growing for the duration of the mating assay. This can be accomplished with the knockout of Sstl, which makes the strain hypersensitive to mating factor. Other strains have previously been constructed with this knockout and they behave as expected. The result is that the strain is able to grow in isolation, but undergoes a strong and indefinite growth arrest in the presence of a-factor. To determine detection sensitivity, different concentrations of the hypersensitive sterile displayer is added to a culture of MATa and MATalpha displayer cells expressing complementary binders and mating efficiency is measured with flow cytometry.

While some pathogens are of a similar size to *S. cerevisiae,* viral and bacterial targets are much smaller. Most likely, avid binding is essential for sexual agglutination, so very small targets may not be able to provide enough binding interactions to anchor two yeast cells together. In order to determine the size requirements for detection, the mock pathogen strains is replaced with antigen coated mock pathogen beads of various sizes. Similarly, beads can be constructed with various antigen densities on their surface. Beads with a range of antigen densities are tested to determine the requirements for agglutination. If detection of mock pathogen is successful, detection of real pathogenic yeast, bacteria, and viruses will be attempted.

Multiplexed detection of multiple pathogens in a single assay will be tested. Two display pairs are combined in a single culture. A single sterile display strain expressing the targets for one of the pairs is added to show that presence of a single target results in the mating of only the appropriate display pair. Diploid isolation and colony PCRs is used to determine which display pair mated. The same protocol is repeated for the other complementary sterile display strain. Next, both sterile display strains are added to show that it is possible to detect multiple substrates in a single assay. This system will then be expanded to include more than two display pairs and the same process will be used for evaluation.

Figure 8:
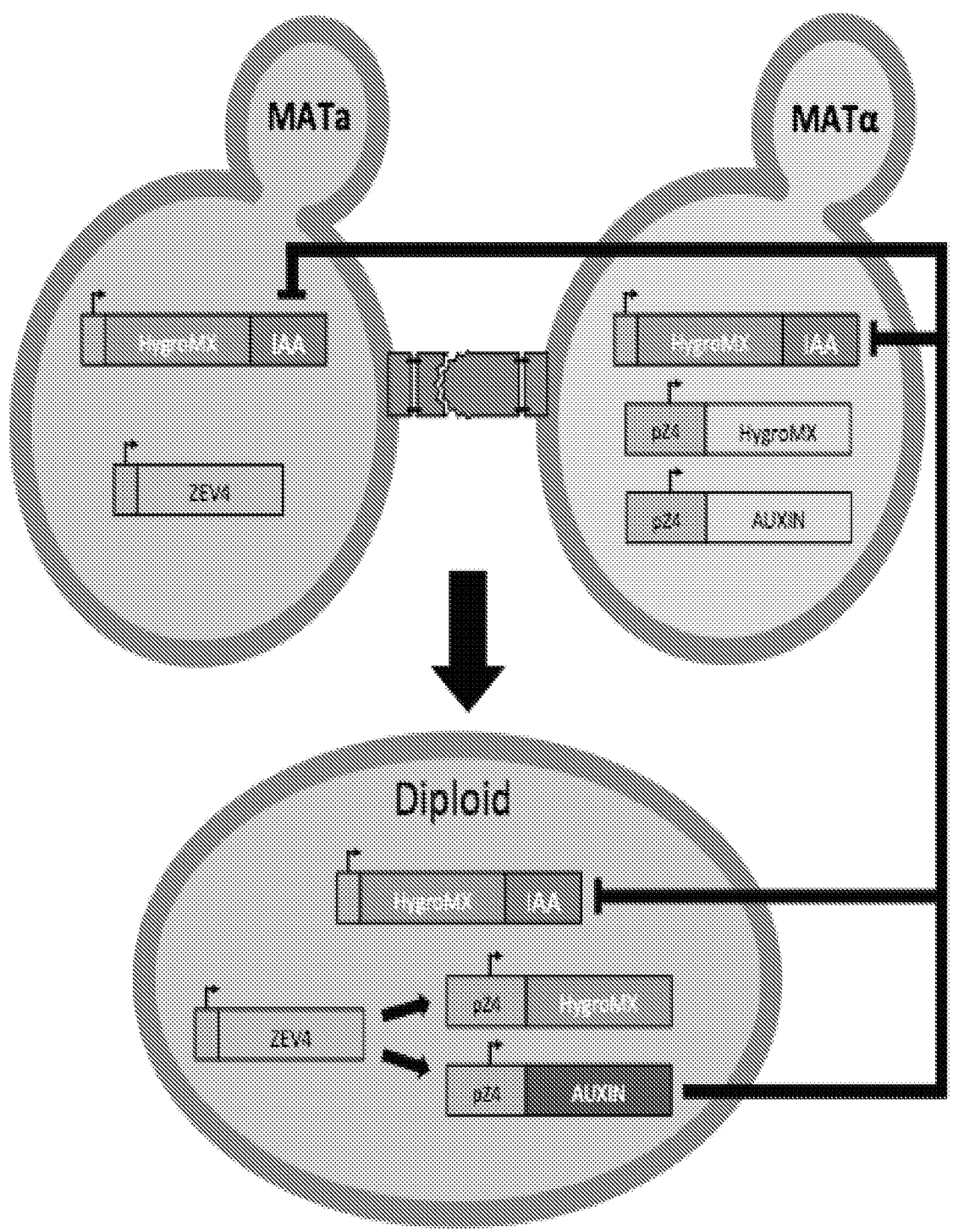
FIG. 8 shows a cartoon of cell-cell communication for autonomous diploid enrichment in a mating assay. Media is supplemented with hygromycin and IAH, a precursor to auxin. In addition to all of the other integrations required for the standard mating assay, MATa displayer cells are transformed with a constitutive hygromycin resistance gene fused to an auxin-dependent degron and a constitutive ZEV4 gene, which is an activator for the pZ4 promoter. MATalpha displayer cells are also transformed with a constitutive hygromycin resistance gene fused to an auxin-dependent degron and also contains a hygromycin resistance gene and an auxin synthesis gene under the expression of pZ4. Both of the genes under pZ4 expression are off in the MATalpha haploid. Upon mating and creating a diploid cell, ZEV4 activates both genes under control of the pZ4 promoter. The auxin synthesis gene converts IAH into auxin, which causes the degradation of all proteins fused to an auxin dependent promoter. Since auxin is membrane diffusible, this affects all cells and not just the ones expressing the auxin synthesis gene. The hygromycin resistance of all haploids is removed, resulting in their death and the enrichment of the diploid population.
Figure 9:
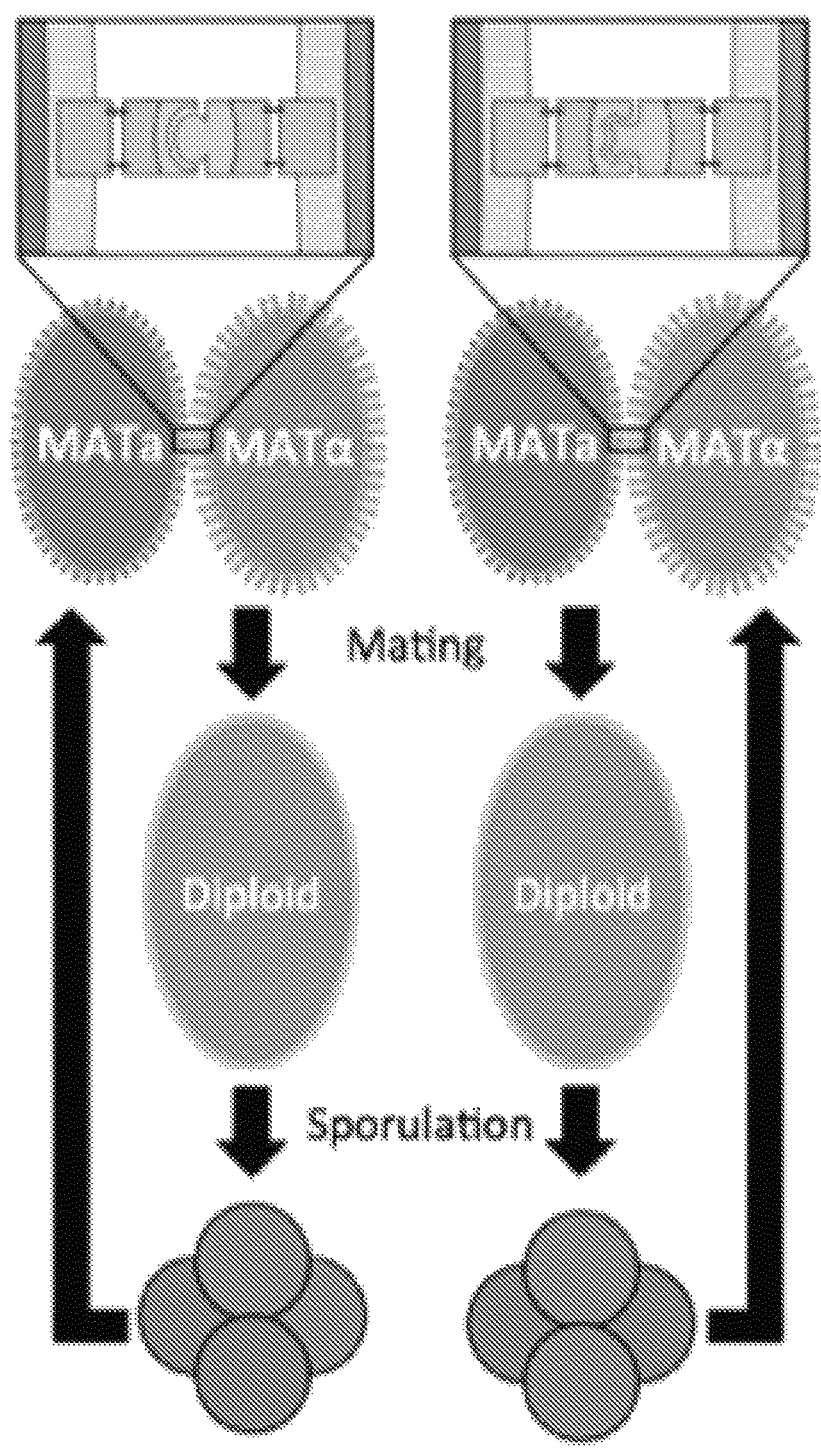
FIG. 9 shows a cartoon of agglutinin-based genetic isolation. Orthogonal SAP pairs will be chosen that cause a high mating efficiency within the pair, and very few off-target matings. All four strains will be mixed in a turbulent liquid culture. The result is agglutination between cells expressing complementary SAPs. Mating leads to the formation of diploid cells and the possibility of chromosomal crossover. Sporulation is then induced to recover the haploid display strains. This process is repeated until convergence on optimal growth rate for each carbon source is achieved.

As a next step to binary output generation, cell-cell communication will be used to increase the diploid population percent without a need for manually adding an antibiotic hours into the assay. A binary output has been generated by manually adding hygromycin 5 hours after the initial mating inoculation, which serves two purposes. First, it makes turbidity an output to mating efficiency. Second, if mating does occur, it results in a near 100% diploid population. If diploids are made to produce a pigment or enzyme as an output, a higher population fraction results in a more rapid and clearer visual response since there are more cells contributing to the color change. Of the two purposes served, the former is no longer important when considering a multiplexed assay, since it would not be possible to determine which pathogen were present based on turbidity alone. Achieving the latter may be possible with cell-cell communication (FIG. 8). Here, auxin is used to remove antibiotic resistance in haploid cells once diploids are formed, resulting in the enrichment of the diploid population.

Finally, it may be possible to use cells for the development of diagnostics in addition to the final diagnostic product. By developing a cell-based sensor that contains a selection and counter-selection scheme for the detection of an arbitrary substrate, libraries of candidate sensors can be screened and evolved for optimal sensitivity and specificity for a specific substrate. This would be particularly valuable for the detection of rapidly evolving viruses, such as influenza.

Example 2 demonstrates a novel cell-based diagnostic platform that allows for the detection of arbitrary extracellular targets by coupling binding to the mating efficiency of *S. cerevisiae.* This system is capable of detecting the presence of mock pathogen yeast strains with high specificity and can be expanded to the detection of clinically relevant pathogens.

Example 3. Synthetic Sexual Agglutination Can Cause Genetic Isolation in *S. cerevisiae*

Re-engineer *S. cerevisiae* sexual agglutination in order to better understand how pre-zygotic barriers can influence biological phenomenon such as speciation. In order to demonstrate that genetic isolation caused by mutations in the agglutinin proteins could lead to speciation, complementary pairs of MATa and MATalpha cells will undergo multiple rounds of mating and sporulation. Following each round of mating, a recombination assay is used to evaluate the extent of genetic isolation between haploids expressing complementary binders.

Sexual agglutinin proteins are mating type specific cell wall anchored proteins that facilitate direct cell-cell contact between haploid yeast cells of opposite mating types, which is the first step in mating for *S. cerevisiae.* Mutations in the sexual agglutinin proteins may create a pre-zygotic barrier that could lead to speciation. Existing models, however, have not allowed for this to be tested directly. Here, an engineering approach was used to generate a platform for synthetic sexual agglutination and this system can be used to demonstrate agglutinin-dependent genetic isolation. In particular, the role of the sexual agglutinin proteins was shown to be limited to cell adhesion and that arbitrary protein-protein interactions of sufficient strength can effectively replace the function of native agglutinin proteins. Using orthogonal pairs of synthetic agglutinin proteins, the diversity in these proteins alone can cause genetic isolation and divergent evolution in *S. cerevisiae.* This is demonstrated with the co-evolution of cells for optimized utilization of two different carbon sources in a single culture.

In a turbulent liquid culture, the mating of *S. cerevisiae,* as well as that of many other yeast species, is initiated by the expression of complementary sexual agglutinin proteins that are displayed on the surface of MATa and MATalpha haploid cells. The sexual agglutinin proteins are exclusively responsible for the aggregation of cells of opposite mating types and have no other known functions. The binding of Aga2 and Sag1 is the primary protein-protein interaction responsible for the aggregation of yeast cells of opposite mating types due to a high binding affinity, about $10^{-9}$ M, and high levels of expression on the yeasts' surface. The knockout of either of the primary sexual agglutinins is sufficient for the elimination of sexual adhesion. The result is an enormous drop in the efficiency of mating in a turbulent liquid culture, but no effect on mating efficiency on solid culture. Therefore, the sexual agglutinin proteins seem to be required only for agglutination.

Mutations in the sexual agglutinin proteins may have caused genetic isolation that has driven yeast speciation. This is an example of sexual selection driving isolation rather than environmental fitness. Compared to other genes, enormous variation in the sexual agglutinin proteins has been observed both among and between yeast species. *S. cerevisiae* utilize sexual reproduction to accelerate evolution by increasing population diversity. Without sexual reproduction, an initially isogenic cell line will slowly develop diversity through the accumulation of random mutations. The probability of many advantageous mutations accumulating in a given strain is low, resulting in a slow rate of evolution. However, if sexual reproduction is possible, chromosomal recombination drastically increases population diversity and makes the combination of advantageous mutations in a single strain far more likely. If cells that are initially isogenic are grown in isolation for long enough, they will lose their ability to sexually reproduce with one another, a phenomenon known as speciation. If an initially isogenic yeast strain developed mutations in their agglutinin proteins that allowed some population of cells to mate only with each other, then that population of cells may become genetically isolated from other cells in the culture. Mutations in the sexual agglutinin proteins may be able to create the genetic isolation required for speciation.

A synthetic biology approach can be used to test the requirements for sexual agglutination and the ability for sexual agglutinin proteins alone to generate genetic isolation that could lead to yeast speciation. Engineered MATa and MATalpha displayer strains lack their native primary sexual agglutinin proteins and instead display a synthetic adhesion protein (SAP) as a fusion to Aga2-myc. Haploid cells also constitutively express a fluorescent reporter unique to their mating type. After growing MATa and MATalpha cells together in liquid culture, the mating efficiency of a display pair expressing complementary or non-complementary SAPs can be determined with flow cytometry by comparing the percent of diploid cells, which express both markers, to total cells. In order to demonstrate genetic isolation, a co-enrichment assay is designed in which orthogonal display pairs will be enriched for optimal utilization of two different carbon sources in a single culture.

Materials and methods

PLASMID CONSTRUCTION: The plasmids used in Example 3 are listed in Table 6. For each plasmid, backbone and insert fragments were amplified with PCR, gel extracted, and assembled into plasmids using a Gibson reaction. Standard linkers between all parts increased the efficiency and consistency of cloning. All backbones, consisting of a high copy origin and ampicillin resistance, are flanked with Pme 1 restriction sites for easy linearization and integration into the yeast chromosome. All plasmids contain approximately 500 bases of chromosomal homology upstream and downstream of the target locus. Knockout (KO) plasmids contain upstream and downstream chromosomal homology, but no gene cassette. The promoter, open reading frame, terminator, and chromosomal homology of each plasmid were verified with Sanger sequencing.

TABLE 6

Plasmids used in Example 3.

| Name | Gene Cassette | Marker | Integration Locus |
|---|---|---|---|
| pYB1 | KO | [5-FOA] | URA3 |
| pYB2 | pGPD-Aga1-Tcyc1 | NatMX | HIS3 |
| pYB3 | pGPD-mCherry-Tcyc1 | BleoMX | YCR043 |
| pYB4 | pGPD-mTurquoise-Tcyc1 | BleoMX | YCR043 |
| pYB5 | KO | KanMX | AGA2 |
| pYB6 | KO | KanMX | SAG1 |
| pYB7 | pGPD-Aga2_Bfl1-Tcyc1 | Trp1 | ARS314 |
| pYB8 | pGPD-Aga2_BclB-Tcyc1 | Trp1 | ARS314 |
| pYB9 | pGPD-Aga2_Bcl2-Tcyc1 | Trp1 | ARS314 |
| pYB10 | pGPD-Aga2_BHRF1-Tcyc1 | Trp1 | ARS314 |
| pYB11 | pGPD-Aga2_Bim[BH3]-Tcyc1 | Trp1 | ARS314 |
| pYB12 | pGPD-Aga2_BINDI[F21]-Tcyc1 | Trp1 | ARS314 |
| pYB13 | pGPD-Aga2_BINDI[B+]-Tcyc1 | Trp1 | ARS314 |
| pYB14 | pGPD-Aga2_BINDI[2+]-Tcyc1 | Trp1 | ARS314 |
| pYB15 | pGPD-Aga2_BINDI[N62S]-Tcyc1 | Trp1 | ARS314 |

YEAST STRAIN CONSTRUCTION AND GROWTH CONDITIONS: The *S. cerevisiae* strains used in Example 3 are listed in Table 7. EBY100αwas created from EBY100a and W303αMOD by standard mating and sporulation procedures. Progeny were screened on selective plates and verified with diagnostic PCRs. All other strains were constructed with chromosomal integrations into EBY100a and EBY100α. Transformations were done by linearizing a given plasmid with a PmeI restriction digest and conducting a standard LiAc transformation procedure. Selection of transformants was accomplished using media deficient in a given auxotrophic marker or with media supplemented with a eukaryotic antibiotic. Diagnostic PCRs were conducted following each transformation to verify integration into the proper locus. All yeast assays use standard yeast culture media and growth at 30° C. All liquid culture growth is performed in 3 mL of YPD liquid media and shaking at 275 RPM.

TABLE 7

Yeast strains used in Example 3.

| Strain Name | Genotype | Transformants |
|---|---|---|
| EBY100a* | a GAL1-AGA1::URA3 ura3 trp1 leu2 his3 pep4::HIS2 prb 1Δ1.6R can1 GAL | |
| W303αMOD* | α ura3 trp1 lys2 his3 | |
| EBY100α** | α GAL1-AGA1::URA3 ura3 trp1 lys2 his3 pep4::HIS2 prb 1Δ1.6R can1 GAL | |
| EBY101a | a ura3 trp1 leu2 his3 pep4::HIS2 prb 1Δ1.6R can1 GAL | pYB1 |
| EBY101α | α ura3 trp1 lys2 his3 pep4::HIS2 prb1Δ1.6R can1 GAL | pYB1 |
| EBY103a | a GPD-AGA1::NatMX GPD-mCherry::BleoMX ura3 trp1 leu2 his3 pep4::HIS2 prb 1Δ1.6R can1 GAL | pYB1, pYB2, pYB3 |

TABLE 7-continued

Yeast strains used in Example 3.

| Strain Name | Genotype | Transformants |
|---|---|---|
| EBY103α | α GPD-AGA1::NatMX GPD-mTurquoise::BleoMX ura3 trp1 lys2 his3 pep4::HIS2 prb 1Δ1.6R can1 GAL | pYB1, pYB2, pYB4 |
| EBY104a (EBY103aΔaga2) | a aga2::KanMX GPD-AGA1::NatMX GPD-mCherry::BleoMX ura3 trp1 leu2 his3 pep4::HIS2 prb 1Δ1.6R can1 GAL | pYB1, pYB2, pYB3, pYB5 |
| EBY103aΔsag1 | a aga2::KanMX GPD-AGA1::NatMX GPD-mCherry::BleoMX ura3 trp1 leu2 his3 pep4::HIS2 prb 1Δ1.6R can1 GAL | pYB1, pYB2, pYB3, pYB6 |
| EBY103αΔaga1 | α sag1::KanMX GPD-AGA1::NatMX GPD-mTurquoise::BleoMX ura3 trp1 lys2 his3 pep4::HIS2 prb 1Δ1.6R can1 GAL | pYB1, pYB2, pYB4, pYB5 |
| EBY104α (EBY103αΔsag1) | α sag1::KanMX GPD-AGA1:NatMX GPD-mTurquoise::BleoMX ura3 trp1 lys2 his3 pep4::HIS2 prb 1Δ1.6R can1 GAL | pYB1, pYB2, pYB4, pYB6 |
| EBY104a_Bfl1 | a pGPD-AGA2_Bfl1::TRP1 aga2::KanMX GPD-AGA1::NatMX GPD-mCherry::BleoMX ura3 trp1 leu2 his3 pep4::HIS2 prb 1Δ1.6R can1 GAL | pYB1, pYB2, pYB3, pYB5, pYB7 |
| EBY104a_BclB | a pGPD-AGA2_BclB::TRP1 aga2::KanMX GPD-AGA1::NatMX GPD-mCherry::BleoMX ura3 trp1 leu2 his3 pep4::HIS2 prb 1Δ1.6R can1 GAL | pYB1, pYB2, pYB3, pYB5, pYB8 |
| EBY104a_Bcl2 | a pGPD-AGA2_Bcl2::TRP1 aga2::KanMX GPD-AGA1::NatMX GPD-mCherry::BleoMX ura3 trp1 leu2 his3 pep4::HIS2 prb 1Δ1.6R can1 GAL | pYB1, pYB2, pYB3, pYB5, pYB9 |
| EBY104a_BHRF1 | a pGPD-AGA2_BHRF1::TRP1 aga2::KanMX GPD-AGA1::NatMX GPD-mCherry::BleoMX ura3 trp1 leu2 his3 pep4::HIS2 prb 1Δ1.6R can1 GAL | pYB1, pYB2, pYB3, pYB5, pYB10 |
| EBY104α_Bim-BH3 | α pGPD-AGA2_Bim-BH3::TRP1 sag1::KanMX GPD-AGA1::NatMX GPD-mTurquoise::BleoMX ura3 trp1 lys2 his3 pep4::HIS2 prb 1Δ1.6R can1 GAL | pYB1, pYB2, pYB4, pYB6, pYB11 |
| EBY104α_BINDI-F21 | α pGPD-AGA2_BINDI-F21: :TRP1 sag1::KanMX GPD-AGA1::NatiMX GPD-mTurquoise::BleoMX ura3 trp1 lys2 his3 pep4::HIS2 prb 1Δ1.6R can1 GAL | pYB1, pYB2, pYB4, pYB6, pYB12 |
| EBY104α_BINDI-B+ | α pGPD-AGA2_BINDI-B+::TRP1 sag1::KanMX GPD-AGA1::NatMX GPD-mTurquoise::BleoMX ura3 trp1 lys2 his3 pep4::HIS2 prb 1Δ1.6R can1 GAL | pYB1, pYB2, pYB4, pYB6, pYB13 |
| EBY104α_BINDI-2+ | α pGPD-AGA2_BINDI-2 +::TRP1 sag1::KanMX GPD-AGA1: :NatMX GPD-mTurquoise::BleoMX ura3 trp1 lys2 his3 pep4::HIS2 prb 1Δ1.6R can1 GAL | pYB1, pYB2, pYB4, pYB6, pYB14 |
| EBY104α_BINDI-N62S | α pGPD-AGA2_BINDI-N62S::TRP1 sag1::KanMX GPD-AGA1::NatMX GPD-mTurquoise::BleoMX ura3 trp1 lys2 his3 pep4::HIS2 prb 1Δ1.6R can1 GAL | pYB1, pYB2, pYB4, pYB6, pYB15 |

*Strains that were obtained from the Dunham Lab. **Strain constructed from EBY100a and W303αMOD by mating, sporulation, and screening on selective plates. All other strains were constructed for this study using the plasmids listed.

CHARACTERIZATION OF YEAST SURFACE DISPLAY STRAINS: Surface expression strength is measured by incubating 10 μL of each individually grown cell strain for 15 minutes with FITC conjugated anti-myc antibody in PBSF following a wash in 1 mL of water. Cells are then washed again and resuspended in 1 mL of water. Flow cytometry is then performed. For this experiment, an ACCURI™ C6 cytometer is used. The FL1A channel (488 nm excitation laser and 533 nm emission filter) is used to measure FITC binding to the cell. FLOWJO® is used for all cytometry analysis. EBY104a and EBY104α show a low fluorescence, while all EBY104 strains with an integrated surface display construct show a high fluorescence. This indicates that all strains are properly displaying proteins on their surface.

MATING ASSAYS: To evaluate the mating efficiency between any two yeast strains in liquid culture, haploid strains are initially grown to saturation, or for approximately 18 hours, from an isogenic colony on a fresh YPD plate. Each haploid is then combined in a fresh 3 mL YPD liquid culture such that the MATa strain is at a density of 100 cells/μL and the MATalpha strain is at a density of 600 cells/μL. This difference in starting concentration is an adjustment for the uneven growth response to mating factor. Following 15 hours of growth, 2.5 μL of mating culture is added to 1 mL of molecular grade water and read on a flow cytometer. MATa, MATalpha, and diploid cells are distinguished based on fluorescent intensity of mCherry and mTurquoise. For the experiments described here, a Miltenyi MACSQUANT® VYB was used. The Y2 channel (561 nm excitation laser and 615 nm emission filter) is used to measure mCherry expression and the V1 channel (405 nm excitation laser and 450 nm emission filter) is used to measure mTurquoise expression. The diploid cell population as a percent of total cell population after 15 hours is used as a measure of mating efficiency. Since there is some noise in the cytometry assay, an additional step is used to ensure that the mating efficiency is zero between non-complementary SAP pairs. Here, a secondary growth phase in SC-lys-leu was conducted to determine if any mating took place between two display strains. All MATa strains used in this study lack the leu2 gene, and all MATalpha strains lack the lys2 gene. Therefore, haploids are unable to grow in media lacking these two amino acids. Diploids, which containing both genes, are able to grow. After the 17 hour mating, 10 μl were removed and added to 3 mL SC-lys-leu media. After 48 hours, the culture was observed for growth.

For a batched mating assay, more than two haploid strains are combined in the fresh YPD culture. Following 15 hours of growth, the culture is struck onto a SC-Lys-Leu plate to obtain isolated colonies. Following 48 hours of growth, approximately 2 μL of cells are removed from multiple isogenic colonies, lysed with 0.2% SDS, spun down to remove all cellular debris, and diluted in water. The lysate is then used as a template for a PCR with standard primers that amplify a barcode associated with each SAP. Sanger sequencing is performed on each fragment for genotype determination.

Results

The function of the sexual agglutinin proteins can be replaced with the expression of complementary SAPs with a sufficiently high affinity. Wild-type S. cerevisiae haploids require Aga2 and Sag1 expression for agglutination and mating in liquid culture (see FIG. 3B,C). However, these native proteins can be replaced with engineered protein-protein interactions (see FIG. 3D). The mating efficiency between two displayer cells is dependent on the affinity of their respective SAPs. A SAP pair with A $K_D$ greater than 10,000 nM has a near zero mating efficiency in a turbulent liquid culture (see FIG. 3E).

Figure 10:
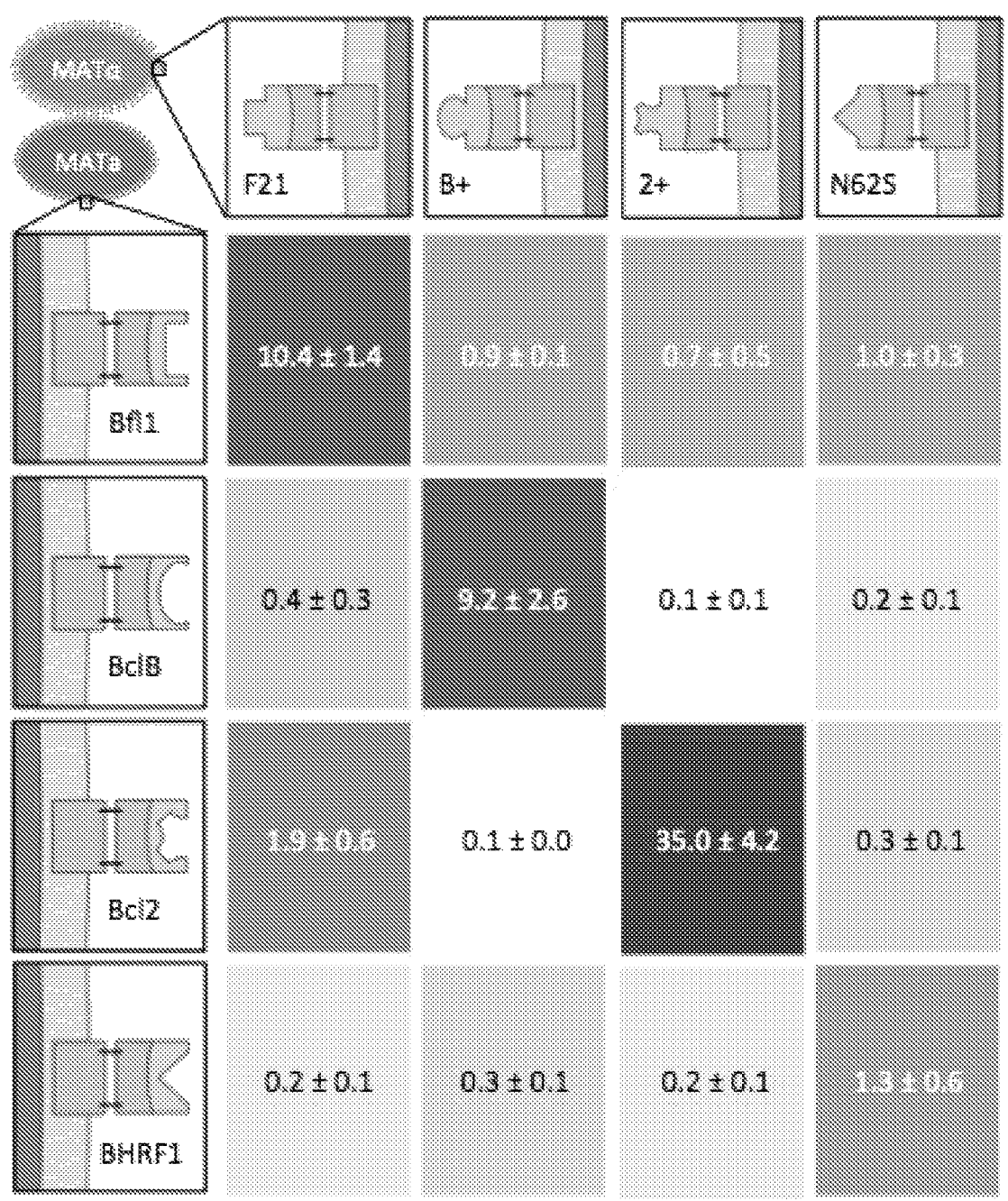
FIG. 10 shows a mating orthogonality matrix. Mating tests for all pairwise combinations between four MATa display strains and four MATalpha display strains was performed. Each mating was performed four times. The average mating efficiency, in diploid percent, as well as the standard deviation of the mating efficiency for each display pair are shown. The two pairs most orthogonal to one another are chosen for later experiments to demonstrate genetic isolation. These two pairs are Bcl/B+ and Bcl2/2+.

Orthogonal SAP pairs are chosen such that the mating efficiency within each pair is high but the mating efficiency between haploids of different pairs is near zero. This is true when complementary SAP pairs have a $K_D$ that is lower than 50 nM and all non-complementary pairs have a $K_D$ greater than 10,000 nM. When two or more display pairs with orthogonal SAPs are grown together, mating occurs exclusively between haploids with complementary SAPs. Many of the non-complementary non-zero mating efficiencies shown in FIG. 10 are inflated by random scatter, possibly debris or dead cells, that falls into the diploid gate erroneously. As a result, it is likely that all of the mating efficiencies are inflated by somewhere between 0% and 1%. With a secondary growth phase in SC-lys-leu, it was confirmed that most non-complementary mating efficiencies are actually zero.

This system is dependent on the ability to segregate genes with mating type during sporulation. It is essential that a given SAP and fluorescent marker is always associated with the same mating type. In order to accomplish this, all SAP cassettes are integrated into the ARS314 locus and fluorescent marker cassettes are integrated into the YCR043 locus. These loci flank the MAT gene on chromosome III. Therefore both of these genes should be sex linked. This, however, is evaluated before a long-term evolution experiment is started. A display pair undergoes 10 rounds of mating and sporulation. After each round, isogenic haploids are isolated by streaking on a plate. The fluorescent marker and mating type of many haploids are evaluated. The marker is determined with flow cytometry and the mating type is identified using a halo assay with MATa and MATalpha haploid strains hypersensitive to mating factor. Even after multiple rounds of mating and sporulation, all mCherry expressing cells will be MATa and all mTurquoise expressing cells will be MATα.

Orthogonal pairs of complementary SAPs are identified from a set of proteins that were engineered to bind to one of four homologues of BHRF1 with high specificity. Two display pairs, B and C, expressing complementary but orthogonal SAPs are chosen. The MATa strain from display pair B is transformed with a promoter library that provides variable fitness for growth on galactose and the MATa strain from display pair C is transformed with a promoter library that provides variable fitness for growth on xylose. Rounds of mating and sporulation are used to enrich for optimal fitness in a liquid culture consisting of only galactose and xylose as carbon sources. After each round of mating and sporulation, the MATalpha haploid from each pair is analyzed for fitness on each carbon source individually. MATalpha haploid from display pair B should have a high fitness for growth on galactose while that MATalpha haploid from display pair C should have a high fitness for growth on xylose. This experiment is intended to demonstrate genetic isolation between the two orthogonal display pairs that can lead to divergent evolution, in this case optimal fitness for growth on two different carbon sources.

The S. cerevisiae sexual agglutinin proteins are necessary only for adhesion between cells of opposite mating type and can be replaced with engineered synthetic adhesion proteins such that mating only occurs between MATa and MATalpha cells expressing complementary SAPs. Here, it has been shown that orthogonal SAPs can be expressed on two pairs of yeast haploid strains and that this modification alone causes genetic isolation between the two pairs when matings are done in a turbulent liquid culture. A co-evolution assay can be performed in which two orthogonal displayer strain pairs are enriched for optimal growth on different carbon sources in one pot.

Example 4. An Engineerable Pre-Zygotic Barrier as a Model for Reproductive Ecology Re-engineer S. cerevisiae sexual agglutination in order to better understand how pre-zygotic barriers can influence ecological dynamics. In order to demonstrate that genetic isolation caused by mutations in the agglutinin proteins could alter ecological dynamics, complementary pairs of MATa and MATalpha cells undergo multiple rounds of mating and sporulation. Haploids expressing synthetic agglutinin proteins are used to model complex interspecies pre-zygotic barriers that would be impossible to quantify in higher-order organisms. The system is complemented with a predictive computational model.

Genetic variability within a species results in each individual having distinct but immeasurable likelihoods to sexually reproduce with each individual of the opposite mating type. Some variations may result in a decreased likelihood to mate with all other individuals and others may cause the formation of subsets of preferential mating. In a complex multicellular species, there are an infinite number of genetic variations that each confers an unknown effect on mating preference, making it enormously challenging to study the reproductive ecology of these species directly. Here, a model system was created for the study of intraspecies reproductive ecology in which the relative mating frequencies between any individual and all individuals of the opposite mating type can be precisely dictated. In particular, it was demonstrated that engineered sexual agglutinin proteins displayed on the surface of S. cerevisiae can be used to generate arbitrary and measurable mating efficiencies between any given strains. Then a computational model was used to predict population dynamics given an initial set of strains with fully characterized mating efficiencies and validate the model experimentally.

Synthetic ecology has been proposed as a method for understanding natural ecological systems by constructing them. It is often impossible to uncouple, score, or even identify many essential variables for studying natural ecological systems. A synthetic system, however, can be manipulated in a controlled way in order to better understand the characteristics of enormously complex ecological relationships. Until now, this synthetic ecology approach has been used to study the relationships between multiple species, such as interspecies cooperativity and predator-prey dynamics. This example presents a novel S. cerevisiae platform for the study of intraspecies reproductive ecology.

Sexual reproduction provides a unique form of selective pressure that is not directly coupled to individual fitness. Although number of offspring is often dependent on natural selection, sexual selection also plays a critical role. Many higher order species consider factors such as size, strength, and other physical attributes when choosing a mate. Given perfect knowledge of a species and all of its members, it would be possible to consider the importance of every characteristic in choosing a mate and compute a mating likelihood with every individual of the opposite mating type. Lacking the perfect knowledge of a species, this is an impossible endeavor, which makes it very difficult to study complex intraspecies ecological systems, such as a ring species. A ring species is a single species in which individuals predominantly mate with only a subset of the members of the opposite mating type. However, rather than the formation of distinct subspecies that mate only amongst themselves, a ring-like mating pattern is formed. This type of reproductive ecology has garnered substantial interest. This example presents the first synthetic ecology model for studying the dynamics and stability of complex intraspecies ecological phenomenon that are driven by mating preference.

The model consists of MATa and MATalpha *S. cerevisiae* displayer cells that express synthetic adhesion proteins (SAPs) on their surface rather than their respective sexual agglutinin proteins. Each individual haploid cells expresses many copies of a single barcoded SAP. The result is a correlation between mating likelihood of a particular display pair, consisting of one MATa and MATalpha, and the binding affinity of the SAPs displayed on their surfaces. The mating likelihood for any display pair is determined by growing the two strains together in liquid culture and observing the number of matings that take place relative to the haploid cell population. Given the infinite number of potential protein-protein affinities, it is also possible to select display pairs that exhibit a particular desired mating likelihood. Once all mating likelihoods are determined for a set of MATa and MATalpha cells, a batched mating is conducted, in which all cells are grown together and diploid cells are isolated. Next generation sequencing is used to determine the SAP pair that resulted in the formation of each diploid. Sporulation recovers the haploid displayer cells that were able to mate. Multiple rounds of sporulation and re-mating are conducted, and the SAP distribution is measured each round with next generation sequencing.

Materials and Methods

A computational model has been constructed to predict potential dynamic behaviors of the *S. cerevisiae* reproductive ecology model. As an initial condition, 10 MATa displayer strains and 10 MATalpha displayer strains are added as an equal percent of the total population, represented by a haploid population percent vector. Each display pair is randomly assigned a mating likelihood, between zero and one, which is contained in a mating likelihood matrix. A mating is simulated for each display pair by multiplying the population percent of both haploids in the pair and multiplying this product by the pair's mating likelihood in a mating simulation matrix. A sporulation is then simulated and the population percent of each of the 20 haploids is calculated. Each MATa population percent is calculated by summing a column in the mating simulation matrix and dividing this value by the total sum of the mating simulation matrix. Similarly, the population percent of each MATalpha is calculated by summing a row in the mating simulation matrix and dividing this value by the total sum of the mating simulation matrix. These values provide an updated haploid population percent vector, which is then used to generate the next mating simulation matrix. A total of 500 rounds of mating and sporulation are repeated, and the population percent of each haploid is plotted after each round.

Figure 12A:
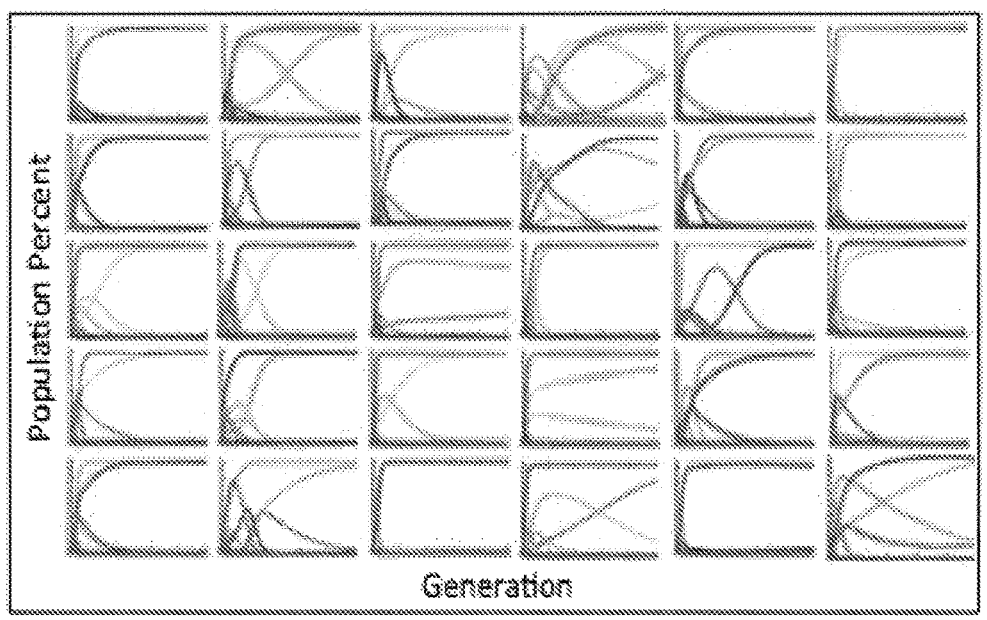
FIG. 12A-FIG. 12C show the results of simulations from a computational model of reproductive ecology. Numerous random mating likelihood matrices were generated with 10 members of each mating type.
Figure 12B:
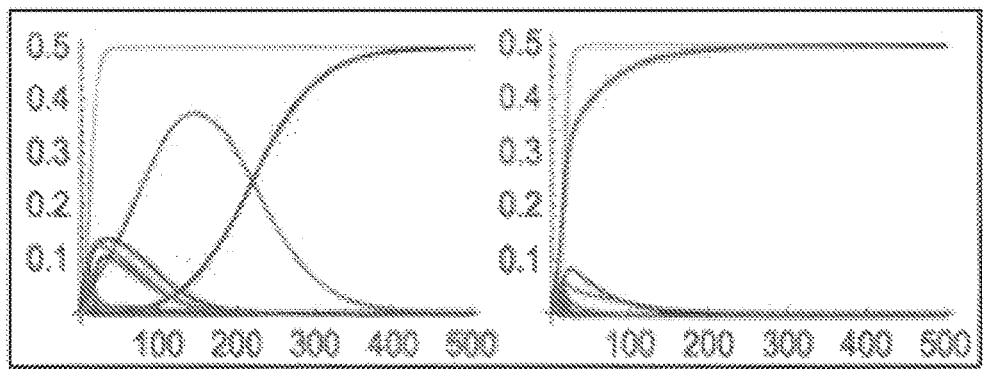
Figure 12C:
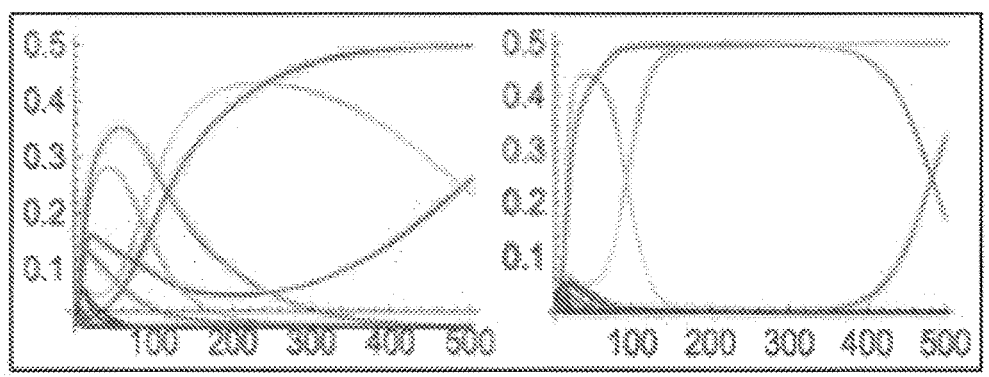

Based on the computational simulations, many interesting reproductive ecological dynamics can be observed by randomly choosing 10 individuals from each mating type with random mating likelihoods (FIG. 12A). Most of the simulations result in a single display pair, the pair with the highest mating likelihood, taking over the population (FIG. 12B). However, based on the interconnectedness of mating likelihoods and competition for mates, more interesting behavior can be observed in some simulations (FIG. 12C).

COMPUTATIONAL MODELING: Following the simulations from many randomly constructed mating likelihood matrices, analysis of the matrices that resulted in specific interesting behaviors should provide insight into what the requirements are for those types of behaviors. Some properties of the mating likelihood matrix may have obvious ecological results. For example, if the mating likelihood for a single pair is far higher than that of any other, it is likely that the two haploids of this pair will rapidly take over the population. It is less obvious, however, what happens when many pairs have similar mating likelihoods or what the specific requirements are for oscillatory behavior.

Once the relationships between the mating likelihood matrix and population dynamics are better understood, it may be possible to rationally construct matrices that generate interesting behaviors. The construction of a ring species and of a species that undergoes oscillatory reproductive ecological dynamics are of particular interest. Using this model, it may be possible to comment on the stability of these systems.

Long-term experiments consisting of many rounds of matings and sporulations are carried out to observe reproductive ecological phenomenon over many generations. MATa and MATalpha libraries with barcoded SAP integrations in chromosome III are selected randomly or by rationally choosing each strain to best match a particular mating likelihood matrix. Before the batched mating begins, each display pair is grown together in isolation and given a mating likelihood score based on their observed mating efficiency. Each MATa constitutively expresses mCherry and each MATalpha constitutively expresses mTurquoise. After being grown together for 15 hours, cytometry is performed to determine the percent of the population that is made up of diploid cells, which will express both fluorescent reporters.

Each batched mating begins with all strains at a concentration of 25 cells/µL in 3.1 mL YPAD. The mating proceeds for 17 hours. At this time, 100 µL is transferred to YPAD media containing hygromycin, which kills any remaining haploid cells, and β-estradiol ((βE), which induces expression of CRE recombinase. The recombinase causes a chromosomal translocation that juxtaposes the barcodes from each SAP onto the same chromosome such that cell lysis does not uncouple the SAP pair responsible for the formation of that particular diploid. A colony PCR amplifies this region of the chromosome and next generation sequencing is used to determine the relative frequencies of each SAP pair within the diploid population. The remaining 3 mL is washed and transferred to sporulation media. Following sporulation, β-glucuronidase is added to digest the ascus and break apart the spores. Another wash is performed, followed by the transfer of the spores back into YPAD media to begin the second round of mating. This process is repeated many times.

Example 4 describes an *S. cerevisiae* model and a matching computational model for the study of sexual reproductive ecology. This simplified system can be used to study the effect of mating preference within a population on the ecological dynamics of the species in a way that cannot be done for complex natural systems. This model can make it possible to analyze the stability of complex intraspecies mating relationships, including ring species.

Example 5. Modular Plasmid Cloning Scheme

Figure 13:
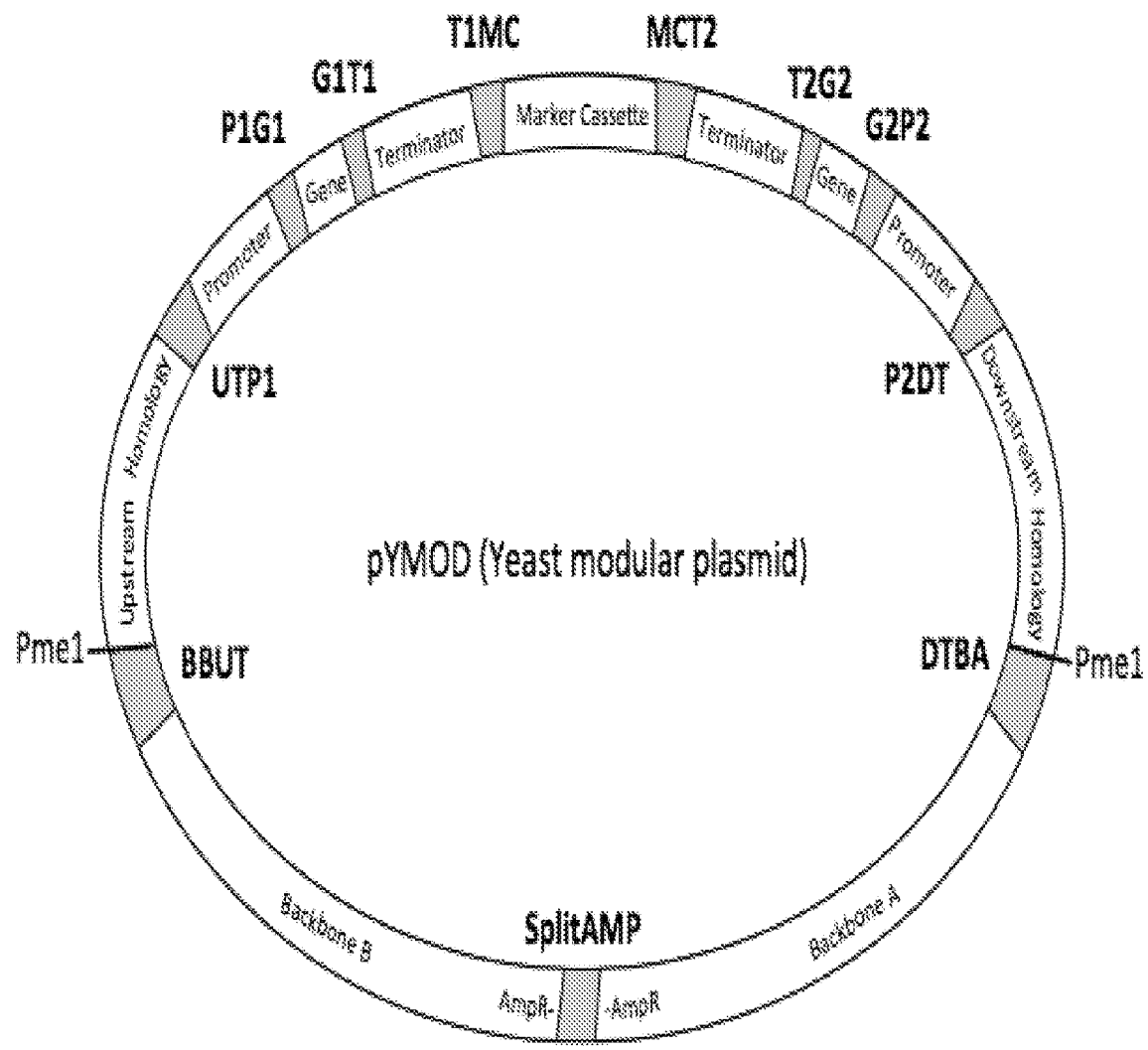
FIG. 13 shows the pYMOD yeast modular plasmid layout. The plasmid contains two sites for gene cassettes in a convergent orientation with a marker cassette in the middle. Standard linkers that are optimized for Gibson assembly flank each part. PME1 restriction sites are included to linearize the plasmid for integration. If only a single cassette is desired, the downstream homology part can be amplified with the MCT2 linker. For genomic knockouts, the upstream homology part can be amplified with the T1MC linker and the downstream homology part can be amplified with the MCT2 linker.

Many of the yeast strains described in this disclosure required multiple transformations. Displayer strains compatible with the CRE recombinase assay, for example, required the integration of Aga1 under the control of a constitutive promoter, the knockout of a sexual agglutinin protein, the integration of a fluorescent reporter, the integration of CRE recombinase and GAVN or of HygMX and ZEV4, and the integration of a barcoded surface expression cassette with a lox site. For each integration, a plasmid must be constructed that contains the required yeast cassette, an *E. coli* resistance marker and origin of replication, and 5' and 3' regions of homology to the yeast genome for integration. As many plasmids are required, a modular yeast plasmid was designed to simplify the cloning workflow and allow for the reuse of fragments for multiple plasmids. Even so, the large number of transformations would require more selectable markers than available if each were done individually. So, the modular plasmid scheme was designed to contain one or two gene cassettes, so that two integrations could be done at a single time with a single selectable marker. The basic scheme is shown in FIG. 13.

The linker sequences, except for SplitAMP, were designed with the R2oDNA designer. Each linker is 25 base pairs, has a $T_m$ of 72° C., has no more than 10 base pairs of homology to the genome of *S. cerevisiae*, has a minimum intra-molecular folding energy of −4 kcal/mol, and has a minimum inter-molecular folding energy of −9 kcal/mol. These specifications make the linkers ideal for Gibson assembly. The linker sequences are listed in Table 8 below.

TABLE 8

| Linker Name | Sequence |
|---|---|
| The linkers used for the pYMOD yeast modular plasmid cloning scheme. | |
| BBUT | GTCGGCGGGACCAGGGAGTTTAAAC (SEQ ID NO:01) |
| UTP1 | GCCGATACGAAGGTTTTCTCCAGCG (SEQ ID NO:02) |
| P1G1 | GGGACCGTCAACCCTGAACCACAAA (SEQ ID NO:03) |
| G1T1 | TGAGCAGGCATCGAGTGAAGTCAAC (SEQ ID NO:04) |
| T1MC | GCTTCAATAAAGGAGCGAGCACCCG (SEQ ID NO:05) |
| MCT2 | CAGAAGCGAGGCGAATAAAGGTGGC (SEQ ID NO:06) |
| 12G2 | CGATACCTGGTTGTGGGCTCTCTCA (SEQ ID NO:07) |
| G2P2 | TTTGTCTGACAACCGTTCGCAGAGC (SEQ ID NO:08) |
| P2DT | GTCCCTGAAAACCACTGAGTTGCCC (SEQ ID NO:09) |
| DTBA | CATGGTCATAGCTGTTTCCTGTGT (SEQ ID NO:10) |

TABLE 8-continued

| Linker Name | Sequence |
|---|---|
| The linkers used for the pYMOD yeast modular plasmid cloning scheme. | |
| SplitAMP_F | GTTCGCCAGTTAATAGTTTGCGCAACG (SEQ ID NO:11) |
| SplitAMP_R | CTCGAGGGGGGCGGATCC (SEQ ID NO:12) |

This modular plasmid scheme has been used to successfully construct the majority of plasmids used in this disclosure. The linkers perform well in Gibson assemblies. If no parts are pre-assembled, a minimum of an 11 piece Gibson would be required. If either of the genes requires assembly from multiple parts, for example if a protein fusion is being constructed that contains an additional modular linker for assembly, this number can be even higher. Assemblies with this number of parts are inefficient and typically do not produce enough correctly assembled plasmid for transformation into *E. coli*. However, enough assembled plasmid is generated for amplification with PCR, which can be used to combine multiple parts and repeat a Gibson assembly with fewer parts. This has been the general strategy used for plasmid construction (see FIG. 21).

Much of the cloning work used to construct yeast strains for this disclosure was done through "Aquarium," a lab automation system developed in the Klavins lab. In this system, all cloning protocols from ordering primers to transforming yeast are coded in Krill, a formalized programming language for laboratory protocols. This code is interpreted by the Aquarium software, which displays step-by-step instructions on touch screen monitors to lab technicians. The software generates and automated laboratory notebook that contains all information about what was done in the lab in order to produce a new sample and tracks the inventory of every item in the lab. All experimental work, including mating assays, flow cytometry, and CRE recombinase assays, was done independently.

Example 6. Reprogramming Yeast Mating to Characterize Protein-Protein Interactions in High-Throughput Besides on-target binding, protein-protein interactions (PPI) often have more sophisticated application dependent requirements such as binding at a specific site, orthogonality with other engineered or natural PPIs, high affinity binding to multiple targets, or dynamic interactions that respond to environmental changes. Despite improvements with in silico modeling, experimental screening is necessary for identifying and optimizing designs that meet specified criteria and is a major bottleneck for protein-protein interactions engineering. Here, a quantitative library-on-library characterization of PPIs was achieved in a controllable environment by reprogramming yeast sexual agglutination to link protein interaction strength with mating efficiency. Validation with a previously characterized 96 PPI network shows a strong monomial relationship between mating efficiency and PPI strength for interactions with a $K_D$ between 100 μM and 100 pM. Further, observed PPI strengths change when the binding environment is manipulated. Finally, a 1,400 member design library was screened with a panel of on- and off-target proteins for the identification of variants with desired target affinity and specificity.

Existing approaches for experimentally screening computationally designed PPIs fail to meet the needs of many modern protein engineering challenges. For example, despite their scientific and medical relevance, no methods exist for the high throughput screening of protein interaction network design, two-sided design, or non-membrane permeable ligand mediated interaction design. Surface display techniques, such as yeast surface display, are commonly used for screening a one-sided design library but can only characterize binding against a limited number of targets per assay due to the small number of spectrally resolvable fluorescent markers. Intracellular binding assays, such as yeast two-hybrid, cannot be used to characterize dynamic interactions with non-membrane permeable or toxic ligands and suffer from the influence of host cell conditions. Recently, cell-free approaches for protein network characterization have demonstrated increased throughput by replacing fluorescent markers with DNA barcodes, but these approaches lose the advantages of genetic encoding such as rapid library construction and ease of iteration. The lack of an appropriate high throughput screening platform has caused an experimental bottleneck in which protein engineers are unable to test many potentially functional designs due to time and resource constraints.

Removal of this bottleneck requires a high throughput screening approach to quantify binding strength between two libraries in a controllable environment. An extracellular yeast-based assay was built for the one-pot characterization of protein interaction networks. To accomplish this, yeast sexual agglutination was re-engineered, which is a natural protein-protein interaction in *S. cerevisiae* in which binding is essential for mating in liquid culture. In response to the detection of mating factor from a cell of the opposite mating type, haploid cells begin to express mating type specific sexual agglutinin proteins on their surface. The primary agglutination interaction is between the MATa sexual agglutinin subunit, Aga2, and the MATalpha sexual agglutinin, Sag 1. The binding affinity for the Aga2-Sag 1 interaction is approximately 2nM. This affinity combined with high avidity due to multiple interactions occurring between two cells results in the irreversible binding of a MATa and MATalpha cell. Substantial diversity of sexual agglutinin proteins exists across yeast species, indicating a large design space and high capacity for engineering.

Materials and Methods

DNA CONSTRUCTION: Isogenic fragments for yeast transformation or plasmid assembly were PCR amplified from existing plasmids or yeast genomic DNA, gel extracted from a plasmid digest, or synthesized by Integrated DNA Technologies. Plasmids were constructed with isothermal assembly and verified with Sanger sequencing, which was also used to identify the ten base barcode corresponding to each SAP. A list of plasmids used in Example 6 is shown in Table 9 below.

TABLE 9

List of plasmids used in Example 6.

| Plasmid Name | Gene Cassette(s) | Marker | Integration Locus |
| --- | --- | --- | --- |
| pMOD_NatMX_HIS_pGPD-Aga1 | pGPD-Aga1 | NatMX | HIS |
| pMOD_BleoMX_LTR2_pGPD-mChe | pGPD-mCherry | BleoMX | LTR2 |
| pMOD_BleoMX_LTR2_pGPD-mTur | pGPD-mTurquoise | BleoMX | LTR2 |
| pYMOD_URA_SAG1_KO | Knockout | URA | SAG1 |
| pYMOD_KanMX_YCR043_pZ4-CRE | pZ4-CRE | KanMX | YCR043 |
| pYMOD_KanMX_YCR043_pACT1-ZEV4 | pACT1-ZEV4 | KanMX | YCR043 |
| pYMOD_BleOMX_ARS314_pGAL-Sce1 | pGAL-Sce11 | BleoMX | ARS314 |
| pNGYSDa_Bfl1 | pGPD-mCherry & pGPD-Aga2-Bfl1 | TRP | ARS314 |
| pNGYSDa_BclB | pGPD-mCherry & pGPD-Aga2-BclB | TRP | ARS314 |
| pNGYSDa_Bcl2 | pGPD-mCherry & pGPD-Aga2-Bcl2 | TRP | ARS314 |
| pNGYSDa_BclW | pGPD-mCherry & pGPD-Aga2-BclW | TRP | ARS314 |
| pNGYSDa_BclXL | pGPD-mCherry & pGPD-Aga2-BclXL | TRP | ARS314 |
| pNGYSDa_Mcl1[151-321] | pGPD-mCherry & pGPD-Aga2-Mcl1[151-321] | TRP | ARS314 |
| pNGYSDα_Bim.BH3 | pGPD-mTurquoise & pGPD-Aga2-Bim.BH3 | TRP | ARS314 |
| pNGYSDα_Noxa.BH3 | pGPD-mTurquoise & pGPD-Aga2-Noxa.BH3 | TRP | ARS314 |
| pNGYSDα_Puma.BH3 | pGPD-mTurquoise & pGPD-Aga2-Puma.BH3 | TRP | ARS314 |
| pNGYSDα_Bad.BH3 | pGPD-mTurquoise & pGPD-Aga2-Bad.BH3 | TRP | ARS314 |
| pNGYSDα_Bik.BH3 | pGPD-mTurquoise & pGPD-Aga2-Bik.BH3 | TRP | ARS314 |
| pNGYSDα_Hrk.BH3 | pGPD-mTurquoise & pGPD-Aga2-Hrk.BH3 | TRP | ARS314 |
| pNGYSDα_Bmf.BH3 | pGPD-mTurquoise & pGPD-Aga2-Bmf.BH3 | TRP | ARS314 |
| pNGYSDα_FINDI-F21 | pGPD-mTurquoise & pGPD-Aga2-FINDI-F21 | TRP | ARS314 |

TABLE 9-continued

List of plasmids used in Example 6.

| Plasmid Name | Gene Cassette(s) | Marker | Integration Locus |
| --- | --- | --- | --- |
| pNGYSDα_FINDI-F30D | pGPD-mTurquoise & pGPD-Aga2-FINDI-F30D | TRP | ARS314 |
| pNGYSDα_BINDI-B+ | pGPD-mTurquoise & pGPD-Aga2-BINDI-B+ | TRP | ARS314 |
| pNGYSDα_BINDI-BCDP01 | pGPD-mTurquoise & pGPD-Aga2-BINDI-BCDP01 | TRP | ARS314 |
| pNGYSDα_BINDI-B40A | pGPD-mTurquoise & pGPD-Aga2-BINDI-B40A | TRP | ARS314 |
| pNGYSDα_2INDI-2+ | pGPD-mTurquoise & pGPD-Aga2-2INNDI-2+ | TRP | ARS314 |
| pNGYSDα_2INDI-4LVT | pGPD-mTurquoise & pGPD-Aga2-2INDI-4LVT | TRP | ARS314 |
| pNGYSDα_WINDI-aBCLW | pGPD-mTurquoise & pGPD-Aga2-WINDI-aBCLW | TRP | ARS314 |
| pNGYSDα_XINDI-XCDP07 | pGPD-mTurquoise & pGPD-Aga2-XINDI-XCDP07 | TRP | ARS314 |
| pNGYSDα_MINDI | pGPD-mTurquoise & pGPD-Aga2-MINDI | TRP | ARS314 |

YEAST STRAIN CONSTRUCTION: A MATa haploid strain optimized for surface display, EBY100, was used as a parent strain. A parent MATalpha haploid surface display strain was constructed with mating, sporulation, tetrad dissection, and screening with selectable markers. Isogenic chromosomal integrations consisted of digesting a plasmid with Pme 1 and then following a standard lithium acetate protocol. SSM libraries were transformed into yeast using nuclease assisted chromosomal integration. Parent strains containing a Sce1 landing pad were grown for 6 hours in galactose media prior to transformation. Recycling of the URA3 gene was accomplished by growing a strain to saturation without URA selection and plating on 5-FOA. A list of yeast strains used in Example 6 is shown in Table 10.

TABLE 10

List of yeast strains used in Example 6.

| Strain Name | Description | Parent | Transformant |
| --- | --- | --- | --- |
| EBY100a | Yeast surface display strain | | |
| W303αMOD | MATα for generation of EBY100α | | |
| EBY100α | MATα version of yeast surface display strain | Mating of EBY100a and W303αMOD | |
| EBY101a | URA knockout with 5-FOA selection | EBY100a | |
| EBY101α | URA knockout with 5-FOA selection | EBY100α | |
| EBY102a | Constitutive expression of Aga1 | EBY101a | pMOD_NatMX_HIS_pGPD-Aga1 |
| EBY102α | Constitutive expression of Aga1 | EBY101α | pMOD_NatMX_HIS_pGPD-Aga1 |
| WTa_mCher | MATa, Consttutive mCherry expression with WT SAG1 | EBY102a | pMOD_BleoMX_LTR2_pGPD-mChe |
| WTa_mTur | MATα, Consttutive mTurquoise expression with WT SAG1 | EBY102α | pMOD_BleoMX_LTR2_pGPD-mTur |
| EBY103a | MATa, Sag1 knockout | EBY102a | pYMOD_URA_KO_SAG1 |
| EBY103α | MATα, Sag1 knockout | EBY102α | pYMOD_URA_KO_SAG1 |
| Δsag1α_mTur | MATα, Consttutive mTurquoise expression with SAG1 KO | EBY103α | pMOD_BleoMX_LTR2_pGPD_mTur |
| EBY104a | MATa, CRE recombinase part A | EBY103a | pYMOD_KanMX_YCR043_pZ4-CRE |
| EBY104α | MATα, CRE recombinase part B | EBY103α | pYMOD_KanMX_YCR043_pACT1-ZEV4 |
| yNGYSDa | Final MATa parent strain, with Sce1 landing pad | EBY104a | pYMOD_BleoMX_ARS314_pGAL-Sce 1 |
| yNGYSDα | Final MATα parent strain, with Sce1 landing pad | EBY104α | pYMOD_BleoMX_ARS314_pGAL-Sce 1 |
| yNGYSDa_Bfl1 | MATa haploids used in pairwise and batched mating assays | yNGYSDa | pNGYSDa_Bfl1 |
| yNGYSDa_BclB | | yNGYSDa | pNGYSDa_BclB |
| yNGYSDa_Bcl2 | | yNGYSDa | pNGYSDa_Bcl2 |
| yNGYSDa_BclW | | yNGYSDa | pNGYSDa_BclW |
| yNGYSDa_BclXL | | yNGYSDa | pNGYSDa_BclXL |

TABLE 10-continued

List of yeast strains used in Example 6.

| Strain Name | Description | Parent | Transformant |
|---|---|---|---|
| yNGYSDa_Mcl1[151-321] | | yNGYSDa | pNGYSDa_Mcl1[151-321] |
| yNGYSDα_Bim.BH3 | MATα haploids used in pairwise and batched mating assays | yNGYSDα | pNGYSDα_Bim.BH3 |
| yNGYSDa_Noxa.BH3 | | yNGYSDα | pNGYSDα_Noxa.BH3 |
| yNGYSDα_Puma.MH3 | | yNGYSDα | pNGYSDα_Puma.BH3 |
| yNGYSDα_Bad.BH3 | | yNGYSDα | pNGYSDα_Bad.BH3 |
| yNGYSDα_Bik.BH3 | | yNGYSDα | pNGYSDα_Bik.BH3 |
| yNGY SDα_Hrk.BH3 | | yNGYSDα | pNGYSDα_Hrk.BH3 |
| yNGYSDα_Bmf.BH3 | | yNGYSDα | pNGYSDα_Bmf.BH3 |
| yNGYSDα_FINDI-F21 | | yNGYSDα | pNGYSDα_FINDI-F21 |
| yNGYSDα_FINDI-F30D | | yNGYSDα | pNGYSDα_FINDI-F30D |
| yNGYSDα_BINDI-B+ | | yNGYSDα | pNGYSDα_BINDI-B+ |
| yNGYSDα_BINDI-BCDP01 | | yNGYSDα | pNGYSDα_BINDI-BCDP01 |
| yNGYSDα_BINDI-B40A | | yNGYSDα | pNGYSDα_BINDI-B40A |
| yNGYSDα_2INDI-2+ | | yNGYSDα | pNGYSDα_2INDI-2+ |
| yNGYSDα_2INDI-4LVT | | yNGYSDα | pNGYSDα_2INDI-4LVT |
| yNGYSDα_WINDI-aBclW | | yNGYSDα | pNGYSDα_WINDI-aBCLW |
| yNGYSDα_XINDI-XCDP07 | | yNGYSDα | pNGYSDα_XINDI-XCDP07 |
| yNGYSDα_MINDI | | yNGYSDα | pNGYSDα_MINDI |

TWO-STRAIN MATING ASSAYS: For one-to-one mating assays, strains were grown to saturation in YPD from an isogenic colony. The relative surface expression strength of each strain was measured by washing 10 µL of cells at saturation, incubating in 50 µL PBSF media with FITC-anti-myc antibody for 15 minutes, washing, and measuring FITC fluorescence with the FL1.A channel on an ACCURI™ C6 cytometer. 2.5 µL of the MATa strain and 5 µL of the MATalpha strain were combined for mating in 3 mL of YPD and incubated at 30° C. and 275 RPM for 17 hours. 5 µL of culture was then added to 1 mL of water and run on a Miltenyi MACSQuant® VYB cytometer to measure cellular fluorescence of mCherry and mTurquoise with the Y2 and V1 channels, respectively. For all cytometry data, a yeast gate was applied and analysis was performed with FLOWJO™.

LIBRARY MATING ASSAYS: For library mating assays in which each isogenic strain was constructed individually and the barcode associated with each synthetic adhesion protein was determined with Sanger sequencing, one or both of the isogenic haploid strains from a one-to-one mating were replaced with a library of strains, all of the same mating type, displaying unique barcoded synthetic adhesion proteins. Each haploid strain in the library is individually grown to saturation, evaluated for surface expression strength as described previously, and mixed in equal volumes. 2.5 µL, if a MATa library, or 5 µL, if a MATalpha library, were then added to a mating as before. Following a 17 hour incubation, 100 µL were added to 50 mL of YPD with 400 mg/mL hygromycin and 100 nM β-estradiol (many-to-many matings only). After growing to saturation, cells were harvested by centrifugation, and lysed by heating to 70° C. for 5 min in 200 mM LiOAc and 1% SDS. Cellular debris was removed and incubated at 37° C. for 4 hours with 0.05 mg/mL RNase A. An ethanol precipitation was then performed to purify and concentrate the genomic DNA. A primary qPCR is performed to amplify the barcode region with standard adaptors and the PCR product is used as a template for a secondary qPCR to attach an index barcode and standard Illumina adaptors. This fragment is gel extracted, quantified with a Qubit and analyzed on a MiSeq next generation sequencer.

For large-scale library matings constructed with nuclease assisted chromosomal integration, mating type libraries are grown separately to saturation in 3 mL YPD media. 1 mL of the MATa culture and 2 mL of the MATalpha culture are mixed and genome prepped as previously described. This genomic DNA is used as a template for two separate qPCR reactions, one to amplify the MATa expression cassette and barcode and the other to amplify the MATalpha expression cassette and barcode. A secondary PCR is used to add different index barcodes and Illumina adaptors. These fragments are sequenced with a MiSeq. 2.5 µL of the MATa culture and 5 µL of the MATalpha culture are combined in 3 mL of YPD media and treated the same as for the small-scale batched mating.

SEQUENCE ANALYSIS AND STATISTICS: For small-scale libraries, barcode sequences for each SAP are determined with Sanger sequencing. For large-scale libraries, a next generation sequencing run is required to map each SAP to its barcode and to determine the starting concentration of each SAP expressing strain. Next generation sequencing of fragment amplified from diploid genomic DNA provides the frequency of each possible barcode pair occurring in the same fragment, which is translated to the mating frequency caused by a particular pair of SAPs.

Results

Figure 14A:
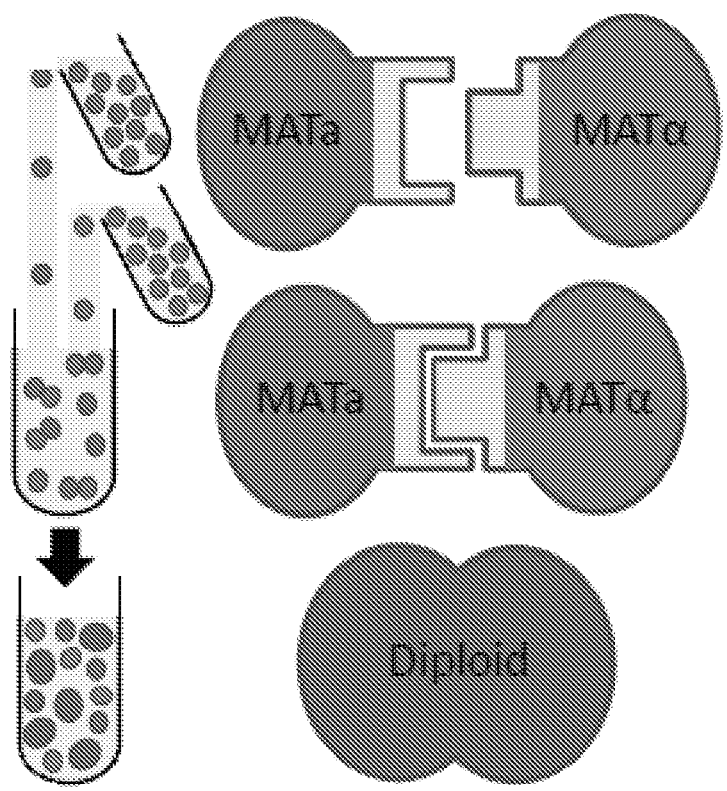
FIG. 14A-FIG. 14D show a schematic for the synthetic agglutination for the pairwise characterization of protein-protein interactions (PPIs).
Figure 14B:
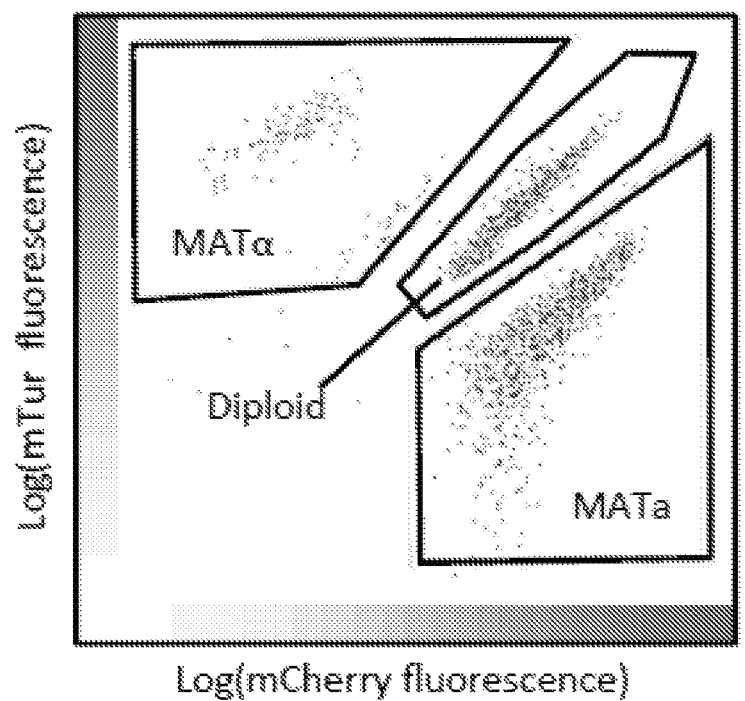
Figure 14C:
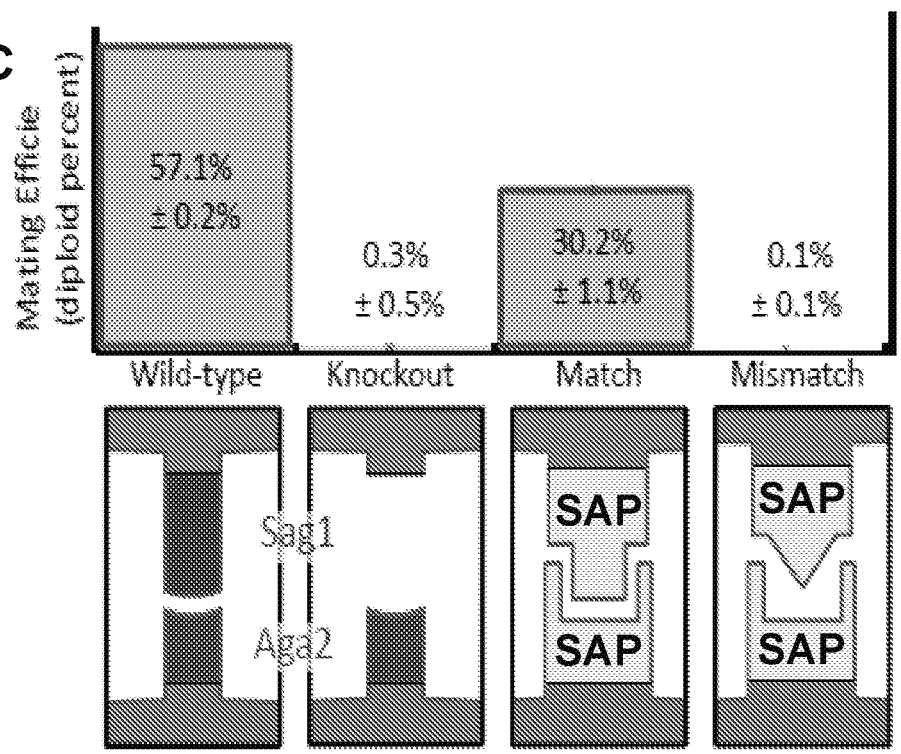

Reprogramming Sexual Agglutination: For the first time, complementary binding proteins expressed on the surface of yeast are shown to replace the function of the native sexual agglutinin proteins, Aga2 and Sag 1. Following the co-culture of MATa and MATalpha haploid cells, flow cytometry was performed to differentiate between mCherry expressing MATa haploids, mTurquoise expressing MATalpha haploids, and mated diploids that express both fluorescent markers (FIG. 14A, FIG. 14B). The diploid percent after a 17-hour co-culture was used as a metric for mating efficiency. Wild-type S. cerevisiae mates with an efficiency of nearly 60%. A knockout of Sag 1, the MATalpha sexual agglutinin protein, eliminates mating with wild-type MATa. Maintaining the Sag1 knockout, constitutive expression of synthetic agglutinin proteins (SAPs) that bind with an affinity similar to the native Sag 1-Aga2 interaction ($K_D$=2nM) recovers mating efficiency to above 30%, while expression of a non-interacting SAP pair ($K_D$>25 µM) shows no observable recovery (FIG. 14C). The use of a constitutive promoter for SAP expression was likely the cause for a discrepancy between wild-type and SAP recovered mating efficiency. Recovery of mating was demonstrated with a variety of natural and engineered proteins ranging from 26 to 206 amino acids, indicating a lack of structural restrictions for synthetic agglutination beyond interaction strength.

Prior to interaction screening, each SAP expressing yeast strain was tested for surface expression. False negatives for PPIs were observed only when one or both of the SAPs expressed poorly on the cell surface. Possible limitations to cell surface expression include protein size, stability, toxicity, and accessibility of both termini.

This example demonstrates that the function of the agglutinin proteins is entirely limited to binding, which can explain a wide diversity of related proteins in different yeast species. This example also demonstrates functional replacement of the sexual agglutinin proteins with unrelated binding proteins. Further, it is possible that genetic drift of the sexual agglutinin proteins may be responsible for yeast speciation. This example also demonstrates that orthogonal binding proteins expressed as SAPs can cause genetic isolation between two pairs of S. cerevisiae strains, an early step leading to speciation.

Figure 14D:
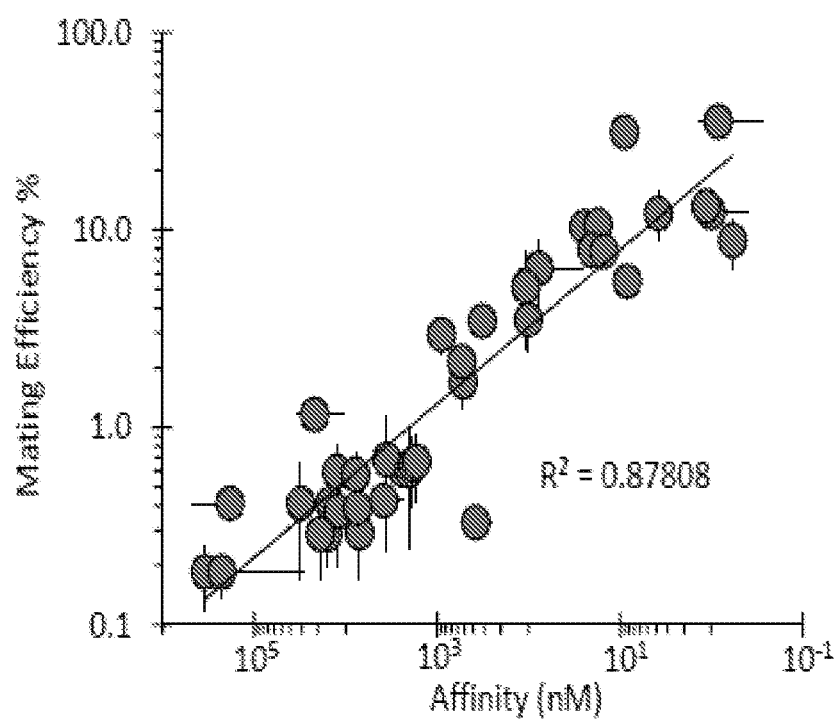
Figure 15:
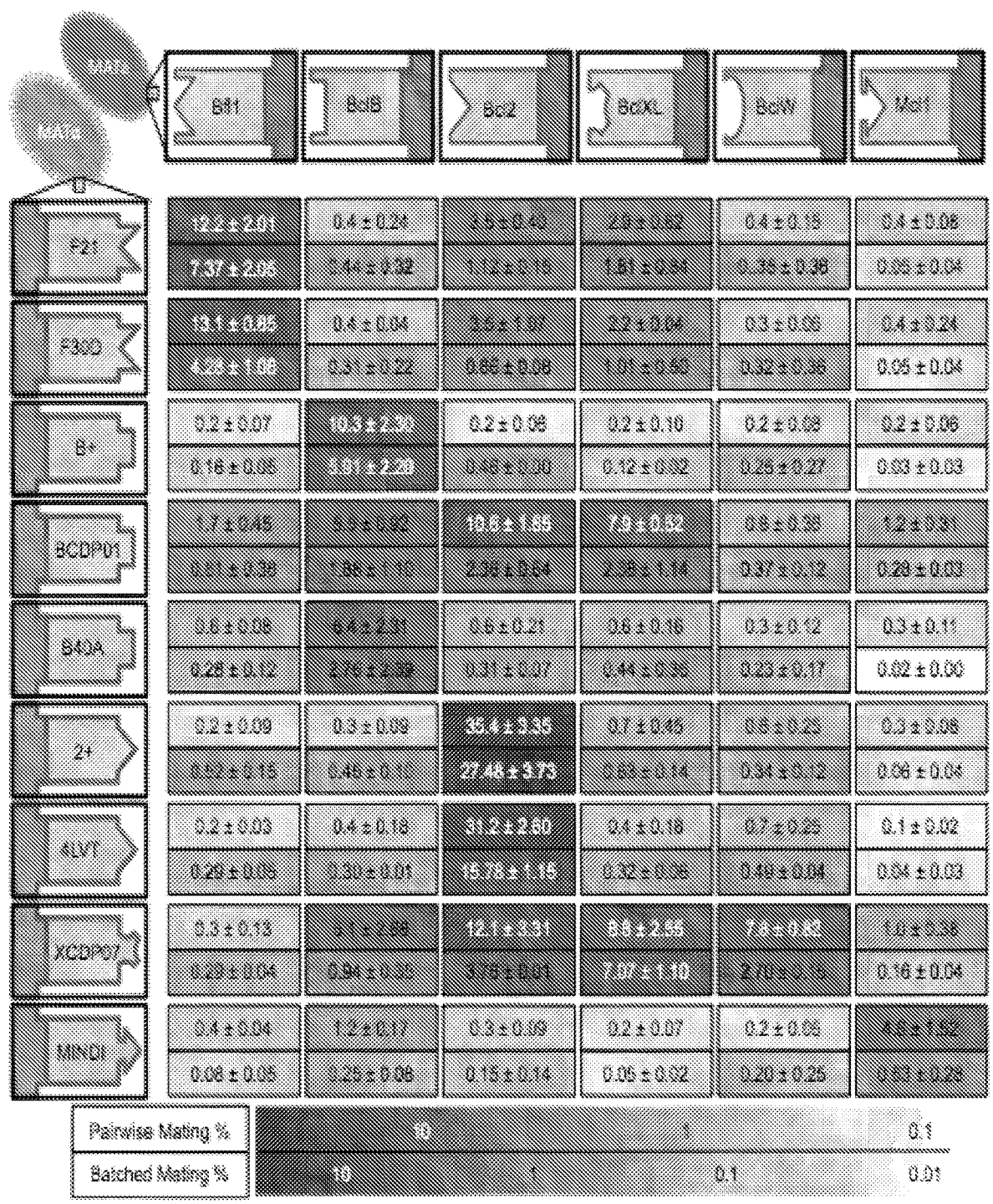
FIG. 15 shows the pairwise and batched mating percent for a PPI network consisting of 6 Bcl2 homologues and 9 de novo binding proteins. For each interaction, the pairwise mating percent is given on top with an error of one standard deviation from three biological replicates. The batched mating percent is given on the bottom with an error of one standard deviation from two biological replicates Shading provides a qualitative comparison between the two methods.
Figure 19:
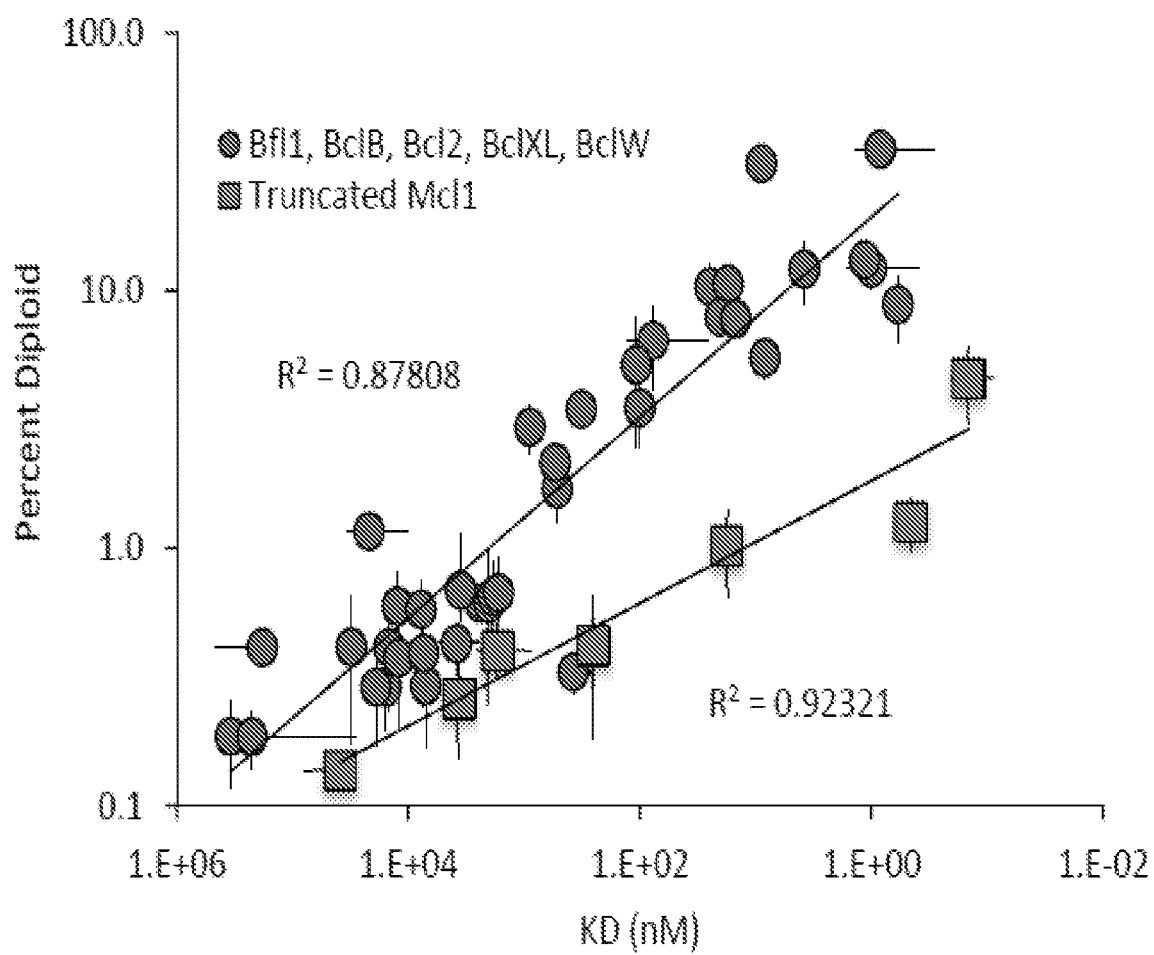
FIG. 19 shows that a truncation of Mcl1[151-321] likely results in different binding affinities with a panel of de novo protein binders. A plot of affinity of the full-length protein against mating efficiency of the truncated protein shows a strong monomial relationship with an $r^2$ of 0.92. However, there is a clear deviation between the slope for the truncated protein and for all other matings.
Figure 20A:
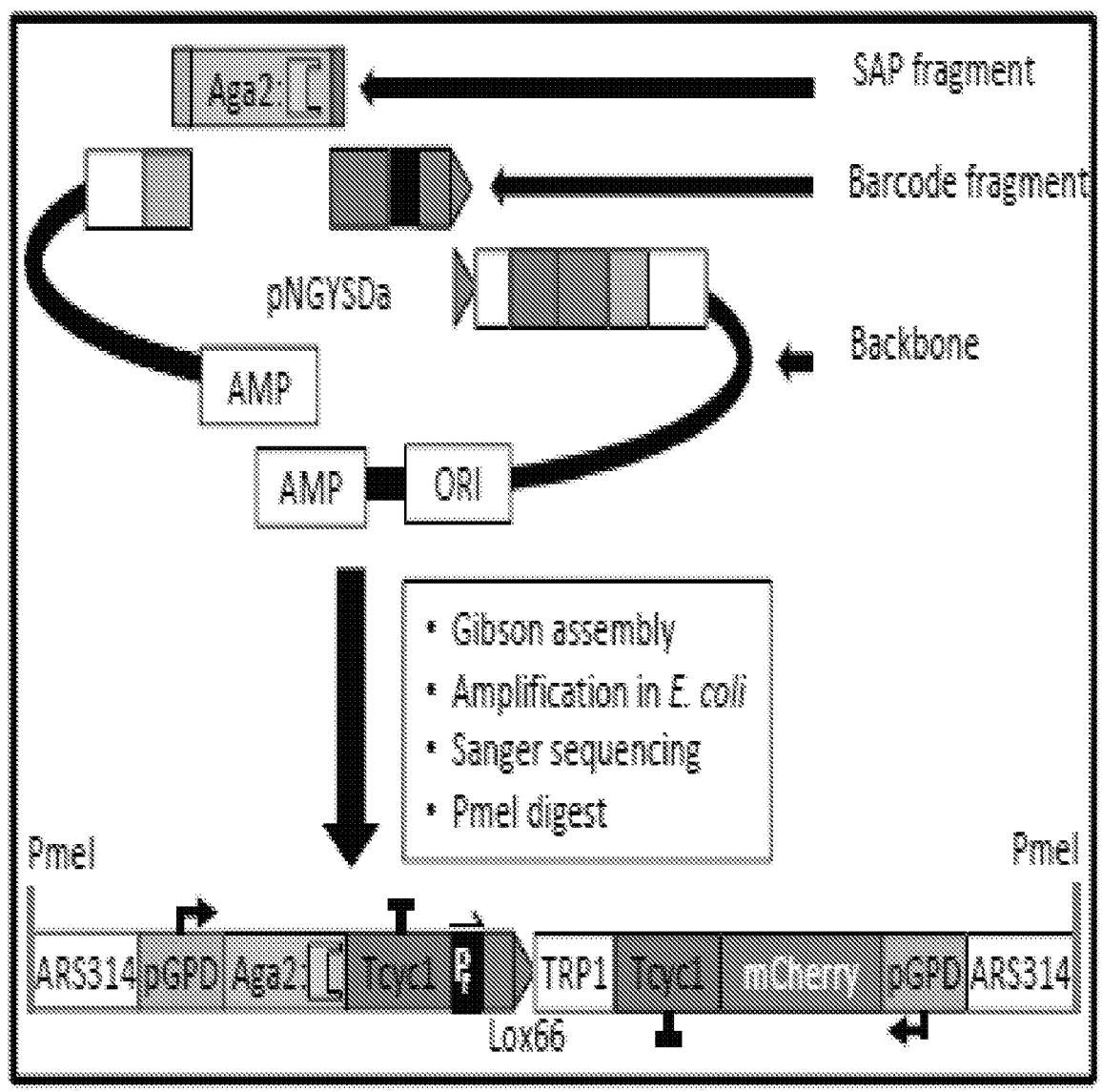
FIG. 20A-FIG. 20C show the construction strategy for plasmids and yeast strains.
Figure 20B:
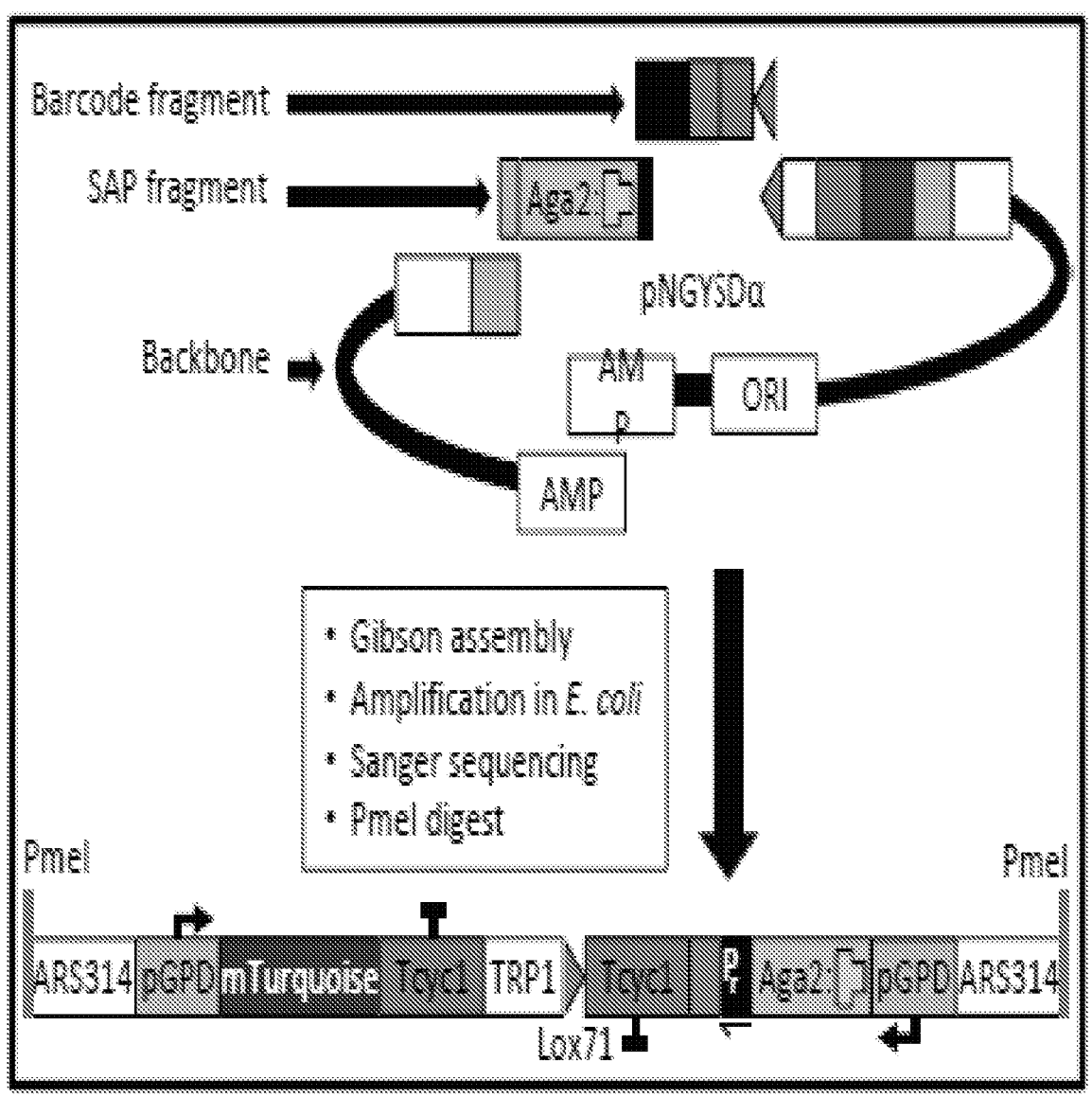
Figure 20C:
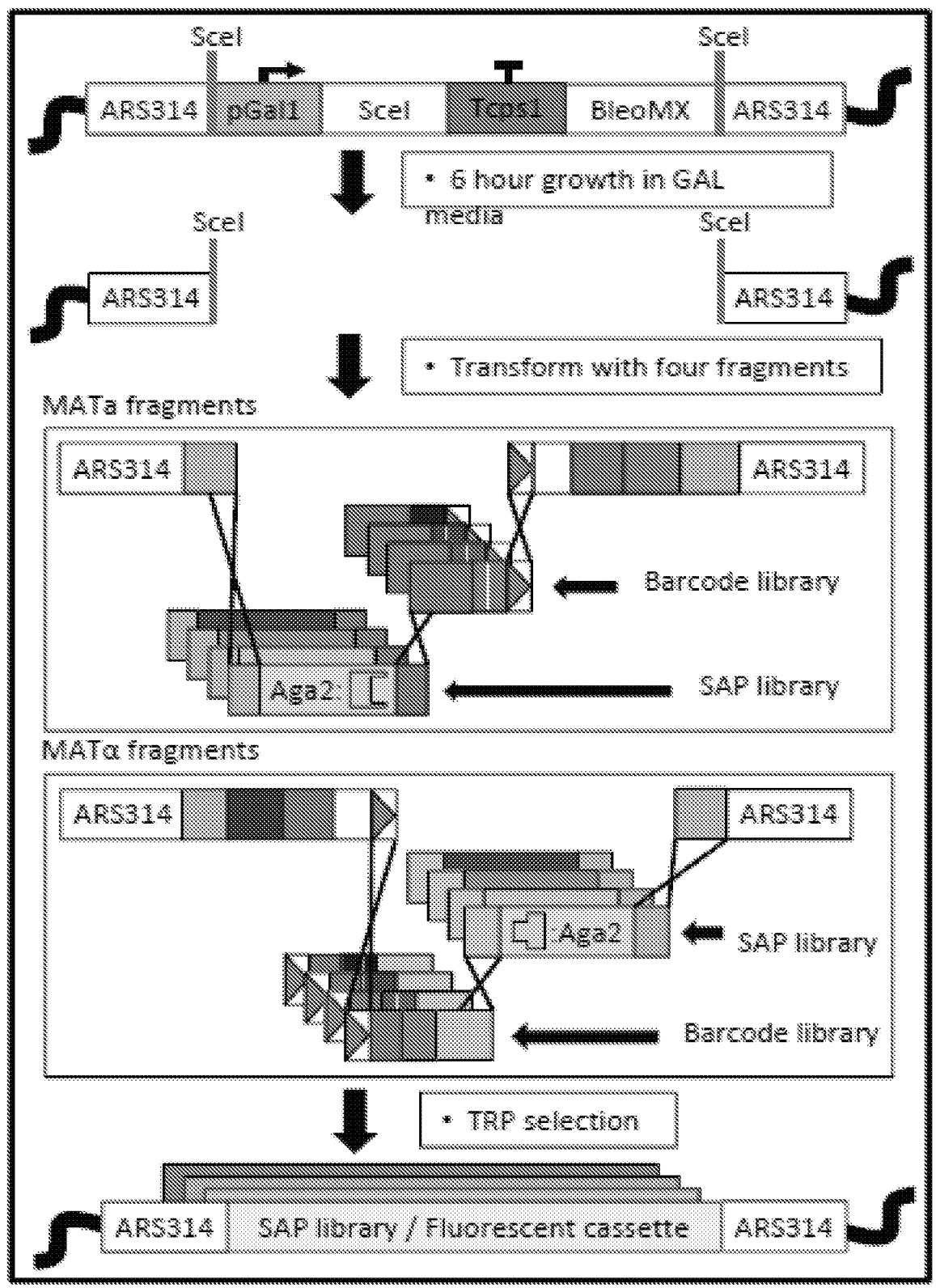

Quantitative PPI Characterization. Mating efficiency can be used to quantitatively determine the binding affinity of a SAP pair. A strong monomial relationship between mating efficiency and affinity was found for PPIs with a $K_D$ between 100 µM and 100 pM. The binding of the Bcl2 family apoptosis regulating proteins was tested with a panel of natural and engineered protein binders. A selection of the natural and engineered binding proteins representing a broad range of affinities were expressed as SAPs and their mating efficiencies measured with Bcl2 and five homologues in a pairwise manner. The mating efficiency and affinity of all highly expressing SAP pairs strongly fit a monomial relationship, with an $R^2$ of 0.88 (FIG. 14D). One Bcl2 homologue, Mcl1, showed no surface expression and no recovery of mating efficiency regardless of its mating partner. A truncation of Mcl1 improved surface expression but likely changed its binding properties (see FIG. 19). The relative mating efficiencies of truncated Mcl1 with all tested binding proteins are consistent with the known affinities of the full-length protein (FIG. 15).

A dynamic range of 100uM to 100pM for measuring affinities is suitable for most PPI characterization applications. Additionally, it may be possible to extend the dynamic range for measuring stronger interactions by increasing the concentration of blocking protein added to the media during mating. Unlike other assays for screening PPIs, we observed no false positives.

Figure 16A:
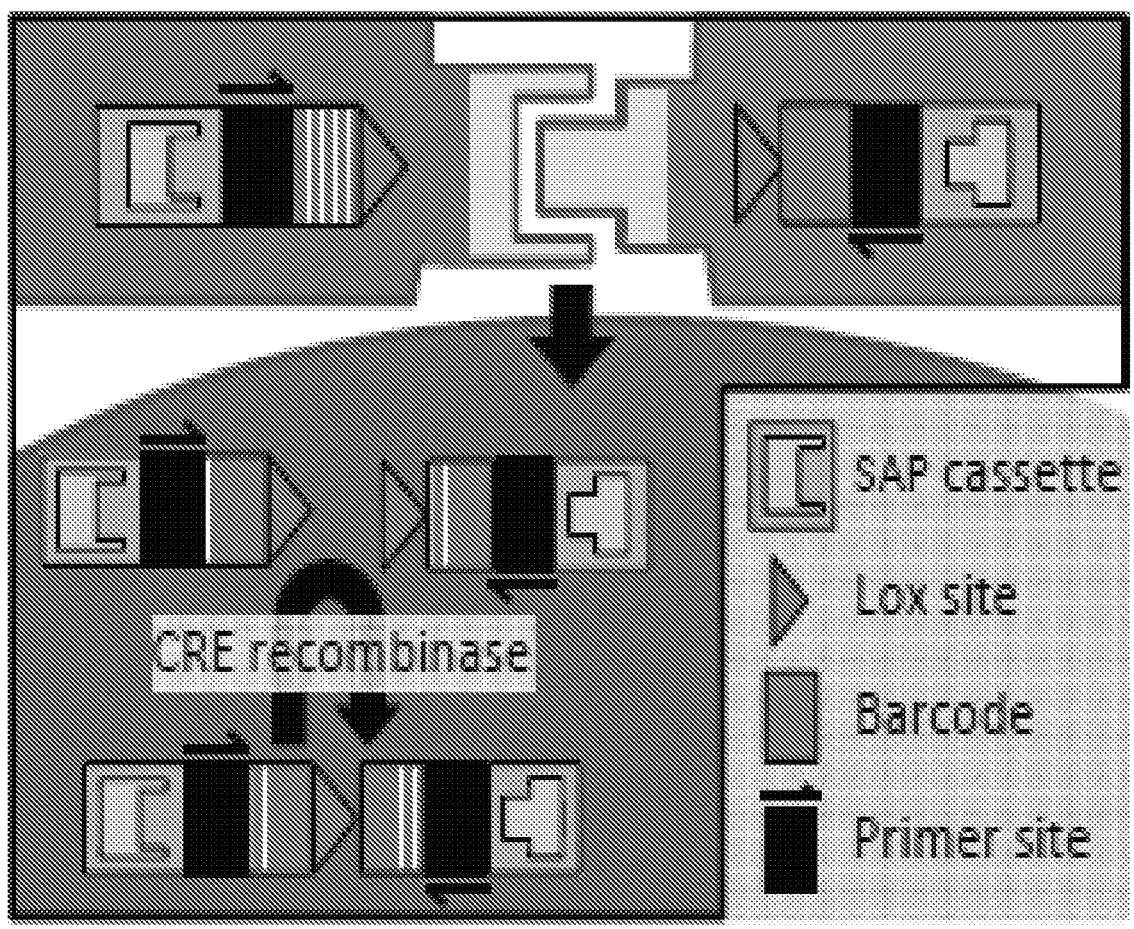
FIG. 16A-FIG. 16E show a one-pot PPI network characterization.

One-pot protein library characterization. A barcoding and recombination scheme was developed for the analysis of whole protein interaction networks in a single pot. Single MATa and MATα parent strain, yNGYSDa and yNGYSDα, were constructed and barcoded SAP cassettes were transformed into the strains. In addition to the knockout of Sag 1 in both parent strains and complementary lysine and leucine markers, yNGYSDa contains a CRE recombinase expression cassette with an inducible promoter, pZ4. yNGYSDα constitutively expresses ZEV4, an activator of the pZ4 promoter with an estradiol binding domain for nuclear localization. SAP cassettes were assembled in one of two standardized vectors, pNGYSDa or pNGYSDα, for integration into the corresponding yeast parent strain. In addition to the surface expression cassette, each vector backbone contains a mating type specific florescent reporter cassette, a randomized ten-nucleotide barcode, a mating type specific primer binding site, and a lox recombination site. Upon mating, the addition of β-Estradiol (βE) induces CRE recombinase expression in diploid cells, consolidating the barcodes from each haploid chromosome so that next-generation sequencing can be used to count the frequency of interacting SAP pairs (FIG. 16A). The batched mating percent for each interaction in the network is calculated from the raw interaction counts, providing a relative interaction strength for each PPI in the network.

Figure 16B:
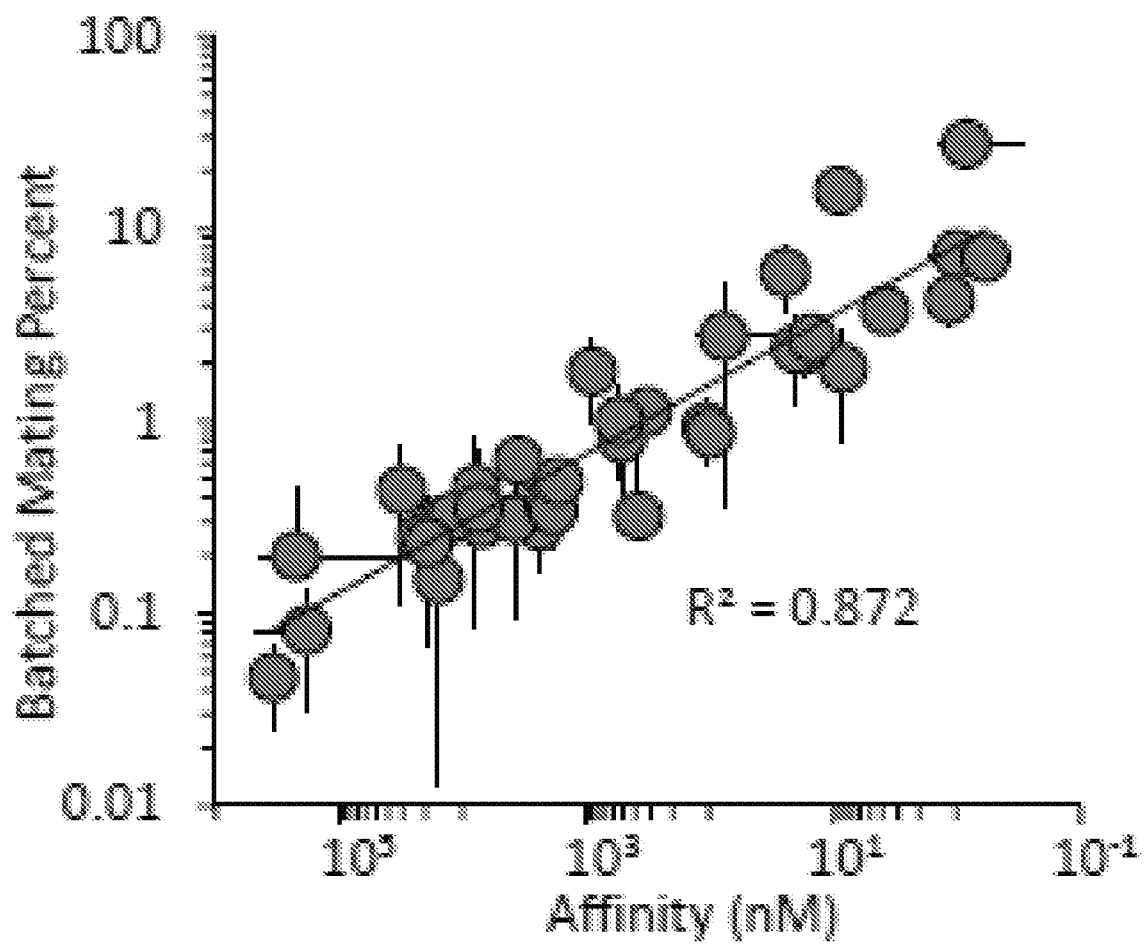
Figure 16C:
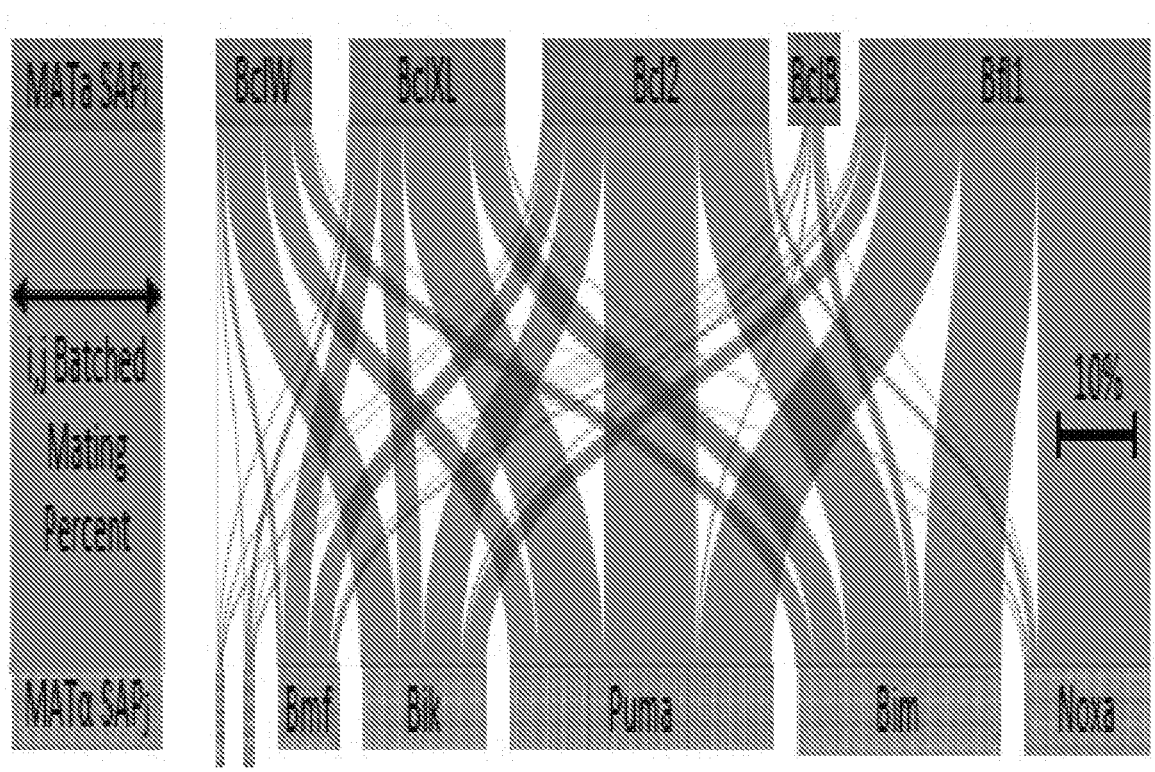
Figure 16D:
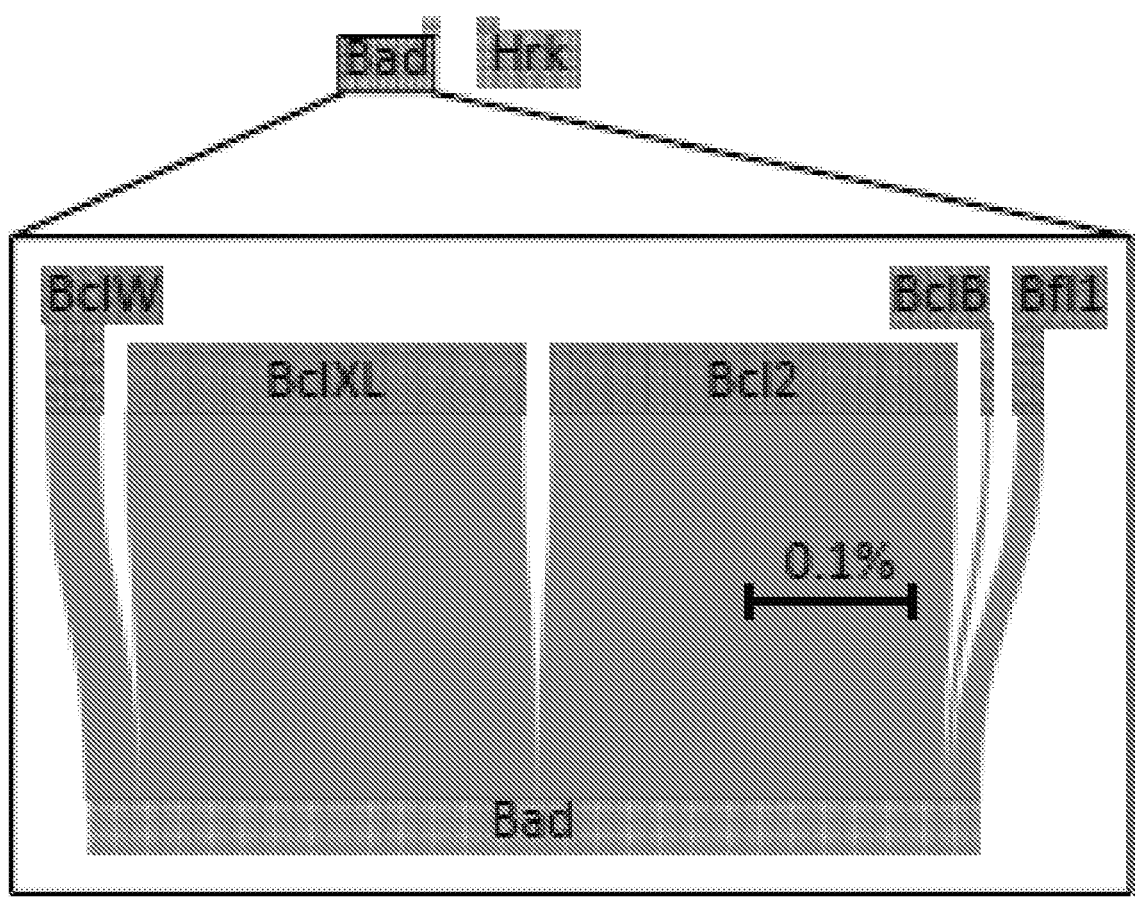
Figure 16E:
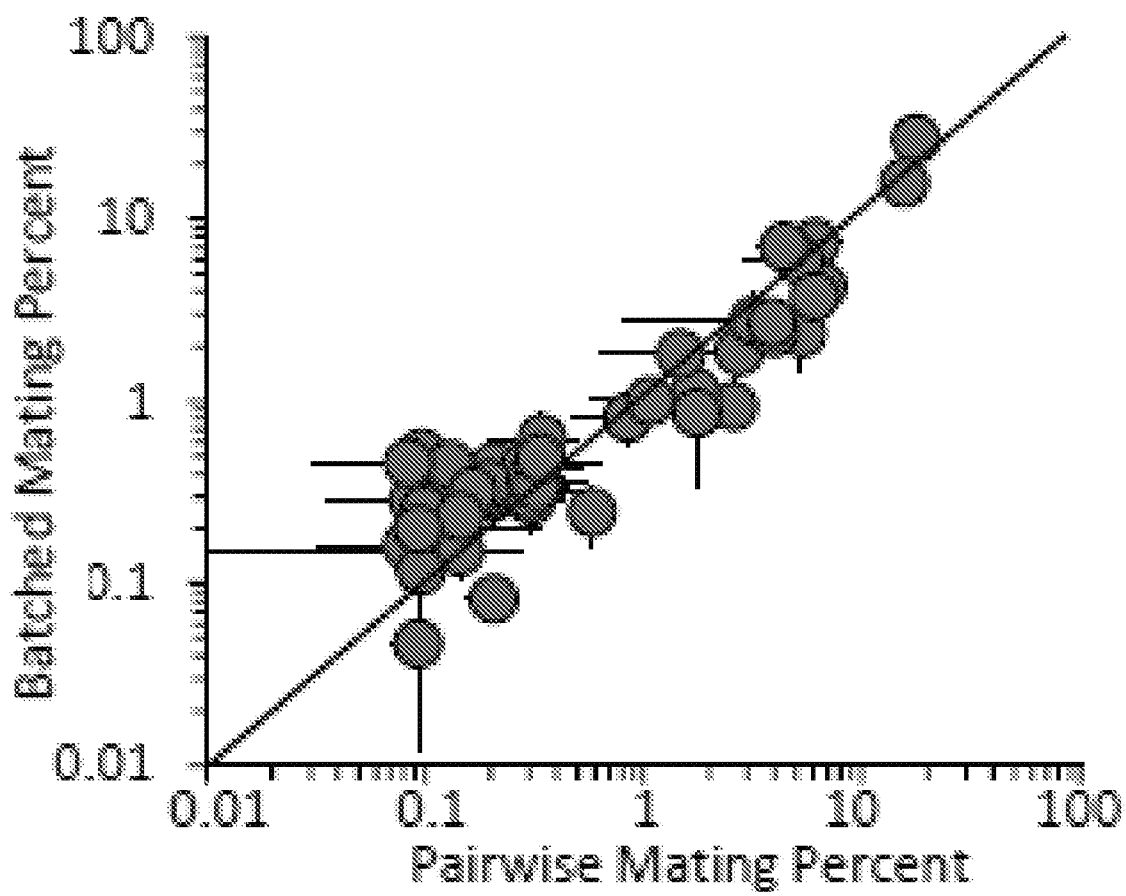
Figure 17:
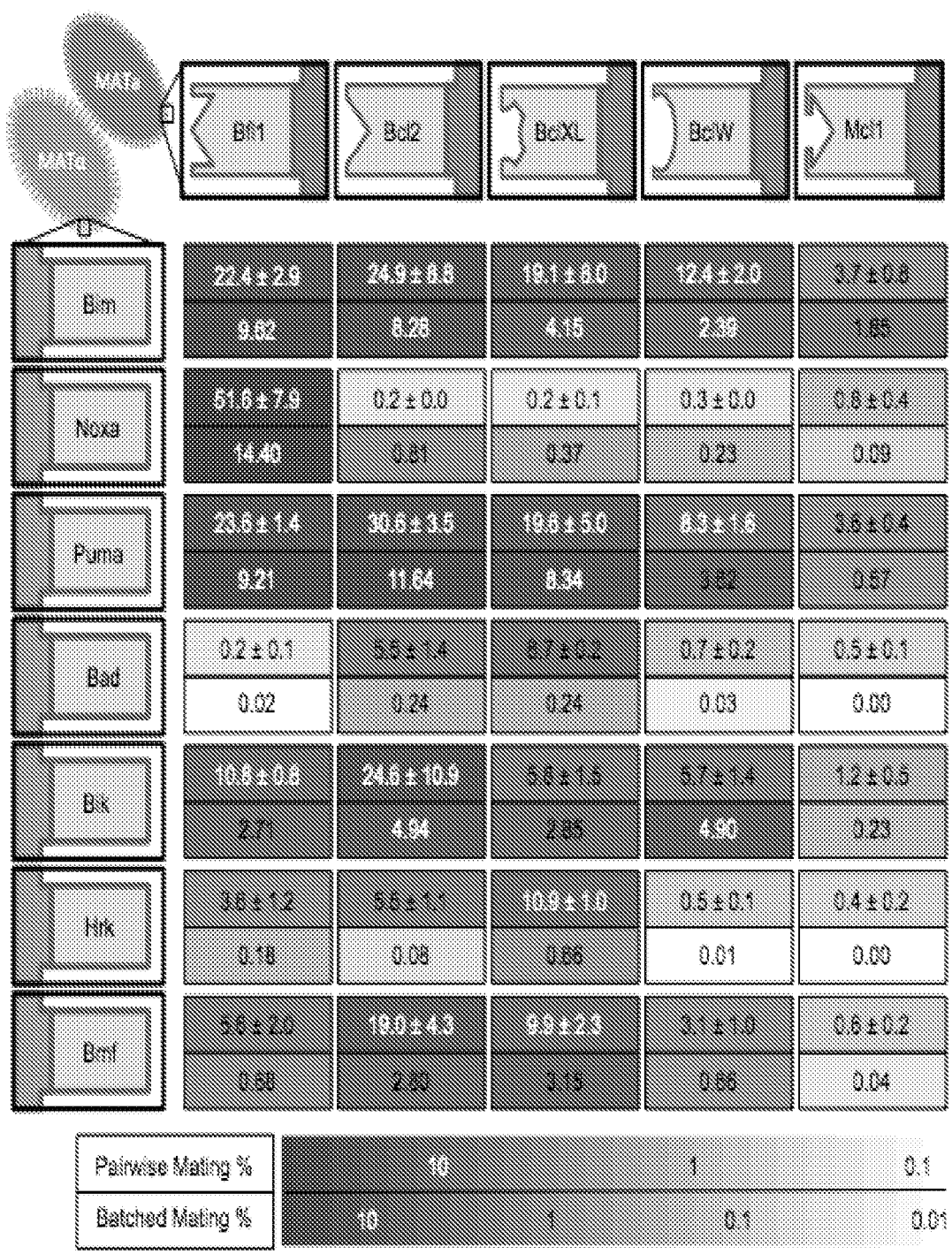
FIG. 17 shows the pairwise and batched mating percent for a PPI network consisting of 5 Bcl2 homologues and 7 BH3 domain peptides. For each interaction, the pairwise mating percent is given on top with an error of one standard deviation from three biological replicates. The batched mating percent is given on the bottom Shading provides a qualitative comparison between the two methods.

To test the batched mating approach, the interaction network between the Bcl2 family proteins and their natural and engineered binders was reanalyzed (FIG. 17). From a one-pot mating, a strong monomial relationship was observed between affinity and batched mating percent for all surface expressing protein pairs, with an $r^2$ of 0.87 (FIG. 16B). In addition to the de novo binding proteins, seven natural peptide binders with a range of target specificities were added to a batched mating. The interaction profile between these peptides and the five Bcl2 family protein targets is consistent with previous work. For example, Noxa is confirmed to bind to Bfl 1 with high specificity and both Bim and Puma are confirmed to bind nonspecifically to BclW, BclXL, Bcl2, and Bfl1 (FIG. 16C). Even Bad, which interacts more weakly overall, gives the expected interaction profile: strong binding to BclXL and Bcl2, weak binding to BclW, and minimal binding to BclB and Bfl1 (FIG. 16D). A comparison of the pairwise and one-pot methods shows a near perfect 1:1 agreement (FIG. 16E). The batched mating assay likely gives a higher resolution than the pairwise assays, especially for weak interactions.

Figure 18A:
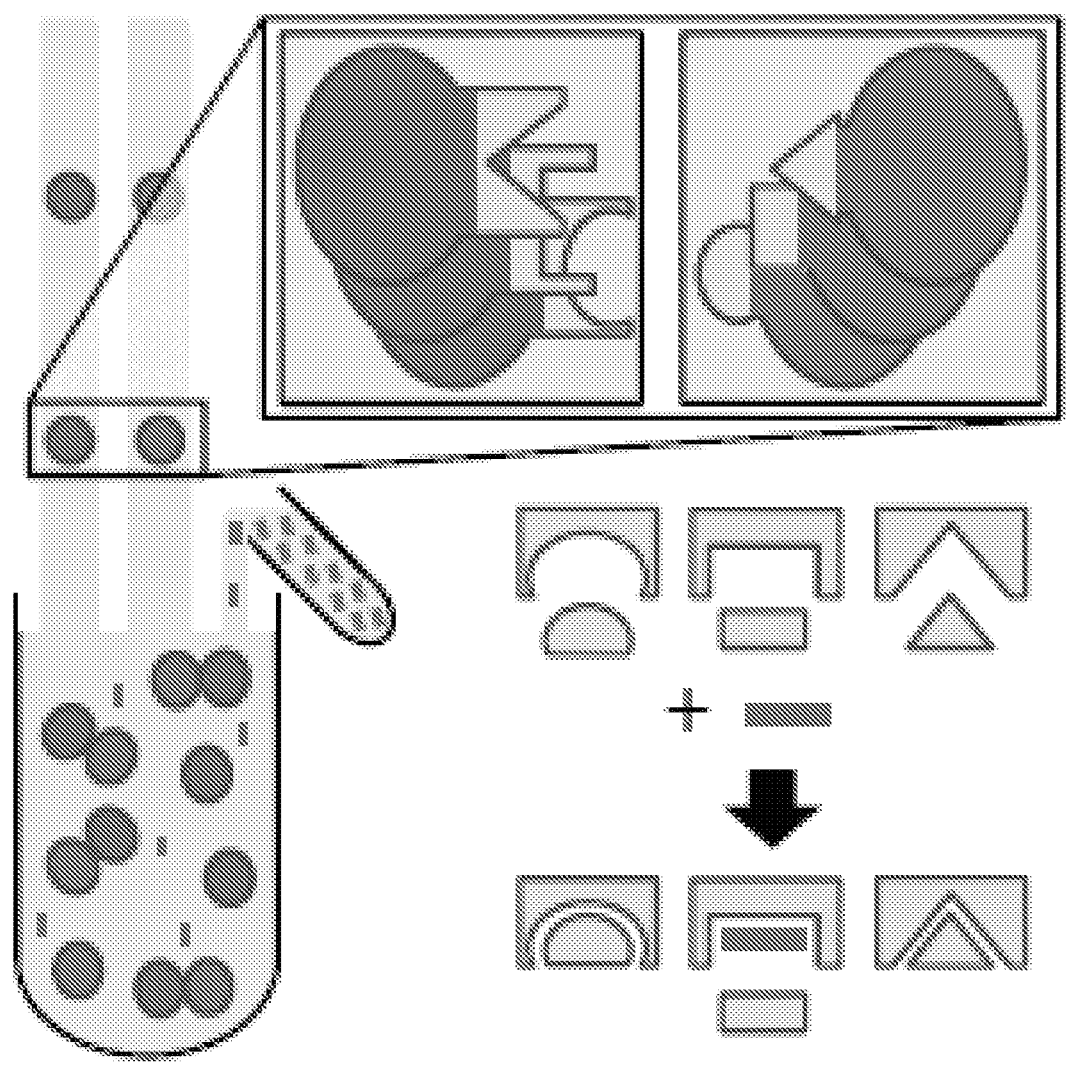
FIG. 18A-FIG. 18C show changing the binding environment.
Figure 18B:
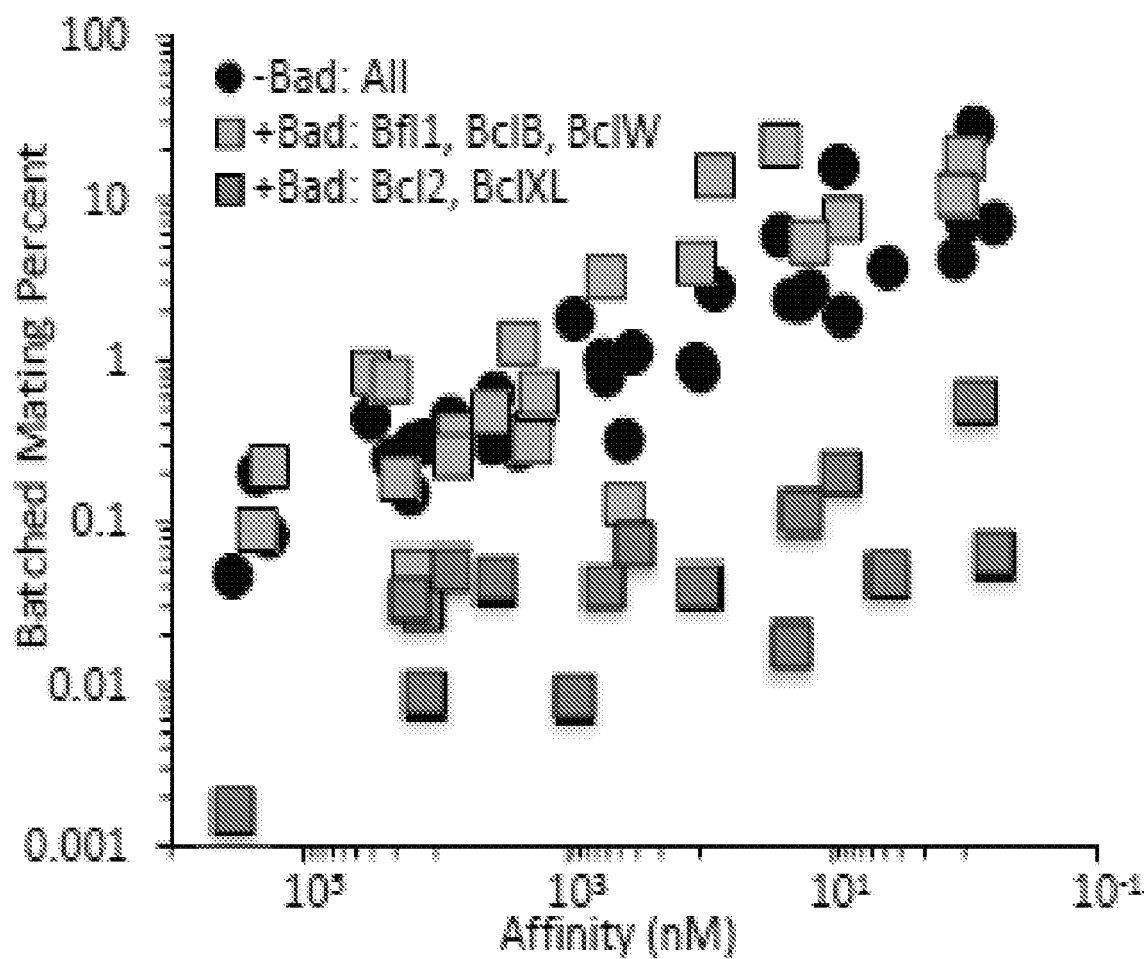
Figure 18C:
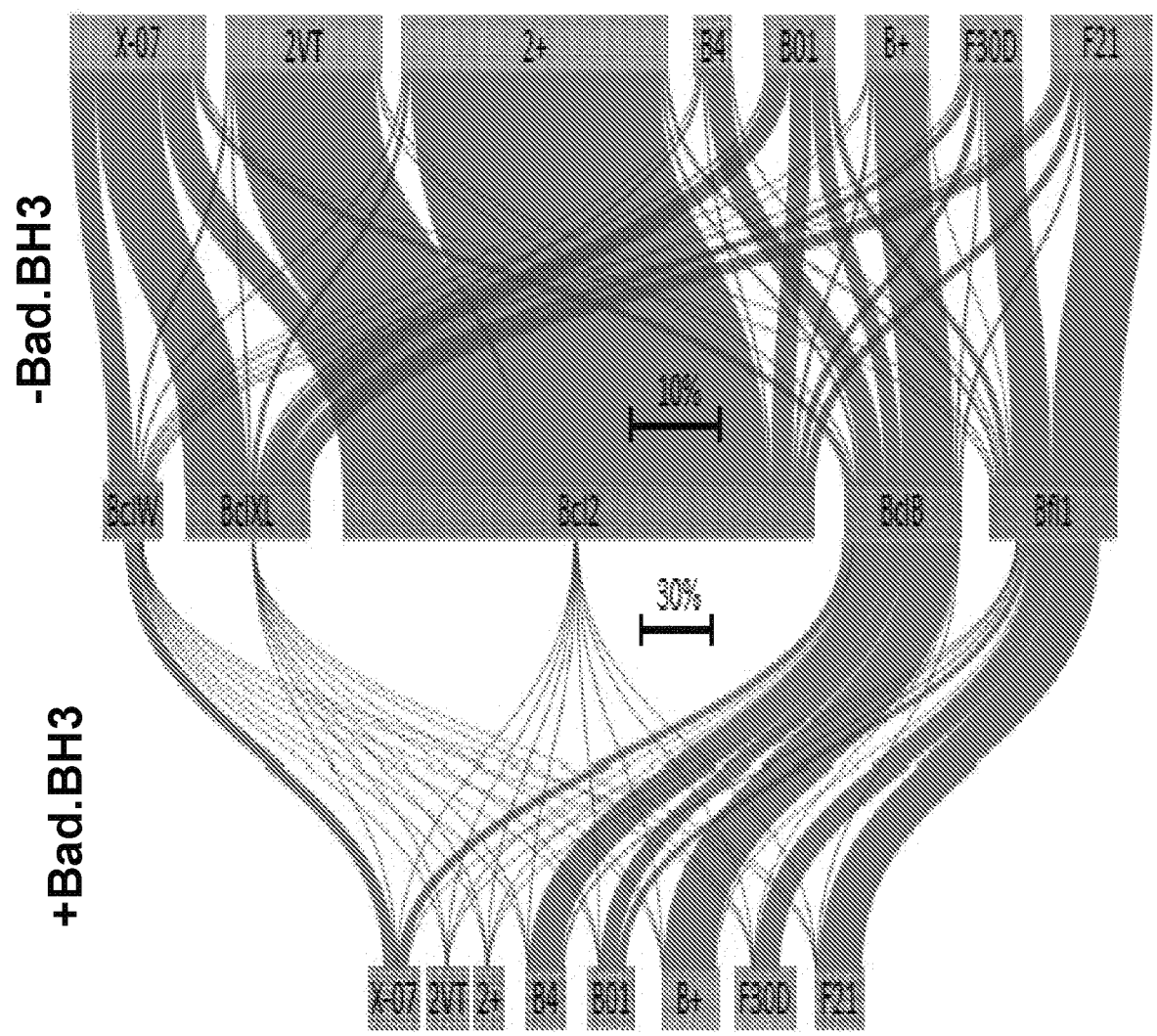

PPI network response to environmental changes. A major advantage of an extracellular protein interaction assay is the ability to control the binding environment beyond what is possible intracellularly due to transport and toxicity. This example demonstrates that a non-membrane soluble competitor that is added exogenously to a batched mating disrupts only the expected PPIs (FIG. 18A). Returning again to the interaction network of the Bcl2 family proteins and their de novo binding partners, that one peptide, Bad, was shown bound with high specificity to BclXL and Bcl2. Now, by adding Bad at a concentration of 100nM to a batched mating, a highly specific disruption of only those interactions that include BclXL or Bcl2 was observed (FIG. 18B, FIG. 18C). The batched mating percents with the addition of Bad were normalized to the batched mating percents without Bad with the assumption that interactions involving Bc1B are unaffected by the presence of Bad.

Large library characterization and validation. For the construction of a large chromosomally integrated library, DNA nicking at the site of integration was required to improve homologous recombination efficiency. This was achieved with the integration of a SceI cut site flanked landing pad at the site of library integration. Transformation using this approach resulted in over 10,000 transformants.

Many of the yeast strains described in this disclosure required multiple transformations. Displayer strains compatible with the CRE recombinase assay, for example, required the integration of Aga1 under the control of a constitutive promoter, the knockout of a sexual agglutinin protein, the integration of a fluorescent reporter, the integration of CRE recombinase and GAVN or of HygMX and ZEV4, and the integration of a barcoded surface expression cassette with a lox site. For each integration, a plasmid must be constructed that contains the required yeast cassette, an E. coli resistance marker and origin of replication, and 5' and 3' regions of homology to the yeast genome for integration.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

While the invention has been particularly shown and described with reference to an aspect and various alternate aspects, it will be understood by persons skilled in the relevant art that various changes in form and details can be made therein without departing from the spirit and scope of the invention. The description of embodiments of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize All references, issued patents and patent applications cited within the body of the instant specification are hereby incorporated by reference in their entirety, for all purposes. Aspects of the disclosure can be modified, if necessary, to employ the systems, functions, and concepts of the above references and application to provide yet further embodiments of the disclosure. These and other changes can be made to the disclosure in light of the detailed description.

REFERENCES

BALAGADDÉ et al. "A synthetic Escherichia coli predator-prey ecosystem." *Molecular systems biology* 4.1 (2008): 187.
BARTON et al. "Why sex and recombination?" *Science* 281.5385 (1998): 1986-1990.
BENDER et al. "Pheromones and pheromone receptors are the primary determinants of mating specificity in the yeast Saccharomyces cerevisiae." *Genetics* 121.3 (1989): 463-76.
BODER et al. "Yeast surface display system for antibody engineering." *Immunotechnology* 2.4 (1996):283-283.
BODER et al. "Yeast surface display for screening combinatorial polypeptide libraries." *Nature biotechnology* 15.6 (1997): 553-557.
BODER et al. "Yeast surface display of a noncovalent MHC class II heterodimer complexed with antigenic peptide." *Departmental Papers* (CBE)(2005): 61.
CARDINALE et al. "Contextualizing context for synthetic biology-identifying causes of failure of synthetic biological systems."*Biotechnology journal* 7.7 (2012): 856-866.
CASINI et al. "R2oDNA designer: computational design of biologically neutral synthetic DNA Sequences." *ACS synthetic biology* 3.8 (2014): 525-528.
CHAN et al. "Isolation and genetic analysis of Saccharomyces cerevisiae mutants supersensitive to G1 arrest by a factor and alpha factor pheromones." *Molecular and Cellular Biology* 2.1 (1982): 11-20.
CHAO et al. "Fine epitope mapping of anti-epidermal growth factor receptor antibodies through random mutagenesis and yeast surface display." *Journal of molecular biology* 342.2 (2004): 539-550.
CHEE et al. "New and redesigned pRS plasmid shuttle vectors for genetic manipulation of Saccharomyces cerevisiae." *G3: Genes Genomes Genetics* 2.5 (2012): 515-526.
CHEN et al. "Cell-cell fusion." *FEBS letters* 581.11 (2007): 2181-2193.
CHENEVERT et al. "Identification of genes required for normal pheromone-induced cell polarization in Saccharomyces cerevisiae." *Genetics* 136.4 (1994): 1287-1296.
COLEGRAVE, Nick. "Sex releases the speed limit on evolution." *Nature* 420.6916 (2002): 664-666.
DAAR et al. "Top ten biotechnologies for improving health in developing countries." *Nature genetics* 32.2 (2002):
DANIEL et al. "Synthetic analog computation in living cells." *Nature* 497.7451 (2013): 619-623.
DAUGHERTY et al. "Antibody affinity maturation using bacterial surface display." *Protein engineering* 11.9 (1998): 825-832.
DRANGINIS et al. "A Biochemical Guide to Yeast Adhesins: Glycoproteins for Social and Antisocial Occasions." *Microbiology and Molecular Biology Reviews* 71.2 (2007): 282-294.
DUNHAM, "Synthetic ecology: a model system for cooperation. "*Proceedings of the National Academy of Sciences* 104.6 (2007): 1741-1742.
DUNN et al. "Natural and sexual selection act on different axes of variation in avian plumage color." *Science Advances* 1.2 (2015): e1400155.
DURA et al. "Spatially and temporally controlled immune cell interactions using microscale tools." *Current opinion in immunology* 35 (2015): 23-29.
FLETCHER et al. "A basis set of de novo coiled-coil peptide oligomers for rational protein design and synthetic biology." *ACS synthetic biology* 1.6 (2012): 240-250.
GAI et al. "Yeast surface display for protein engineering and characterization." *Current opinion in structural biology* 17.4 (2007): 467-473.
GIBSON et al. "Enzymatic assembly of DNA molecules up to several hundred kilobases." *Nature methods* 6.5 (2009): 343-345.

GREIG et al. "Hybrid speciation in experimental populations of yeast." *Science* 298.5599 (2002): 1773-1775.

GU et al. "Multiplex single-molecule interaction profiling of DNA-barcoded proteins." *Nature* (2014).

GUO et al. "A Saccharomyces gene family involved in invasive growth, cell-cell adhesion, and mating." *Proceedings of the National Academy of Sciences* 97.22 (2000): 12158-12163.

HEAD et al. "Female mate preferences for male body size and shape promote sexual isolation in threespine sticklebacks." *Ecology and evolution* 3.7 (2013): 2183-2196.

HOWITT et al. "Technologies for global health." *The Lancet* 380.9840 (2012): 507-535.

HUANG et al. "Conserved WCPL and CX4C domains mediate several mating adhesin interactions in Saccharomyces cerevisiae." *Genetics* 182.1 (2009): 173-189.

ITO et al. "Transformation of intact yeast cells treated with alkali cations."*Journal of bacteriology* 153.1 (1983): 163-168.

JACKSON et al. "Courtship in Saccharomyces cerevisiae: an early cell-cell interaction during mating."*Molecular and Cellular Biology* 10.5 (1990): 2202-2213.

KASTER et al. "Hygromycin B resistance as dominant selectable marker in yeast." *Current genetics* 8.5 (1984): 353-358.

KEDDAR et al. "Color ornaments and territory position in king penguins." *Behavioural processes* 119 (2015): 32-37.

KHAKHAR et al. "Cell-Cell Communication in Yeast Using Auxin Biosynthesis and Auxin Responsive CRISPR Transcription Factors." *ACS synthetic biology* (2015).

LIPKE et al. "Sexual agglutination in budding yeasts: structure, function, and regulation of adhesion glycoproteins." *Microbiological reviews* 56.1 (1992): 180-194.

MALLESHAIAH et al. "The scaffold protein Ste5 directly controls a switch-like mating decision in yeast." *Nature* 465.7294 (2010): 101-105.

MARTINS et al. "Evolution and stability of ring species." *Proceedings of the National Academy of Sciences*110.13 (2013): 5080-5084.

MCISAAC et al. "Synthetic gene expression perturbation systems with rapid, tunable, single-gene specificity in yeast." *Nucleic acids research* (2012): gks1313.

NASMYTH, Kim. "Molecular genetics of yeast mating type." *Annual review of genetics* 16.1 (1982):439-500.

PARRISH et al. "Yeast two-hybrid contributions to interactome mapping." *Current opinion in biotechnology* 17.4 (2006): 387-393.

PROCKO et al. "A computationally designed inhibitor of an Epstein-Barr viral Bcl-2 protein induces apoptosis in infected cells." *Cell* 157.7 (2014): 1644-1656.

PUT et al. "The heat resistance of ascospores of four Saccharomyces spp. isolated from spoiled heat-processed soft drinks and fruit products." *Journal of Applied Bacteriology* 52.2 (1982): 235-243.

RODRÍGUEZ et al. "Diversification under sexual selection: the relative roles of mate preference strength and the degree of divergence in mate preferences." *Ecology letters* 16.8 (2013): 964-974.

SAUER, "Functional expression of the cre-lox site-specific recombination system in the yeast Saccharomyces cerevisiae." *Molecular and cellular biology* 7.6 (1987): 2087-2096.

SAFRAN et al. "Contributions of natural and sexual selection to the evolution of premating reproductive isolation: a research agenda." *Trends in ecology& evolution* 28.11 (2013): 643-650.

SEGALL, "Polarization of yeast cells in spatial gradients of alpha mating factor." *Proceedings of the National Academy of Sciences* 90.18 (1993): 8332-8336.

SHOU et al. "Synthetic cooperation in engineered yeast populations." *Proceedings of the National Academy of Sciences* 104.6 (2007): 1877-1882.

SREEKRISHNA et al. "Construction of strains of Saccharomyces cerevisiae that grow on lactose." *Proceedings of the National Academy of Sciences* 82.23 (1985): 7909-7913.

SUNDSTROM, "Adhesins in Candida albicans." *Current opinion in microbiology* 2.4 (1999): 353-357.

TERRANCE et al. "Sexual agglutination in Saccharomyces cerevisiae." *Journal of bacteriology* 148.3 (1981): 889-896.

THOMPSON et al. "SYNZIP protein interaction toolbox: in vitro and in vivo specifications of heterospecific coiled-coil interaction domains." *ACS synthetic biology* 1.4 (2012): 118-129.

VIDAL, "Interactome modeling." *FEBS letters* 579.8 (2005): 1834-1838.

WAHLBOM et al. "Molecular analysis of a Saccharomyces cerevisiae mutant with improved ability to utilize xylose shows enhanced expression of proteins involved in transport, initial xylose metabolism, and the pentose phosphate pathway." *Applied and environmental microbiology* 69.2 (2003): 740-746.

WANG et al. "A modular cell-based biosensor using engineered genetic logic circuits to detect and integrate multiple environmental signals." *Biosensors and Bioelectronics* 40.1 (2013): 368-376.

WANG et al. "Three-dimensional reconstruction of protein networks provides insight into human genetic disease." *Nature biotechnology* 30.2 (2012): 159-164.

WEBER, Wilfried, et al. "Emerging biomedical applications of synthetic biology." *Nature Reviews Genetics* 13.1 (2012): 21-35.

WEN et al. "Yeast surface display of trifunctional minicellulosomes for simultaneous saccharification and fermentation of cellulose to ethanol." *Applied and environmental microbiology* 76.4 (2010): 1251-1260.

WILSON et al. "The LoxP/CRE system and genome modification." Gene Knockout Protocols. Humana Press, 2001. 83-94.

XIE et al. "Accelerated and adaptive evolution of yeast sexual adhesins." *Molecular biology and evolution* (2011): msr145.

ZHAO et al. "Interaction of α-agglutinin and a-agglutinin, Saccharomyces cerevisiae sexual cell adhesion molecules." *Journal of bacteriology* 183.9 (2001): 2874-2880.

The invention claimed is:

1. A method of detecting a protein-protein interaction between cell surface proteins, the method comprising:

(a) providing a first plurality of haploid yeast cells of a first mating type, the first plurality of cells comprising a library of first gene expression cassettes, wherein each gene expression cassette in the library comprises:
a nucleic acid sequence encoding a first selectable marker, a first unique oligonucleotide molecular barcode sequence operatively linked to a first recombination site, and a nucleic acid sequence encoding one protein of a first library of cell surface proteins, such that each unique oligonucleotide molecular barcode is operably linked to the nucleic acid sequence encoding one protein of the first library of cell surface proteins;

(b) providing a second plurality of haploid yeast cells of a second mating type, the second plurality of cells comprising a library of second gene expression cassettes, wherein each gene expression cassette in the library comprises:
a nucleic acid sequence encoding a second selectable marker, a second unique oligonucleotide molecular barcode sequence operatively linked to a second recombination site, and a nucleic acid sequence encoding one protein of a second library of cell surface proteins, such that each unique oligonucleotide molecular barcode is operably linked to the nucleic acid sequence encoding one protein of the second library of cell surface proteins,
wherein the first library of cell surface proteins encoded by the library of first gene expression cassettes and the second library of cell surface proteins encoded by the library of second gene expression cassettes comprise potential binding pairs between the first library of cell surface proteins and the second library of cell surface proteins;

(c) contacting the first plurality of haploid yeast cells with the second plurality of haploid yeast cells under liquid culture conditions that promote contact between the first plurality of haploid yeast cells and the second plurality of haploid yeast cells when a specific binding interaction between one protein of the first library of cell surface proteins encoded by the library of first gene expression cassettes and one protein of the second library of cell surface proteins encoded by the library of second gene expression cassettes occurs, wherein the specific binding interaction promotes mating of the first and second plurality of haploid yeast cells to produce diploid yeast cells;

(d) recombining within the diploid cells one or more nucleotides of the gene expression cassettes to generate a recombined molecular barcode sequence comprising at least one or more nucleotides of the first unique oligonucleotide barcode operably linked to the nucleic acid sequence encoding one protein of the first library of cell surface proteins and one or more nucleotides of the second unique oligonucleotide molecular barcode operably linked to the nucleic acid sequence encoding one protein of the second library of cell surface proteins; and (e) sequencing the recombined molecular barcode sequence from the diploid cells to identify a surface protein from the library of first gene expression cassettes and a cell surface protein from the library of second gene expression cassettes that interact, thus detecting a protein-protein interaction between the cell surface proteins.

2. The method of claim 1, wherein the library of first gene expression cassettes is carried by a library of first plasmids, the library of second gene expression cassettes is carried by a library of second plasmids, and the liquid culture conditions that promote contact between the first plurality of haploid yeast cells and the second plurality of haploid yeast cells are dilute liquid culture conditions wherein the first plurality of haploid yeast cells and the second plurality of haploid yeast cells have been diluted in a liquid culture medium.

3. The method of claim 2, further comprising using at least one of the selectable markers to select for diploid cells that contain at least one of each of the first and second plasmids after contacting the first plurality of haploid yeast cells with the second plurality of haploid yeast cells.

4. The method of claim 2, wherein the recombined molecular barcode sequence from two or more diploid cells are sequenced to detect two or more different cell surface protein-protein interactions.

5. The method of claim 2, wherein the specific binding interaction between the first plurality of haploid yeast cells and the second plurality of haploid yeast cells occurs in a dilute mixture that has a spectral absorbance of less than 2.0 O.D.$_{600\ nm}$.

6. The method of claim 2, wherein a binding affinity between one protein of the first library of cell surface proteins and one protein of the second library of cell surface proteins is greater than a wild-type binding affinity between a yeast cell from the first mating type and a yeast cell from the second mating type.

7. The method of claim 6, wherein the binding affinity is at least two-fold, five-fold or ten-fold greater than the wild-type binding affinity.

8. The method of claim 2, wherein the first selectable marker and the second selectable marker are the same.

9. The method of claim 2, wherein the first selectable marker and the second selectable marker are different.

10. The method of claim 2, wherein the recombination is site-specific recombination.

11. The method of claim 2, wherein the recombination is CRE-Lox recombination.

12. The method of claim 2, wherein the first and the second unique oligonucleotide molecular barcode sequences are each between 5 and 50 nucleotides in length.

13. The method of claim 2, wherein the plasmids recombine with the genome of the haploid yeast cell or the diploid yeast cell.

14. The method of claim 2, wherein one or more of the first library of cell surface proteins and/or one or more of the second library of cell surface proteins are transmembrane proteins.

15. The method of claim 2, wherein one or more of the first library of cell surface proteins and/or one or more of the second library of cell surface proteins are integral membrane proteins.

16. The method of claim 2, wherein one or more of the first library of cell surface proteins and/or one or more of the second library of cell surface proteins are peripheral membrane proteins.

17. The method of claim 2, wherein one or more of the first library of cell surface proteins and/or one or more of the second library of cell surface proteins are encoded by mammalian genes.

18. The method of claim 2, wherein one or more of the first library of cell surface proteins and/or one or more of the second library of cell surface proteins are encoded by human genes.

19. The method of claim 2, wherein mating of the first and second plurality of haploid yeast cells is detected by a marker that becomes active only in the diploid cells.

20. The method of claim 2, wherein the diploid cells are detected by the presence of two distinct selectable markers.

21. The method of claim 2, wherein the sequencing comprises amplification of the recombined molecular barcode sequence.

22. The method of claim 2, wherein sequencing comprises amplification of one or more nucleotides of the sequence that encodes a protein of the first library of cell surface proteins in a first plasmid or at least one or more nucleotides of the sequence that encodes a protein of the second library of cell surface proteins in a second plasmid.

23. The method of claim 2, wherein each protein of the first library of cell surface proteins and each protein of the second library of cell surface proteins is a protein not normally expressed on the cell surface of the haploid yeast cell.

24. The method of claim 23, wherein each protein of the first library of cell surface proteins and each protein of the second library of cell surface proteins is a hybrid protein comprising at least one or more amino acid residues of a native, soluble protein fused to at least one or more amino acid residues of a native cell surface protein, wherein the at least one or more amino acid residues of the native, soluble protein is expressed on the outer surface of the haploid yeast cell.

25. The method of claim 24, wherein a linker connects the at least one or more amino acid residues of the native, soluble protein to the at least one or more amino acid residues of the native cell surface protein.

26. The method of claim 1, wherein the first gene expression cassettes and the second gene expression cassettes are integrated into the genome of the haploid yeast cell or the diploid yeast cell.

27. The method of claim 1, wherein the first gene expression cassettes and the second gene expression cassettes are carried by a 2 micron plasmid and are not integrated into the genome of the haploid yeast cell or the diploid yeast cell.

28. The method of claim 1, wherein the first gene expression cassettes and the second gene expression cassettes are carried by a centromeric plasmid and are not integrated into the genome of the haploid yeast cell or the diploid yeast cell.

* * * * *

SEQUENCE LISTING

<160> NUMBER OF SEQ ID NOS: 12

<210> SEQ ID NO 1
<211> LENGTH: 25
<212> TYPE: DNA
<213> ORGANISM: Artificial Sequence

```
<220> FEATURE:
<223> OTHER INFORMATION: Synthetic oligonucleotide

<400> SEQUENCE: 1
gtcggcggga ccagggagtt taaac                                              25

<210> SEQ ID NO 2
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 2
gccgatacga aggttttctc cagcg                                              25

<210> SEQ ID NO 3
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 3
gggaccgtca accctgaacc acaaa                                              25

<210> SEQ ID NO 4
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 4
tgagcaggca tcgagtgaag tcaac                                              25

<210> SEQ ID NO 5
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 5
gcttcaataa aggagcgagc acccg                                              25

<210> SEQ ID NO 6
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 6
cagaagcgag gcgaataaag gtggc                                              25

<210> SEQ ID NO 7
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 7
cgatacctgg ttgtgggctc tctca                                              25
```

```
<210> SEQ ID NO 8
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 8
tttgtctgac aaccgttcgc agagc                                            25

<210> SEQ ID NO 9
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 9
gtccctgaaa accactgagt tgccc                                            25

<210> SEQ ID NO 10
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 10
catggtcata gctgtttcct gtgt                                             24

<210> SEQ ID NO 11
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 11
gttcgccagt taatagtttg cgcaacg                                          27

<210> SEQ ID NO 12
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 12
ctcgaggggg gcggatcc                                                    18
```